US010214515B2

(12) United States Patent
Chen et al.

(10) Patent No.: US 10,214,515 B2
(45) Date of Patent: Feb. 26, 2019

(54) SUBSTITUTED PYRAZOLES AS INHIBITORS OF FIBROBLAST GROWTH FACTOR RECEPTOR

(71) Applicant: Zhejiang Hisun Pharmaceutical Co., Ltd., Taizhou (CN)

(72) Inventors: Lei Chen, Taizhou (CN); Dongliang Guan, Taizhou (CN); Hua Bai, Taizhou (CN); Xing Yan, Taizhou (CN); Shuai Miao, Taizhou (CN); Songsong Zhu, Taizhou (CN)

(73) Assignee: Zhejiang Hisun Pharmaceutical Co., Ltd. (CN)

( * ) Notice: Subject to any disclaimer, the term of this patent is extended or adjusted under 35 U.S.C. 154(b) by 0 days.

(21) Appl. No.: 15/741,639

(22) PCT Filed: Aug. 19, 2016

(86) PCT No.: PCT/CN2016/096088
§ 371 (c)(1),
(2) Date: Jan. 3, 2018

(87) PCT Pub. No.: WO2017/028816
PCT Pub. Date: Feb. 23, 2017

(65) Prior Publication Data
US 2018/0194751 A1  Jul. 12, 2018

(30) Foreign Application Priority Data

Aug. 20, 2015  (CN) .......................... 2015 1 0514203

(51) Int. Cl.
| | |
|---|---|
| *A61K 31/4155* | (2006.01) |
| *C07D 231/38* | (2006.01) |
| *C07D 403/14* | (2006.01) |
| *A61K 31/4184* | (2006.01) |
| *A61P 35/00* | (2006.01) |
| *C07D 233/06* | (2006.01) |
| *C07D 233/28* | (2006.01) |
| *C07D 233/46* | (2006.01) |
| *C07D 233/48* | (2006.01) |
| *C07D 401/14* | (2006.01) |

(52) U.S. Cl.
CPC ........ *C07D 403/14* (2013.01); *A61K 31/4184* (2013.01); *A61P 35/00* (2018.01); *C07D 233/06* (2013.01); *C07D 233/28* (2013.01); *C07D 233/46* (2013.01); *C07D 233/48* (2013.01); *C07D 401/14* (2013.01)

(58) Field of Classification Search
CPC ......................... A61K 31/4155; C07D 231/38
USPC ....................................... 514/407; 548/374.1
See application file for complete search history.

(56) References Cited

U.S. PATENT DOCUMENTS 9,102,692 B2  8/2015  Taka et al.

FOREIGN PATENT DOCUMENTS

| CN | 102574836 A | 7/2012 |
|---|---|---|
| EP | 2471786 B1 | 11/2015 |
| JP | 2012180344 A | 9/2012 |
| TW | 201116521 A1 | 5/2011 |
| WO | 2006000420 A1 | 1/2006 |
| WO | 2008075068 A2 | 6/2008 |
| WO | 2010129509 A1 | 11/2010 |
| WO | 2015099127 A1 | 7/2015 |
| WO | WO 17/028816 | * 2/2017 |

OTHER PUBLICATIONS

Jordan, V. C. Nature Reviews: Drug Discovery, 2, 2003, 205.*
Hackam, et al. JAMA, 296(14), 2006, 1731-1732.*
International Search Report from PCT/CN2016/096088 dated Oct. 8, 2016.

* cited by examiner

*Primary Examiner* — Douglas M Willis
(74) *Attorney, Agent, or Firm* — Lerner, David, Littenberg, Krumholz & Mentlik, LLP

(57) ABSTRACT

An indole derivative as expressed by Formula (I), a preparation method thereof, a pharmaceutical salt, and use thereof as a therapeutic agent, especially as a FGFR inhibitor. Each substituent in Formula (I) has identical definition as specified in the specification.

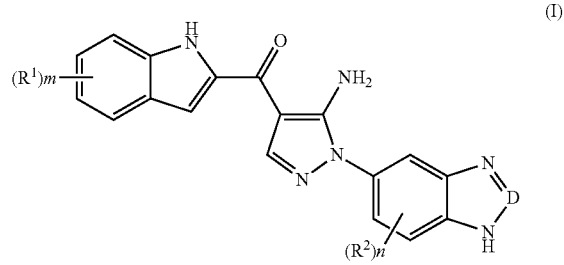

28 Claims, No Drawings

SUBSTITUTED PYRAZOLES AS INHIBITORS OF FIBROBLAST GROWTH FACTOR RECEPTOR

The present application is a national phase entry under 35 U.S.C. § 371 of International Application No. PCT/CN2016/096088 filed Aug. 19, 2016, published in Chinese, which claims priority from Chinese Application No. 201510514203.7 filed Aug. 20, 2015, both of which are incorporated herein by reference.

TECHNICAL FIELD

The present invention relates to a new indole derivative, preparation method thereof and a pharmaceutical composition comprising the derivative and use of the derivative as a therapeutic agent, in particular as a FGFR inhibitor.

TECHNICAL BACKGROUND

The family of fibroblast growth factor receptor (FGFR) is composed of four members (FGFR1, FGFR2, FGFR3 and FGFR4), which belong to the kinase of the receptor tyrosine kinases family. FGF binding results in dimerization of FGFR, followed by autophosphorylation of the receptors and activation of downstream signal pathways. Receptor activation is sufficient for the recovery and activation of specific downstream signal partners involved in the regulation of diversification processes such as cell growth, cell metabolism and cell survival. Thus, FGF/FGFR signal pathway has a multi-effect in many key biological processes such as tumor cell proliferation, migration, infiltration, angiogenesis.

In recent years, there have been a growing number of evidences showing that the mutations in the amplifications of FGFR1, FGFR2, FGFR3 and FGFR4 genes are present in various types of cancers. A large number of evidences show that: there are mutations of FGFR1 genes in breast cancer, non-small cell lung cancer, small cell lung cancer and glioblastoma, formation of fusion proteins caused by the gene transposition of FGFR1 in acute myeloid leukemia, over-expression of FGFR1 in pancreatic cancer, bladder cancer, prostate cancer, esophageal cancer; there is a phenomenon of gene mutation and amplification of the FGFR2 genes in gastric cancer, breast cancer and uterine cancer, while over-expression of FGFR2 in prostate cancer, esophageal cancer, ovarian cancer, pancreatic cancer, brain tumor, colorectal cancer; there are mutations of FGFR3 genes in multiple myeloma and bladder cancer, over-expression of FGFR3 in ovarian cancer, small cell lung cancer, non-small cell lung cancer, hepatocellular carcinoma; there are mutations of FGFR4 in lung cancer, ovarian cancer, prostate cancer and liver cancer etc., over-expression of FGFR4 in thyroid cancer, ovarian cancer.

At present, a series of FGFR inhibitor patents have been disclosed, including WO2006000420, WO2008075068 and WO2010129509 etc., the drugs that are currently in clinical phase II are LY-2874455, AZD-4547 and BGJ-398 etc., the drugs in clinical phase I are Debio-1347 and so on. But these studies for antitumor are far from enough, and it is still necessary to study and develop new FGFR inhibitors.

SUMMARY OF THE INVENTION

One of the objects of the present invention is to disclose a new class of indole derivatives or the pharmaceutically acceptable salts thereof.

The present invention provides a compound represented by the general formula (I) or a stereoisomer, a tautomer thereof or a pharmaceutically acceptable salt thereof:

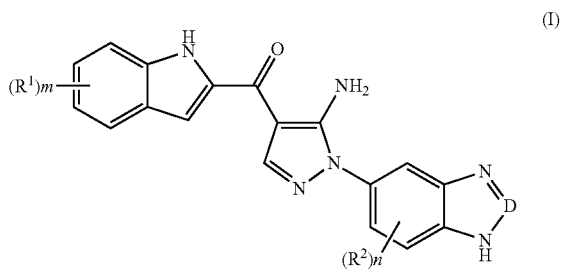

wherein:

D is selected from N or $CR^3$;

$R^1$ are each independently selected from the group consisting of hydrogen atom, alkyl, alkoxy, hydroxyl, halogen, nitro, cyano, cycloalkyl, heterocyclyl, aryl, heteroaryl, $-NR^4R^5$, $-C(O)NR^4R^5$, $-C(O)R^6$, $-OC(O)R^6$, $-C(O)OR^6$ or $-NR^4C(O)R^5$; wherein said alkyl, alkoxy, cycloalkyl, heterocyclyl, aryl or heteroaryl is optionally further substituted by one or more groups selected from the group consisting of halogen, hydroxyl, cyano, nitro, alkyl, alkoxy, cycloalkyl, heterocyclyl, aryl, heteroaryl, $-NR^4R^5$, $-C(O)NR^4R^5$, $-C(O)R^6$, $-OC(O)R^6$, $-C(O)OR^6$ or $-NR^4C(O)R^5$;

$R^2$ are each independently selected from the group consisting of hydrogen atom, alkyl, alkoxy, hydroxyl, halogen, nitro, cyano, cycloalkyl, heterocyclyl, $-NR^4R^5$, $-C(O)NR^4R^5$, $-C(O)R^6$, $-OC(O)R^6$, $-C(O)OR^6$ or $-NR^4C(O)R$, wherein said alkyl, alkoxy, cycloalkyl or heterocyclyl is optionally further substituted by one or more groups selected from the group consisting of alkyl, halogen, hydroxyl, cyano, nitro, cycloalkyl, heterocyclyl, aryl, heteroaryl, $-NR^4R^5$, $-C(O)NR^4R^5$, $-C(O)R^6$, $-OC(O)R^6$, $-C(O)OR^6$ or $-NR^4C(O)R^5$;

$R^3$ is selected from the group consisting of cycloalkyl, cyano, $-NR^4R^5$, $-C(O)OR^6$, $-OC(O)R^6$, $-NR^4C(O)R$ or $-C(O)NR^4R^5$, wherein said cycloalkyl is optionally further substituted with one or more halogen;

$R^4$, $R^5$ and $R^6$ are each independently selected from the group consisting of hydrogen atom, alkyl, cycloalkyl, heterocyclyl, sodium ion, aryl or heteroaryl, wherein said alkyl, cycloalkyl, heterocyclyl, aryl or heteroaryl is optionally further substituted by one or more groups selected from the group consisting of hydroxyl, halogen, nitro, cyano, alkyl, alkoxy, cycloalkyl, heterocyclyl, aryl, heteroaryl, $-NR^7R^8$, $-C(O)NR^7R^8$, $-C(O)R^9$, $-C(O)OR^9$ or $-NR^7C(O)R^8$;

or, $R^4$ and $R^5$, together with the attached N atom form a 4- to 8-membered heterocyclyl, wherein the 4- to 8-membered heterocyclic ring contains one or more N, O, $S(O)_p$ atom, and the 4- to 8-membered heterocyclic ring is further substituted by one or more groups selected from the group consisting of hydroxyl, halogen, nitro, cyano, alkyl, alkoxy, cycloalkyl, heterocyclyl, aryl, heteroaryl, $=O$, $-NR^7R^8$, $-C(O)NR^7R^8$, $-C(O)R^9$, $-C(O)OR^9$ or $-NR^7C(O)R^8$;

$R^7$, $R^8$ and $R^9$ are each independently selected from the group consisting of hydrogen atom, alkyl, cycloalkyl, heterocyclyl, aryl or heteroaryl, wherein said alkyl, cycloalkyl, heterocyclyl, aryl or heteroaryl is optionally substituted by one or more groups selected from the group consisting of hydroxyl, halogen, nitro, cyano, alkyl, alkoxy, cycloalkyl, heterocyclyl, aryl, heteroaryl, carboxyl or carboxylate;

m is 0, 1, 2, 3 or 4, preferably 0, 1 or 2;
n is 0, 1, 2 or 3, preferably 0, 1 or 2; and
p is 0, 1 or 2.

A preferred solution of the present invention, a compound represented by the general formula (I) or a stereoisomer, a tautomer thereof or a pharmaceutically acceptable salt thereof, wherein $R^1$ is selected from the group consisting of hydrogen atom or alkyl, m is selected from 0, 1 or 2.

A preferred solution of the present invention, a compound represented by the general formula (I) or a stereoisomer, a tautomer thereof or a pharmaceutically acceptable salt thereof, wherein $R^1$ is selected from halogen, preferably F, Cl or Br.

A preferred solution of the present invention, a compound represented by the general formula (I) or a stereoisomer, a tautomer thereof or a pharmaceutically acceptable salt thereof, wherein $R^1$ is selected from the group consisting of heteroaryl, preferably pyrazolyl, wherein said heteroaryl is optionally further substituted by one or more groups selected from alkyl, wherein said alkyl is preferably ethyl.

A preferred solution of the present invention, a compound represented by the general formula (I) or a stereoisomer, a tautomer thereof or a pharmaceutically acceptable salt thereof, 50 wherein $R^2$ is selected from the group consisting of hydrogen atom or alkyl, n is selected from 0, 1 or 2.

A preferred solution of the present invention, a compound represented by the general formula (I) or a stereoisomer, a tautomer thereof or a pharmaceutically acceptable salt thereof, wherein D is selected from $CR^3$.

A preferred solution of the present invention, a compound represented by the general formula (I) or a stereoisomer, a tautomer thereof or a pharmaceutically acceptable salt thereof, wherein:

D is selected from $CR^3$;
$R^1$ are each independently selected from hydrogen atom;
$R^2$ are each independently selected from hydrogen atom;
$R^3$ is selected from the group consisting of cycloalkyl, preferably cyclopropyl, cyclobutyl or cyclopentyl, more preferably cyclopropyl, wherein the cycloalkyl is optionally further substituted by one or more groups selected from halogen.

A preferred solution of the present invention, a compound represented by the general formula (I) or a stereoisomer, a tautomer thereof or a pharmaceutically acceptable salt thereof, wherein:

D is selected from $CR^3$;
$R^1$ are each independently selected from the group consisting of halogen, cyano, cycloalkyl, heterocyclyl or heteroaryl, wherein said cycloalkyl, heterocyclyl or heteroaryl is optionally further substituted by one or more groups selected from the group consisting of halogen, alkyl or alkoxy;
$R^2$ are each independently selected from hydrogen atom;
$R^3$ is selected from the group consisting of cycloalkyl, preferably cyclopropyl, cyclobutyl or cyclopentyl, more preferably cyclopropyl, wherein the cycloalkyl is optionally further substituted by one or more groups selected from halogen.

A preferred solution of the present invention, a compound represented by the general formula (I) or a stereoisomer, a tautomer thereof or a pharmaceutically acceptable salt thereof, wherein:

D is selected from $CR^3$;
$R^1$ are each independently selected from hydrogen atom;
$R^2$ are each independently selected from hydrogen atom;
$R^3$ is selected from —C(O)$OR^6$;
wherein $R^6$ is defined as in general formula (I).

A preferred solution of the present invention, a compound represented by the general formula (I) or a stereoisomer, a tautomer thereof or a pharmaceutically acceptable salt thereof, wherein:

D is selected from $CR^3$;
$R^1$ are each independently selected from hydrogen atom;
$R^2$ are each independently selected from hydrogen atom;
$R^3$ is selected from —C(O)$OR^6$;
$R^6$ is selected from the group consisting of hydrogen atom, methyl, ethyl, propyl or butyl, preferably methyl or ethyl.

A preferred solution of the present invention, a compound represented by the general formula (I) or a stereoisomer, a tautomer thereof or a pharmaceutically acceptable salt thereof, wherein:

D is selected from $CR^3$;
$R^1$ are each independently selected from hydrogen atom;
$R^2$ are each independently selected from hydrogen atom;
$R^3$ is selected from —$NR^4R^5$;
wherein $R^4$ and $R^5$ are defined as in general formula (I).

A preferred solution of the present invention, a compound represented by the general formula (I) or a stereoisomer, a tautomer thereof or a pharmaceutically acceptable salt thereof, wherein:

D is selected from $CR^3$;
$R^1$ are each independently selected from hydrogen atom;
$R^2$ are each independently selected from hydrogen atom;
$R^3$ is selected from —$NR^4C(O)R^5$;
wherein $R^4$ and $R^5$ are defined as in general formula (I).

A preferred solution of the present invention, a compound represented by the general formula (I) or a stereoisomer, a tautomer thereof or a pharmaceutically acceptable salt thereof, wherein:

D is selected from $CR^3$;
$R^1$ are each independently selected from hydrogen atom;
$R^2$ are each independently selected from hydrogen atom;
$R^3$ is selected from —C(O)$NR^4R^5$;
wherein $R^4$ and $R^5$ are defined as in general formula (I).

A preferred solution of the present invention, a compound represented by the general formula (I) or a stereoisomer, a tautomer thereof or a pharmaceutically acceptable salt thereof, wherein:

D is selected from $CR^3$;
$R^1$ are each independently selected from hydrogen atom;
$R^2$ are each independently selected from hydrogen atom;
$R^3$ is selected from —OC(O)$R^6$;
wherein $R^6$ is defined as in general formula (I).

Typical compounds of the present invention include, but not limited to,

| Example No. | Structure | Name |
|---|---|---|
| 1 | 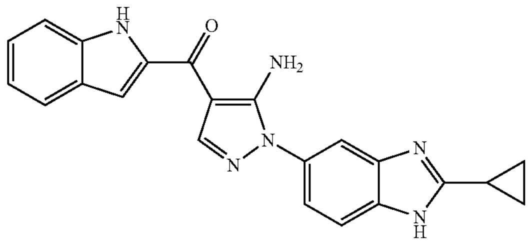 [SMILES: Nc1c(C(=O)c2cc3ccccc3[nH]2)cnn1-c1ccc2[nH]c(C3CC3)nc2c1] | (5-amino-1-(2-cyclopropyl-1H-benzo[d]imidazol-5-yl)-1H-pyrazol-4-yl)(1H-indol-2-yl)methanone |
| 2 | 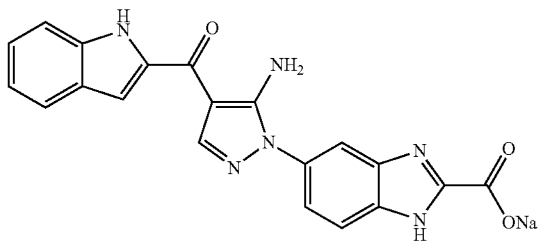 | sodium 5-(5-amino-4-(1H-indole-2-carbonyl)-1H-pyrazol-1-yl)-1H-benzo[d]imidazol-2-carboxylate |
| 3 | 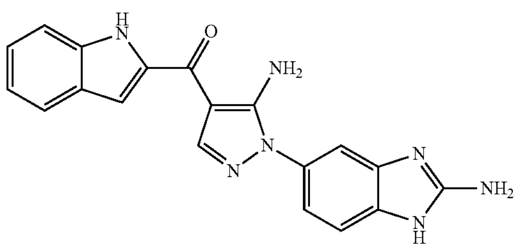 [SMILES: Nc1nc2cc(-n3ncc(C(=O)c4cc5ccccc5[nH]4)c3N)ccc2[nH]1] | (5-amino-1-(2-amino-1H-benzo[d]imidazol-5-yl)-1H-pyrazol-4-yl)(1H-indol-2-yl)methanone |
| 4 | 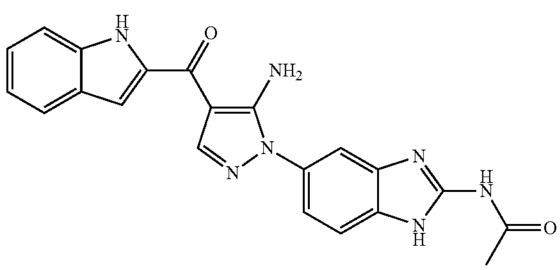 [SMILES: CC(=O)Nc1nc2cc(-n3ncc(C(=O)c4cc5ccccc5[nH]4)c3N)ccc2[nH]1] | N-(5-(5-amino-4-(1H-indole-2-carbonyl)-1H-pyrazol-1-yl)-1H-benzo[d]imidazol-2-yl)acetamide |
| 5 | 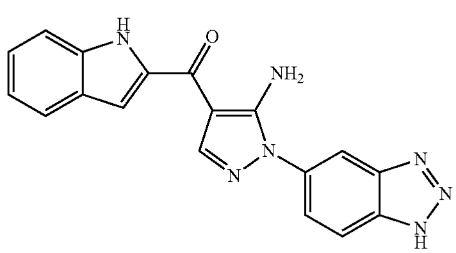 [SMILES: Nc1c(C(=O)c2cc3ccccc3[nH]2)cnn1-c1ccc2[nH]nnc2c1] | (5-amino-1-(1H-benzo[d][1,2,3]triazol-5-yl)-1H-pyrazol-4-yl)(1H-indol-2-yl)methanone |
| 6 | 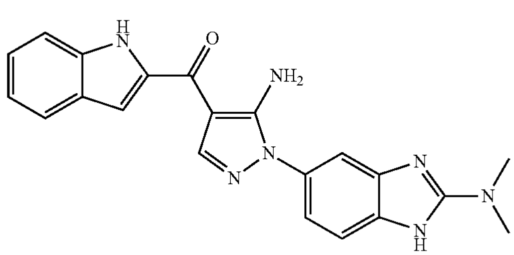 [SMILES: CN(C)c1nc2cc(-n3ncc(C(=O)c4cc5ccccc5[nH]4)c3N)ccc2[nH]1] | (5-amino-1-(2-(dimethylamino)-1H-benzo[d]imidazol-5-yl)-1H-pyrazol-4-yl)(1H-indol-2-yl)methanone |

-continued

| Example No. | Structure | Name |
|---|---|---|
| 7 | 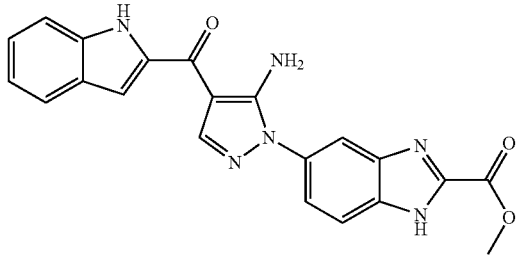 [SMILES: COC(=O)c1nc2cc(-n3ncc(C(=O)c4cc5ccccc5[nH]4)c3N)ccc2[nH]1] | methyl 5-(5-amino-4-(1H-indole-2-carbonyl)-1H-pyrazol-1-yl)-1H-benzo[d]imidazole-2-carboxylate |
| 8 | 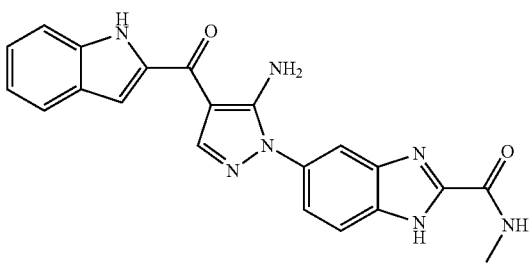 [SMILES: CNC(=O)c1nc2cc(-n3ncc(C(=O)c4cc5ccccc5[nH]4)c3N)ccc2[nH]1] | 5-(5-amino-4-(1H-indole-2-carbonyl)-1H-pyrazol-1-yl)-N-methyl-1H-benzo[d]imidazole-2-carboxamide |
| 9 | 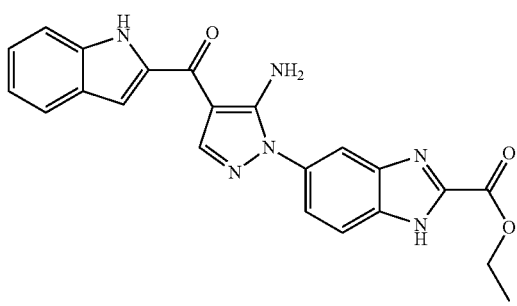 [SMILES: CCOC(=O)c1nc2cc(-n3ncc(C(=O)c4cc5ccccc5[nH]4)c3N)ccc2[nH]1] | ethyl 5-(5-amino-4-(1H-indole-2-carbonyl)-1H-pyrazol-1-yl)-1H-benzo[d]imidazole-2-carboxylate |
| 10 | 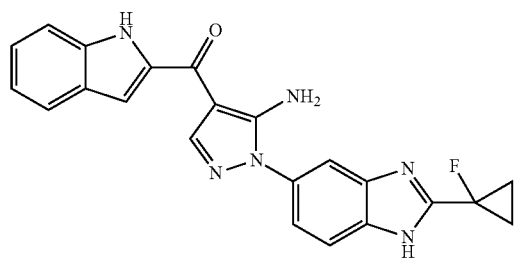 [SMILES: Nc1c(C(=O)c2cc3ccccc3[nH]2)cnn1-c1ccc2[nH]c(C3(F)CC3)nc2c1] | (5-amino-1-(2-(1-fluorocyclopropyl)-1H-benzo[d]imidazol-5-yl)-1H-pyrazol-4-yl)(1H-indol-2-yl)methanone |
| 11 | 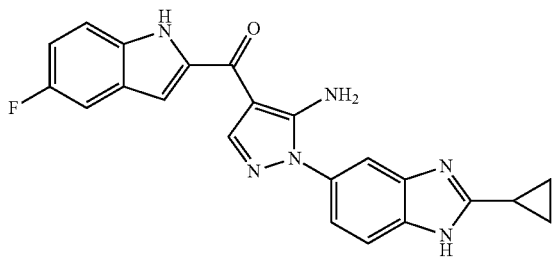 [SMILES: Nc1c(C(=O)c2cc3cc(F)ccc3[nH]2)cnn1-c1ccc2[nH]c(C3CC3)nc2c1] | (5-amino-1-(2-cyclopropyl-1H-benzo[d]imidazol-5-yl)-1H-pyrazol-4-yl)(5-fluoro-1H-indol-2-yl)methanone |

-continued

| Example No. | Structure | Name |
|---|---|---|
| 12 | 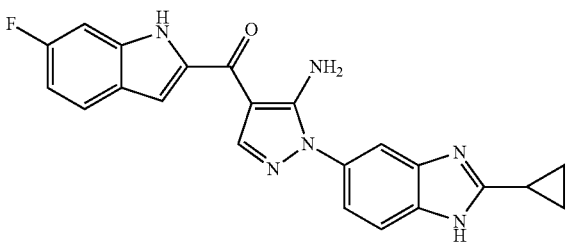 [SMILES: Nc1c(C(=O)c2cc3ccc(F)cc3[nH]2)cnn1-c1ccc2[nH]c(C3CC3)nc2c1] | (5-amino-1-(2-cyclopropyl-1H-benzo[d]imidazol-5-yl)-1H-pyrazol-4-yl)(6-fluoro-1H-indol-2-yl)methanone |
| 13 | 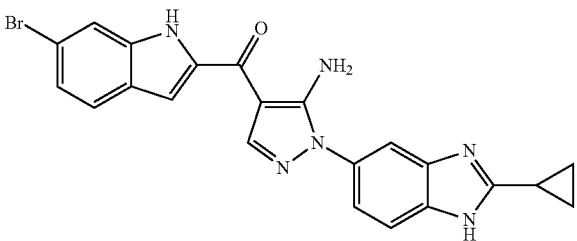 [SMILES: Nc1c(C(=O)c2cc3ccc(Br)cc3[nH]2)cnn1-c1ccc2[nH]c(C3CC3)nc2c1] | (5-amino-1-(2-cyclopropyl-1H-benzo[d]imidazol-5-yl)-1H-pyrazol-4-yl)(6-fluoro-1H-indol-2-yl)methanone |
| 14 | 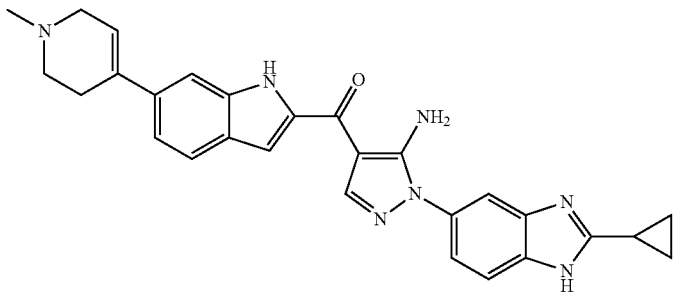 [SMILES: CN1CC=C(c2ccc3cc(C(=O)c4cnn(-c5ccc6[nH]c(C7CC7)nc6c5)c4N)[nH]c3c2)CC1] | (5-amino-1-(2-cyclopropyl-1H-benzo[d]imidazol-5-yl)-1H-pyrazol-4-yl)(6-(1-methyl-1,2,3,6-tetrahydropyrid-4-yl)-1H-indol-2-yl)methanone |
| 15 | 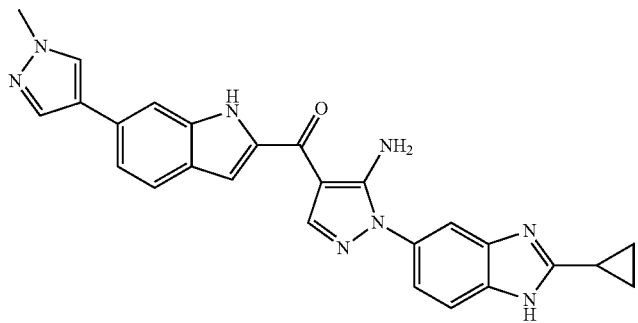 [SMILES: Cn1cc(-c2ccc3cc(C(=O)c4cnn(-c5ccc6[nH]c(C7CC7)nc6c5)c4N)[nH]c3c2)cn1] | (5-amino-1-(2-cyclopropyl-1H-benzo[d]imidazol-5-yl)-1H-pyrazol-4-yl)(6-(1-methyl-1H-pyrazol-4-yl)-1H-indol-2-yl)methanone |

| Example No. | Structure | Name |
|---|---|---|
| 16 | 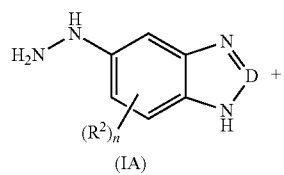 | (5-amino-1-(2-cyclopropyl-1H-benzo[d]imidazol-5-yl)-1H-pyrazol-4-yl)(6-(1-ethyl-1H-pyrazol-4-yl)-1H-indol-2-yl)methanone |
| 17 | 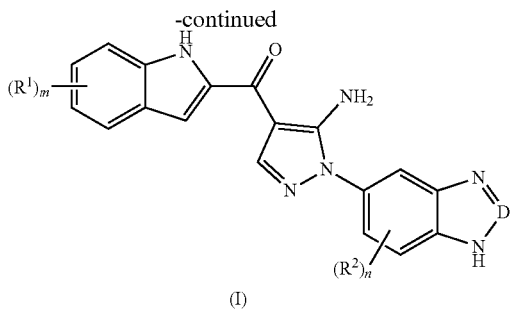 | 2-(5-amino-1-(2-cyclopropyl-1H-benzo[d]imidazol-5-yl)-1H-pyrazole-4-carbonyl)-1H-indole-6-carbonitrile | or a stereoisomer, a tautomer thereof or a pharmaceutically acceptable salt thereof.

Further, the present invention provides a method for the preparation of a compound of the general formula (I), which comprises:

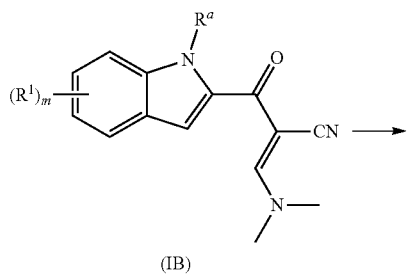

(IA)

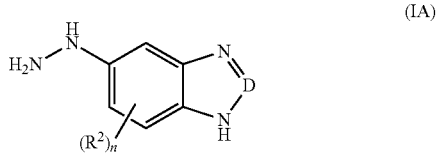

(I)

The compound of the general formula (IA) is reacted with a compound of the general formula (IB), and when $R^a$ is a protecting group of N, the protecting group $R^a$ is further deprotected to obtain a compound of the general formula (I); wherein:

$R^a$ is selected from the group consisting of hydrogen atom or a protecting group of N, preferably phenylsulfonyl;

$R^1$, $R^2$, D, m and n are defined as in general formula (I).

The present invention provides a compound of the general formula (IA) or a stereoisomer, a tautomer thereof or a pharmaceutically acceptable salt thereof, (IA)

Wherein: $R^2$, D and n are defined as in general formula (I).

Typical compounds of general formula (IA) include, but not limited to:

| No. | Structure | Name |
|---|---|---|
| 1e | 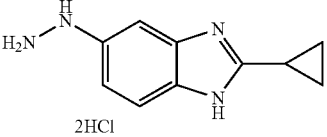 [SMILES: NNc1ccc2[nH]c(C3CC3)nc2c1] | 2-cyclopropyl-5-hydrazinyl-1H-benzo[d]imidazole dihydrochloride |
| 2e | 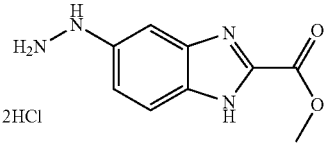 | methyl 5-hydrazinyl-1H-benzo[d]imidazole-2-carboxylate dihydrochloride |
| 3d | 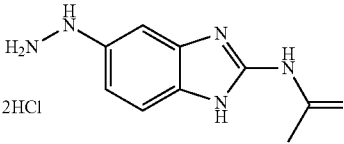 | N-(5-hydrazinyl-1H-benzo[d]imidazol-2-yl)acetamide dihydrochloride |
| 5b | 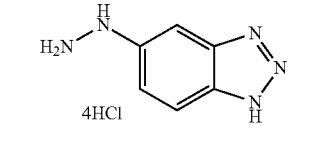 [SMILES: NNc1ccc2[nH]nnc2c1] | 5-hydrazinyl-1H-benzo[d][1,2,3]triazole tetrahydrochloride |
| 6e | 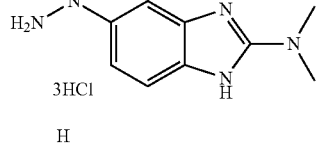 | 5-hydrazinyl-N,N-dimethyl-1H-benzo[d]imidazol-2-amine trihydrochloride |
| 10d | 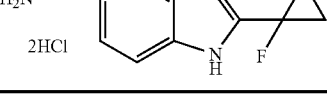 | 2-(1-fluorocyclopropyl)-5-hydrazinyl-1H-benzo[d]imidazole dihydrochloride | or a stereoisomer, a tautomer thereof.

Typical compounds of general formula (IA) also include, but not limited to:

| No. | Structure | Name |
|---|---|---|
| 1e' | 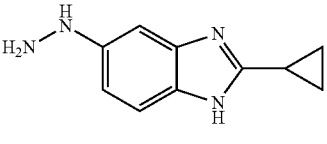 [SMILES: NNc1ccc2[nH]c(C3CC3)nc2c1] | 2-cyclopropyl-5-hydrazinyl-1H-benzo[d]imidazole |
| 2e' | 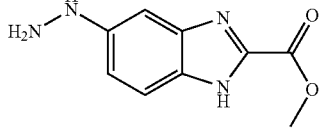 | methyl 5-hydrazinyl-1H-benzo[d]imidazole-2-carboxylate |
| 3d' | 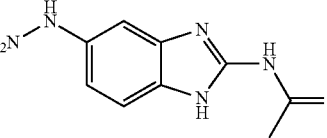 | N-(5-hydrazinyl-1H-benzo[d]imidazol-2-yl)acetamide |

| No. | Structure | Name |
|---|---|---|
| 5b' | 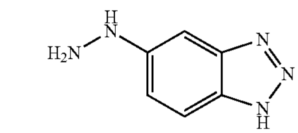 [SMILES: NNc1ccc2[nH]nnc2c1] | 5-hydrazinyl-1H-benzo[d][1,2,3]triazole |
| 6e' | 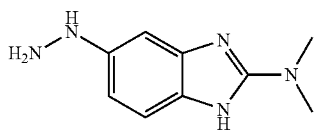 | 5-hydrazinyl-N,N-dimethyl-1H-benzo[d]imidazol-2-amine |
| 10d' | | 2-(1-fluorocyclopropyl)-5-hydrazinyl1H-benzo[d]imidazole | or a stereoisomer, a tautomer thereof or a pharmaceutically acceptable salt thereof.

Further, the present invention provides a method for the preparation of a compound of the general formula (IA), which comprises:

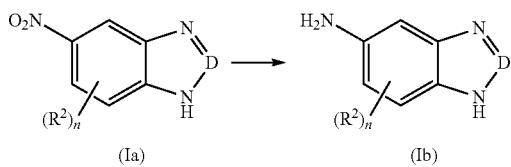

The compound of the general formula (Ia) is subjected to a reduction reaction to obtain a compound of the general formula (Ib):

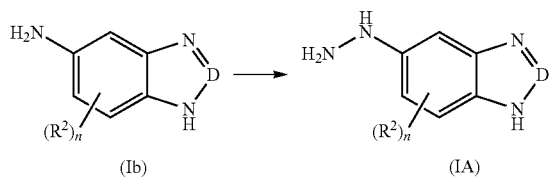

The compound of the general formula (Ib) is reacted with concentrated hydrochloric acid and nitrite in an ice bath to obtain a compound of the general formula (IA) or a salt thereof under the condition of stannous chloride or a hydrate thereof;

Wherein: $R^2$, D and n are defined as in general formula (IA).

Still further, the present invention provides a pharmaceutical composition comprising an effective amount of a compound of general formula (I) or a stereoisomer, a tautomer thereof or a pharmaceutically acceptable salt thereof, and pharmaceutically acceptable carriers, excipients, or combinations thereof.

The present invention provides a method for inhibiting FGFR in vitro, comprising contacting said receptor with a compound of general formula (I) or a stereoisomer, a tautomer thereof or a pharmaceutically acceptable salt thereof, or a composition thereof, wherein the FGFR is preferably selected from FGFR1, FGFR2, FGFR3.

The present invention provides use of a compound of the general formula (I) or a stereoisomer, a tautomer thereof or a pharmaceutically acceptable salt thereof, or a pharmaceutical composition thereof in the preparation of a medicament of a FGFR inhibitor, wherein said FGFR is preferably selected from FGFR1, FGFR2, FGFR3, more preferably FGFR2.

The present invention provides a use of a compound of the general formula (I) or a stereoisomer, a tautomer thereof or a pharmaceutically acceptable salt thereof, or a pharmaceutical composition thereof in the preparation of a medicament for the treatment of cancer, wherein said cancer is selected from lung cancer, gastric cancer, multiple myeloma, bladder cancer or liver cancer, preferably small cell lung cancer, gastric cancer, bladder cancer, multiple myeloma, more preferably gastric cancer.

DETAILED DESCRIPTION OF THE INVENTION

Unless otherwise stated, certain terms used in the description and claims are defined as follows:

"Alkyl" refers to an aliphatic hydrocarbon group comprising a $C_1$-$C_{20}$ straight-chain or branched-chain when used as a group or a part of a group, preferably $C_1$-$C_{10}$ alkyl, more preferably $C_1$-$C_6$ alkyl. Examples of an alkyl group include, but not limited to, methyl, ethyl, n-propyl, isopropyl, n-butyl, isobutyl, t-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethyl butyl, 1,3-dimethylbutyl, 2-ethylbutyl, 2-methylpentyl, 3-methylpentyl, 4-methylpentyl, 2,3-dimethylbutyl and so on. The alkyl group may be substituted or unsubstituted.

"Alkenyl" refers to an alkyl group as defined above consisting of at least two carbon atoms and at least one carbon-carbon double bond, and representative examples include, but not limited to, vinyl, 1-propenyl, 2-propenyl, 1-, 2- or 3-butenyl and the like. The alkenyl group may be optionally substituted or unsubstituted.

When used as a group or part of a group, "alkynyl" refers to an aliphatic hydrocarbon group containing one carbon-carbon triple bond, which may be straight or branched, preferably $C_2$-$C_{10}$ alkynyl, more preferably $C_2$-$C_6$ alkynyl, most preferably $C_2$-$C_4$ alkynyl. Examples of an alkynyl group include, but not limited to, ethynyl, 1-propynyl, 2-propynyl, 1-, 2- or 3-butynyl. The alkynyl group may be substituted or unsubstituted.

"Cycloalkyl" refers to a saturated or partially saturated monocyclic, fused, bridged and spiro carbon ring, preferably $C_3$-$C_{12}$ cycloalkyl, more preferably $C_3$-$C_8$ cycloalkyl, and most preferably $C_3$-$C_6$ cycloalkyl. Examples of monocyclic cycloalkyl include, but not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl and the like, preferably cyclopropyl, cyclohexenyl.

"Spirocycloalkyl" refers to a 5 to 18 membered polycyclic group comprising two or more cyclic structures with single ring sharing one common carbon atom (named as spiro atom), which may contain one or more double bonds, but none of the rings has a completely conjugated pi-electron aromatic system. Preferably a spirocycloalkyl is 6 to 14 membered, more preferably 7 to 10 membered. According to the number of the common spiro atom between the rings, spirocycloalkyl is divided into mono-spirocycloalkyl, di-spirocycloalkyl, or poly-spirocycloalkyl, preferably mono-spirocycloalkyl and di-spirocycloalkyl, preferably 4-membered/5-membered, 4-membered/6-membered, 5-membered/5-membered, or 5-membered/6-membered. Non-limiting examples of spirocycloalkyls include but not limited to: spiro [4.5]decyl, spiro [4.4]nonyl, spiro [3.5] nonyl, spiro [2.4]heptyl.

"Fused cycloalkyl" refers to 5 to 18 membered polycyclic all-carbon group, comprising two or more cyclic structures sharing an adjacent pair of carbon atoms with other rings, wherein one or more rings may contain one or more double bonds, but none of the rings has a completely conjugated pi-electron aromatic system. Preferably a fused cycloalkyl group is 6 to 12 membered, more preferably 7 to 10 membered. According to the number of membered rings, fused cycloalkyl is divided into bicyclic, tricyclic, tetracyclic or polycyclic fused cycloalkyl, preferably bicyclic or tricyclic fused cycloalkyl, more preferably 5-membered/5-membered, or 5-membered/6-membered bicyclic fused cycloalkyl. Non-limiting examples of fused cycloalkyl include, but not limited to: bicyclo[3.1.0]hexyl, bicyclo [3.2.0]hept-1-enyl, bicycle[3.2.0]heptyl, decahydronaphthalenyl or tetradecahydrophenanthrenyl.

"Bridged cycloalkyl" refers to 5 to 18 membered polycyclic all-carbon groups, comprising two or more cyclic structures sharing two disconnected carbon atoms with each other, wherein one or more ring may contain one or more double bonds but none of the rings has a completely conjugated pi-electron aromatic system. Preferably a bridged cycloalkyl is 6 to 12 membered, more preferably 7 to 10 membered. Preferably 6 to 14 membered, more preferably 7 to 10 membered. According to the number of membered rings, bridged cycloalkyl is divided into bicyclic, tricyclic, tetracyclic or polycyclic bridged cycloalkyl, preferably refers to bicyclic, tricyclic or tetracyclic bridged cycloalkyl, more preferably bicyclic or tricyclic bridged cycloalkyl. Non-limiting examples of bridged cycloalkyl include, but not limited to: (1s, 4s)-bicyclo[2.2.1]heptyl, bicyclo[3.2.1] octyl, (1s, 5s)-bicyclo o[3.3.1]nonyl, bicyclo[2.2.2]octyl, (1r, 5r)-bicyclo[3.3.2]decyl.

Said cycloalkyl can be fused to aryl, heteroaryl or the ring of heterocyclic alkyl, wherein the ring bound to parent structure is cycloalkyl. Non-limiting examples include indanyl, tetrahydronaphthyl, benzocycloheptyl and so on. The cycloalkyl group may be optionally substituted or unsubstituted.

"Heterocyclyl", "heterocycle" or "heterocyclic" are used interchangeably herein to refer to a non-aromatic heterocyclyl in which one or more ring-forming atoms are heteroatoms such as oxygen, nitrogen, sulfur atoms, etc., including single ring, fused ring, bridge ring and spiro ring. Preferably a heterocyclyl has a 5 to 7 membered monocyclic ring or 7 to 10 membered bis- or tricyclic rings which may contain 1, 2 or 3 atoms selected from nitrogen, oxygen and/or sulfur. Examples of "heterocyclyl" include, but not limited to, morpholinyl, thiomorpholinyl, tetrahydropyranyl, 1,1-dioxo-thiomorpholinyl, piperidinyl, 2-oxo-piperidinyl, pyrrolidinyl, 2-oxo-pyrrolidinyl, piperazin-2-one, 8-oxa-3-azabicyclo[3.2.1]octyl and piperazinyl. The heterocyclyl group may be substituted or unsubstituted.

"Spiroheterocyclyl" refers to 5 to 18 membered polycyclic heterocyclyl comprising two or more cyclic structures and single rings share one common atom with each other, wherein the said ring may contains one or more double bonds, but none of the rings has a completely conjugated pi-electron aromatic system, wherein one or more ring atoms are hetero atoms that are selected from N, O, or $S(O)_p$ (wherein p is selected from 0, 1, or 2) with the remaining ring atoms being C. Preferably a spiroheterocyclyl group is 6 to 14 membered, more preferably 7 to 10 membered. According to the number of common spiro atoms between rings, spiroheterocyclyl is divided into mono-spiroheterocyclyl, di-spiroheterocyclyl, or poly-spiroheterocyclyl, preferably mono-spiroheterocyclyl and di-spiroheterocyclyl. More preferably 4-membered/4-membered, 4-membered/5-membered, 4-membered/6-membered, 5-membered/5-membered or 5-membered/6-membered mono-spiroheterocyclyl. Non-limiting examples of "spiroheterocyclyl" include, but not limited to: 1,7-dioxaspiro[4.5]decyl, 2-oxa-7-azaspiro [4.4]nonyl, 7-oxaspiro[3.5]nonyl and 5-oxaspiro[2.4]heptyl.

"Fused heterocyclyl" refers to a all-carbon polycyclic group comprising two or more cyclic structure sharing an adjacent pair of atoms with each other, one or more rings may contain one or more double bonds, but none of the rings has a completely conjugated pi-electron aromatic system, wherein one or more ring atoms are heteroatoms selected from N, O, or $S(O)_p$ (wherein p is selected from 0, 1, or 2) with the remaining ring atoms being C. Preferably a fused heterocyclyl group is 6 to 14 membered, more preferably 7 to 10 membered. According to the number of membered ring, fused heterocyclyl is divided into bicyclic, tricyclic, tetracyclic or polycyclic fused heterocyclyl, preferably bicyclic or tricyclic fused heterocyclyl, more preferably 5-membered/5-membered or 5-membered/6-membered bicyclic fused heterocyclyl. Non-limiting examples of "fused heterocyclyl" include but not limited to: octahydropyrrolo[3,4-c] pyrrolyl, octahydro-1H-isoindolyl, 3-azabicyclo[3.1.0] hexyl, octahydrobenzo[b][1,4]dioxine.

"Bridged heterocyclyl" refers to 5 to 14 membered, 5 to 18 membered polycyclic group comprising two or more cyclic structures sharing two disconnected atoms with each other, one or more rings may contain one or more double bonds but none of the rings has a completely conjugated pi-electron aromatic system, wherein one or more ring atoms are heteroatoms selected from N, O, or $S(O)_p$ (wherein p is selected from 0, 1 or 2) with the remaining ring atoms being C. Preferably a bridged heterocyclyl group is 6 to 14 membered, more preferably 7 to 10 membered. According to the number of membered ring, bridged heterocyclyl is divided into bicyclic, tricyclic, tetracyclic or polycyclic bridged heterocyclyl, preferably bicyclic, tricyclic or tetracyclic bridged heterocyclyl, more preferably bicyclic or tricyclic bridged heterocyclyl. Non-limiting examples of bridged heterocyclyl include but not limited to: 2-azabicyclo[2.2.1]heptyl, 2-azabicyclo[2.2.2]octyl and 2-azabicyclo[3.3.2]decyl. Said heterocyclyl ring may be fused to an aryl, heteroaryl or cycloalkylring, wherein the ring attached to the parent structure is a heterocyclyl. The heterocyclyls may be optionally substituted or unsubstituted.

"Aryl" refers to a carbon ring aromatic system comprising one or two rings, wherein said ring can be fused to each other. The term "aryl" comprises aromatic group such as phenyl, naphthyl, tetrahydronaphthyl. Preferably an aryl group is a $C_6$-$C_{10}$ aryl, more preferably a phenyl or naphthyl, most preferably a phenyl. The aryl group may be substituted or unsubstituted. Said "aryl" can be fused to heteroaryl, heterocyclyl or cycloalkyl, wherein the ring attached to the parent structure is the aromatic ring. Non-limiting example comprises but not limited to:

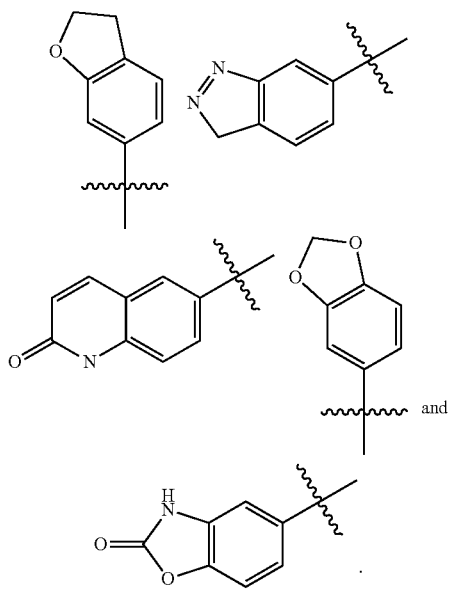

"Heteroaryl" refers to an aromatic 5 to 6 membered monocyclic ring or 9 to 10 member bicyclic ring having 1 to 4 atoms selected from N, O and/or S. Examples of "heteroaryl" include but not limited to furyl, pyridyl, 2-oxo-1,2-dihydropyridyl, pyridazinyl, pyrimidinyl, pyrazinyl, thienyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzodioxolyl, benzimidazolyl, indolyl, isoindolyl, 1,3-dioxo-isoindolyl, quinolinyl, indazolyl, benzoisothiazolyl, benzooxazolyl and benzoisoxazolyl. The heteroaryl group may be substituted or unsubstituted. The heteroaryl ring may be fused to an aryl, heterocyclyl or cycloalkyl ring, wherein the ring attached to the parent structure is a heteroaryl ring. Non-limiting examples include, but not limited to:

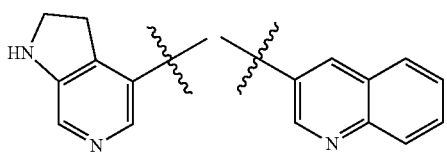

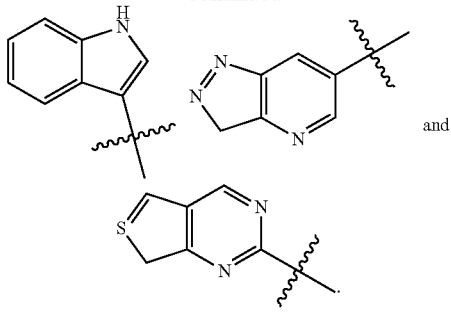

"Alkoxyl" refers to (alkyl-O—) group, wherein the alkyl is defined as above. $C_1$-$C_6$ alkoxyl is preferably selected. Examples of alkoxyl include but not limited to: methoxy, ethoxy, n-propoxy, isopropoxy, n-butoxy, isobutoxy, t-butoxy and so on.

"Hydroxyl" refers to an —OH group.

"Halogen" refers to fluoro, chloro, bromo and iodo, preferably chloro, bromo and iodo.

"Amino" refers to a —$NH_2$ group.

"Cyano" refers to a —CN group.

"Nitro" refers to a —$NO_2$ group.

"Benzyl" refers to a —$CH_2$-phenyl group.

"Carboxyl" refers to a —C(O)OH group.

The term "carboxylate group" refers to a —C(O)O(alkyl) or (cycloalkyl) group, wherein the alkyl, cycloalkyl are defined as above.

"Substituted" refers to one or more hydrogen atoms in the group, preferably up to 5, more preferably 1 to 3 hydrogen atoms independently substituted by corresponding number of groups. It goes without saying that the groups exist only in their possible chemical positions. A person skilled in the art is able to determine whether the substitution is possible or not without paying excessive efforts by experiment or theory. For example, the combination of amino or hydroxyl group having free hydrogen and carbon atoms having unsaturated (such as olefinic) bonds may be unstable.

"Substitute" or "substituted" as used herein, unless otherwise specified, means that the group may be substituted by one or more groups selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocycloalkylthio, amino, haloalkyl, hydroxyalkyl, carboxyl, carboxylate group, =O, —$NR^4R^5$, —C(O)$NR^4R^5$, —C(O)$R^6$, —OC(O)$R^6$, —C(O)O$R^6$ or —$NR^4C(O)R^5$, wherein $R^4$, $R^5$ and $R^6$ are defined as in general formula (I).

"Pharmaceutically acceptable salts" refer to certain salts of the above compounds that keep their original biological activity and are suitable for pharmaceutical uses. The pharmaceutically acceptable salts of the compound of the formula (I) can be metal salts, amine salts that are formed with suitable acids. The metal salts preferably are alkali metal salts, alkaline earth metal salts. The suitable acid including an inorganic acid and an organic acid such as acetic acid, benzenesulfonic acid, benzoic acid, camphorsulfonic acid, citric acid, ethanesulfonic acid, fumaric acid, gluconic acid, glutamic acid, hydrobromic acid, hydrochloric acid, isethionic acid, lactic acid, malic acid, maleic acid, mandelic acid, methanesulfonic acid, nitric acid, phosphoric acid, succinic acid, sulfuric acid, tartaric acid, p-toluenesulfonic acid and the like. Particularly preferred are hydrochloric acid, hydrobromic acid, phosphoric acid and sulfuric acid, most preferably hydrochloride.

"Pharmaceutical composition" refers to a mixture of one or more of the compounds described in the present invention or physiologically pharmaceutically acceptable salts or prodrugs thereof and other chemical components, and other components such as physiologically pharmaceutically acceptable carriers and excipients. The purpose of a pharmaceutical composition is to promote administration to an organism, which is conducive to the absorption of the active ingredient and thus displaying biologically activity.

THE SYNTHESIS METHOD OF THE COMPOUND OF THE PRESENT INVENTION

In order to accomplish the purpose of the present invention, the present invention applies the following technical solution:

A method for preparing a compound of the general formula (I) or a salt thereof comprising the following steps:

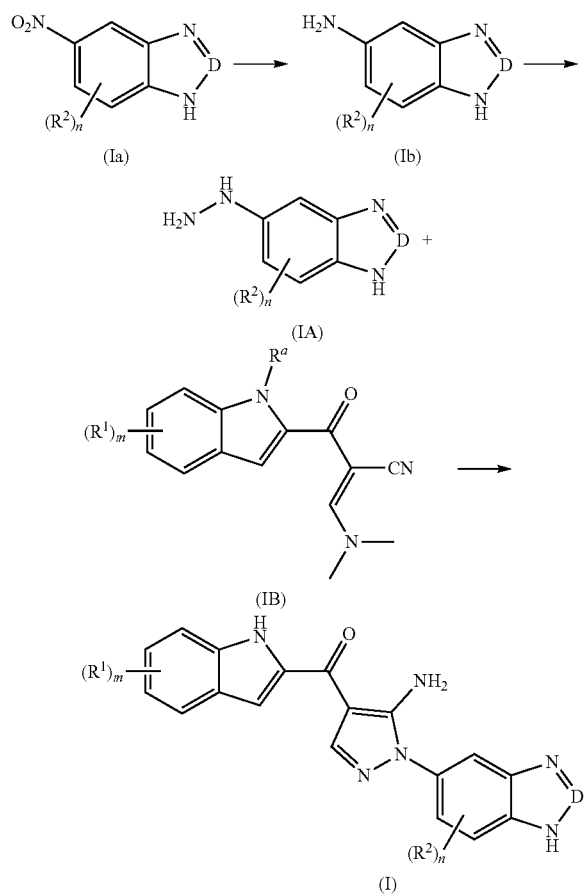

The nitro group of the compound of the general formula (Ia) is reduced in a hydrogen atmosphere to obtain a compound of the general formula (Ib); the compound of the general formula (Ib) is reacted with concentrated hydrochloric acid and nitrite under ice bath condition, to obtain the compound of the general formula (IA) under the condition of stannous chloride and hydrate thereof; the compound of the general formula (IA) is reacted with the compound of the general formula (IB), and when $R^a$ is a protecting group of N, the protecting group $R^a$ is deprotected to give a compound of formula (I);

$R^a$ is selected from the group consisting of hydrogen atom or a protecting group of N, preferably phenylsulfonyl group;

$R^1$, $R^2$, D, m and n are defined as in general formula (I).

EMBODIMENTS

The following examples are provided for further describing the present invention, but these examples are not provided for limiting the scope of the present invention.

EXAMPLES

Examples show the preparation of representative compounds represented by formula (I) and related identification data of structures. It will be understood that the following examples are provided to illustrate the present invention but not limiting the present invention. The $^1$H NMR spectrum is determined using a Bruker instrument (400 MHz), and the chemical shift is expressed in ppm using tetramethylsilane standard (0.00 ppm). The representation of 1H NMR: s=single peak, d=double peaks, t=triple peaks, m=multiple peaks, br=broad, dd=the double peaks of double peaks, dt=the double peaks of triple peaks. If the coupling constant is provided, the unit of the constant is Hz.

The mass spectrum is determined by LC/MS, and the ionization mode could be electro spray (ESI) or atmospheric pressure chemical ionization (APCI).

Thin layer chromatography silica gel plate using the silica gel plates of Yantai Yellow Sea HSGF254 or Qingdao Ocean Chemical GF254, the dimension of the silica gel plates used in thin layer chromatography (TLC) is 0.15 mm-0.2 mm, the dimension of the products of thin layer chromatography separation and purification is 0.4 mm-0.5 mm.

Generally, Yantai Huanghai silica gel, 200-300 mesh silica gel is used as the carrier for column chromatography.

In the following examples, unless otherwise indicated, all temperatures are Celsius temperatures, unless otherwise indicated, various starting materials and reagents are commercially available or are synthesized according to known methods, and commercially available materials and reagents are directly used without further purified, unless otherwise specified, commercially available manufacturers include, but not limited to, Aldrich Chemical Company, ABCR GmbH & Co.KG, Acros Organics, Guangzan Chemical Technology Co., Ltd. and Jingyan Chemical Technology Co., Ltd.

CD$_3$OD: deuterated methanol.
CDCl$_3$: deuterated chloroform.
DMSO-d$_6$: deuterated dimethylsulfoxide.

The term "argon atmosphere" refers to that the reaction flask is equipped with an argon balloon of about 1 L volume.

In the examples, unless otherwise stated, the solution used in examples refers to an aqueous solution.

The compounds are purified with a developing agent system of column chromatography and a developing agent system of thin layer chromatography, wherein the developing agent system is selected from: A: cyclohexane and ethyl acetate system; B: dichloromethane and methanol system; C: petroleum ether and ethyl acetate system; D: n-hexane: acetone system, in which the volume ratio of the solvents varies according to the polarities of the compounds, and a small amount of an acidic or alkaline reagent may be added, such as acetic acid or triethylamine and the like.

Example 1

(5-amino-1-(2-cyclopropyl-1H-benzo[d]imidazol-5-yl)-1H-pyrazol-4-yl)(1H-indol-2-yl)methanone

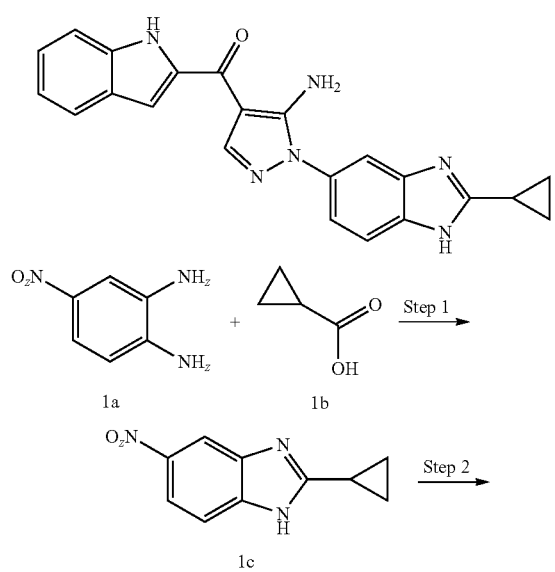

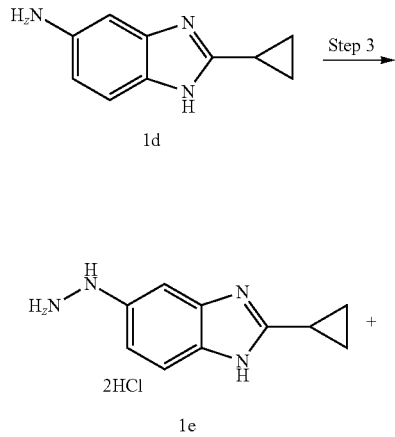

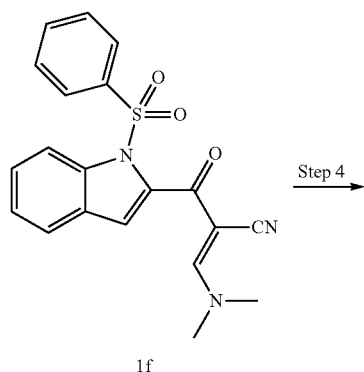

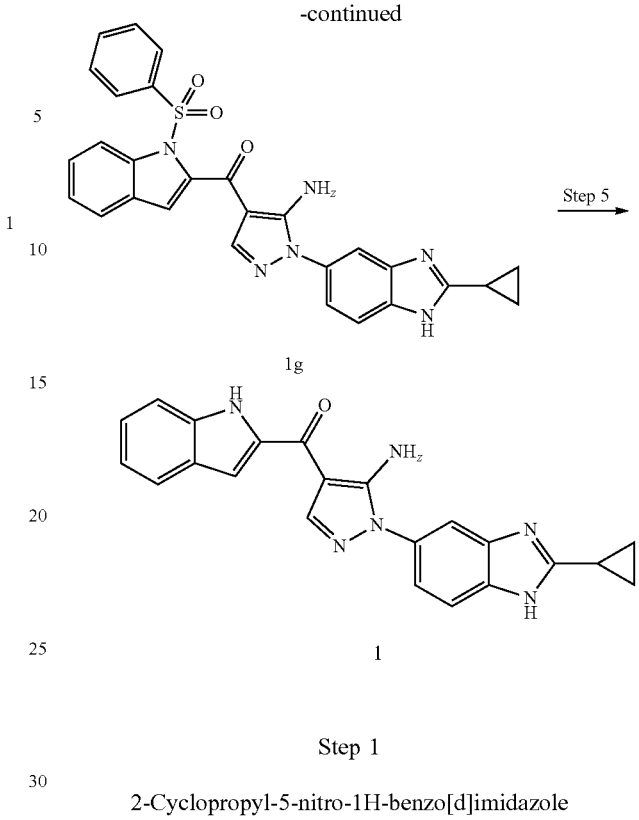

Step 1

2-Cyclopropyl-5-nitro-1H-benzo[d]imidazole

4-Nitrobenzene-1,2-diamine 1a (3 g, 19.6 mmol) and cyclopropanecarboxylic acid 1b (1.86 g, 21.55 mmol) were dissolved in polyphosphoric acid, the reaction solution was reacted at 100° C. for 4 hours. 50 mL of ice-water mixture was added to the reaction solution, the pH was adjusted to 9 to 10 with sodium hydroxide, and white solid precipitated. The mixture was subjected to suction filtration, the filter cake was washed with water and then was subjected to infrared drying to obtain crude 2-cyclopropyl-5-nitro-1H-benzo[d]imidazole 1c (6.09 g, off-white solid), yield: 153%.

MS m/z (ESI): 203.9 [M+1]

Step 2

2-Cyclopropyl-1H-benzo[d]imidazol-5-amine

2-Cyclopropyl-5-nitro-1H-benzo[d]imidazole 1c (1.5 g, 7.38 mmol) was dissolved in 30 mL of absolute ethanol, 10% palladium/carbon (150 mg) was added under stirring. The mixture was stirred overnight at room temperature under hydrogen atmosphere then it is filtered, the filter cake was washed with anhydrous methanol (20 mL×3), the filtrate was concentrated under reduced pressure to obtain 2-cyclopropyl-1H-benzo[d]imidazol-5-amine 1d (1.1 g, brown solid), yield: 86%.

MS m/z (ESI): 174.0 [M+1]

Step 3

2-Cyclopropyl-5-hydrazinyl-1H-benzo[d]imidazole dihydrochloride

2-Cyclopropyl-1H-benzo[d]imidazol-5-amine 1d (1 g, 5.77 mmol) was suspended in 10 mL of hydrochloric acid, the reaction solution was cooled down to 0° C. in an ice bath.

1 mL of sodium nitrite (398 mg, 5.77 mmol) solution was added dropwise, the reaction solution was cooled down to 0° C. After 20 minutes of reaction, 1 mL of solution of stannous chloride dihydrate (2.61 g, 11.55 mmol) in concentrated hydrochloric acid was added dropwise. The reaction solution continued to react at 0° C. for 0.5 hours. The reaction solution was filtered under reduced pressure, the filter cake was subjected to infrared drying to obtain crude 2-cyclopropyl-5-hydrazinyl-1H-benzo[d]imidazole dihydrochloride 1e (1.67 g, brown solid), yield: 111%.

MS m/z (ESI): 189.0 [M+1]

Step 4

(5-Amino-1-(2-cyclopropyl-1H-benzo[d]imidazol-5-yl)-1H-pyrazol-4-yl)(1-(phenylsulfonyl)-1H-indol-2-yl)methanone 2-Cyclopropyl-5-hydrazinyl-1H-benzo[d]imidazole 1e (540 mg, 2.06 mmol) and 3-(dimethylamino)-2-(1-(phenylsulfonyl)-1H-indole-2-carbonyl)acrylonitrile 1f (581 mg, 1.53 mmol, prepared according to the published patent application CN102574836A) were suspended in 30 mL of absolute ethanol, the reaction solution was refluxed for 6 hours. The reaction solution was cooled down to room temperature, solid precipitated. The solution was subjected to suction filtration, the filter cake was washed with 5 mL of ethanol and then subjected to infrared drying to obtain (5-amino-1-(2-cyclopropyl-1H-benzo[d]imidazol-5-yl)-1H-pyrazol-4-yl)(1-(phenylsulfonyl)-1H-indol-2-yl)methanone 1 g (675 mg, tan solid), yield 67%.

MS m/z (ESI): 522.8 [M+1]

Step 5

(5-Amino-1-(2-cyclopropyl-1H-benzo[d]imidazol-5-yl)-1H-pyrazol-4-yl)(1H-indol-2-yl) methanone (5-Amino-1-(2-cyclopropyl-1H-benzo[d]imidazol-5-yl)-1H-pyrazol-4-yl)(1-(phenylsulfonyl)-1H-indol-2-yl)methanone 1 g (675 mg, 1.29 mmol) was dissolved in 5 mL of absolute ethanol, 3 mL of sodium hydroxide solution (4M, 12 mmol) was added dropwise, and the reaction solution was stirred overnight at room temperature. The reaction solution was concentrated under reduced pressure to remove ethanol, the residue was diluted with ice, stirred until the ice was dissolved, solid precipitated. The solution was subjected to suction filtration, the filter cake was washed with 50 mL of water and subjected to infrared drying to obtain crude product (LC-MS purity: 95.09%), the crude product was further pulped with hot ethanol (70° C.), the pulp was filtered to obtain (5-amino-1-(2-cyclopropyl-1H-benzo[d]imidazol-5-yl)-1H-pyrazol-4-yl)(1H-indol-2-yl)methanone 1 (150 mg, light yellow solid, HPLC purity: 98.62%), yield: 30.6%.

MS m/z (ESI): 383.0 [M+1]

$^1$H NMR (400 MHz, DMSO) δ 12.51 (s, 1H), 11.70 (s, 1H), 8.31 (s, 1H), 7.70 (d, J=7.9 Hz, 1H), 7.60 (s, 1H), 7.54 (s, 1H), 7.48 (d, J=8.1 Hz, 1H), 7.45 (s, 1H), 7.25 (t, J=9.4 Hz, 2H), 7.08 (t, J=7.4 Hz, 1H), 7.00 (d, J=17.0 Hz, 2H), 2.16 (s, 1H), 1.07 (dd, J=19.4, 9.6 Hz, 4H).

Example 2

Sodium 5-(5-amino-4-(1H-indole-2-carbonyl)-1H-pyrazol-1-yl)-1H-benzo[d]imidazole-2-carboxylate

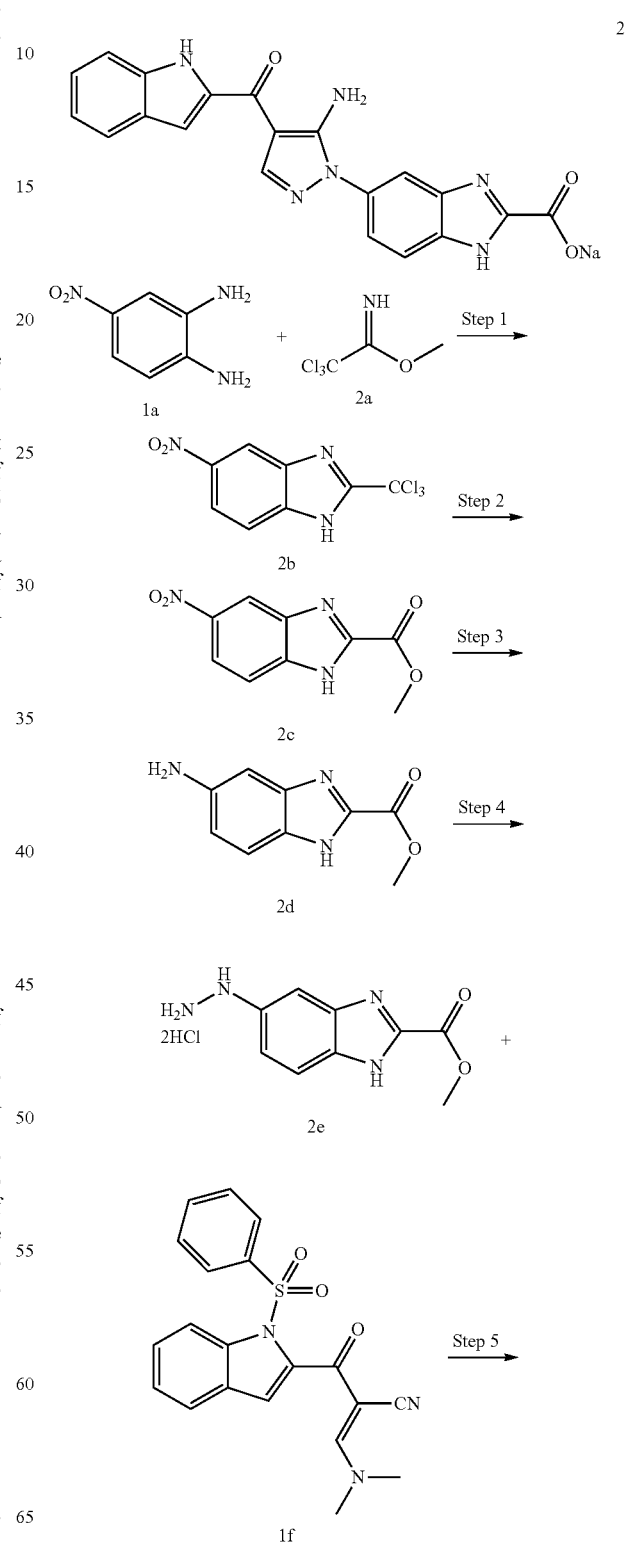

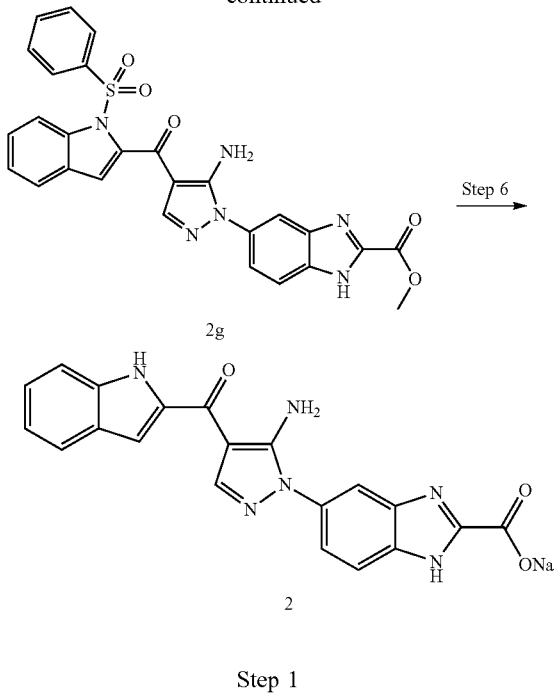

Step 1

5-Nitro-2-(trichloromethyl)-1H-benzo[d]imidazole

4-Nitrobenzene-1,2-diamine 1a (19.33 g, 126 mmol) was suspended in 200 mL of glacial acetic acid, methyl 2,2,2-trichloroacetimidate 2a (24.5 g, 139 mmol) was added dropwise. The mixture was stirred at room temperature until a large amount of solid precipitated. The reaction solution was diluted with 200 mL of glacial acetic acid, and then 500 g of crushed ice and 100 mL of ice water were added, stirred until the ice dissolved. The solution was subjected to suction filtration. The filter cake was washed with water (20 mL×5) and subjected to infrared drying to obtain 5-nitro-2-(trichloromethyl)-1H-benzo[d]imidazole 2b (27 g, yellow solid), yield: 69%.

MS m/z (ESI): 281.8 [M+1]

Step 2

Methyl 5-nitro-1H-benzo[d]imidazole-2-carboxylate

5-Nitro-2-(trichloromethyl)-1H-benzo[d]imidazole 2b (5 g, 17.83 mmol) and sodium carbonate (2.89 g, 29.83 mmol) were suspended in 200 mL of methanol. The reaction solution was heated to reflux for 4 hours, then sodium bicarbonate (1 g, 12 mmol) was added, the mixture was heated to reflux continuously for 4 hours. The reaction solution was concentrated under reduced pressure, 1M hydrochloric acid was added to the residue, solid precipitated, the residue was subjected to suction filtration, the filter cake was washed with water (20 mL×5) and then subjected to infrared drying to obtain methyl 5-nitro-1H-benzo[d]imidazole-2-carboxylate 2c (3.6 g, brown solid), yield: 91%.

MS m/z (ESI): 221.9 [M+1]

Step 3

Methyl 5-amino-1H-benzo[d]imidazole-2-carboxylate

Methyl 5-nitro-1H-benzo[d]imidazole-2-carboxylate 2c (1.5 g, 6.8 mmol) was suspended in 50 mL of methanol, 10% palladium/carbon (150 mg) was added, the mixture was stirred overnight at room temperature under hydrogen atmosphere. The mixture was filtered through diatomite, and washed with 5 mL of methanol, the filtrate was concentrated under reduced pressure to obtain methyl 5-amino-1H-benzo[d]imidazole-2-carboxylate 2d (1.015 g, brown oily liquid), yield: 78%.

MS m/z (ESI): 191.9 [M+1]

Step 4

Methyl 5-hydrazinyl-1H-benzo[d]imidazole-2-carboxylate dihydrochloride

Methyl 5-amino-1H-benzo[d]imidazol-2-carboxylate 2d (1 g, 5.23 mmol) was dissolved in 10 mL of concentrated hydrochloric acid, the solution was cooled down to 0° C. in an ice bath, 1 mL of sodium nitrite (398 mg, 5.77 mmol) solution was added dropwise. After the completion of the dropwise addition, the reaction solution was cooled down to 0° C. After 20 minutes of reaction, 1 mL of solution of stannous chloride dihydrate (2.61 g, 11.55 mmol) in concentrated hydrochloric acid was added dropwise, and the reaction solution continued to react at 0° C. for 0.5 hour. The reaction solution was subjected to suction filtration under reduced pressure, the filter cake was subjected to infrared drying to obtain methyl 5-hydrazinyl-1H-benzo[d]imidazole-2-carboxylate dihydrochloride 2e (987 mg, yellow solid), yield: 68%.

MS m/z (ESI): 206.9 [M+1]

Step 5

Methyl 5-(5-amino-4-(1-(phenylsulfonyl)-1H-indole-2-carbonyl)-1H-pyrazol-1-yl)-1H-benzo[d]imidazol-2-carboxylate Methyl 5-hydrazinyl-1H-benzo[d]imidazole-2-carboxylate dihydrochloride 2e (300 mg, 1.07 mmol) and 3-(dimethylamino)-2-(1-(phenylsulfonyl)-1H-indole-2-carbonyl) acrylonitrile 1f (408 mg, 1.07 mmol) were suspended in 30 mL of absolute ethanol and the reaction solution was refluxed for 6 hours. The solution was subjected to suction filtration, the filter cake was washed with 5 mL of ethanol, and the filtrate was concentrated under reduced pressure. The residue was further separated and purified by silica gel column chromatography (developing agent: system B) to obtain methyl 5-(5-amino-4-(1-(phenylsulfonyl)-1H-indole-2-carbonyl)-1H-pyrazol-1-yl)-1H-benzo[d]imidazol-2-carboxylate 2 g (143 mg, yellow solid), yield: 24%.

MS m/z (ESI): 540.7 [M+1]

Step 6

Sodium 5-(5-amino-4-(1H-indole-2-carbonyl)-1H-pyrazol-1-yl)-1H-benzo[d]imidazole-2-carboxylate Methyl 5-(5-amino-4-(1-(phenylsulfonyl)-1H-indole-2-carbonyl)-1H-pyrazol-1-yl)-1H-benzo[d]imidazol-2-carboxylate 2 g (143 mg, 258 mmol) was dissolved in 5 mL of absolute ethanol, 3 mL of sodium hydroxide solution (4M, 12 mmol) was added dropwise, the reaction solution was stirred overnight at room temperature. The reaction solution was concentrated under reduced pressure to remove ethanol, the residue was diluted with ice, the diluted solution was stirred until the ice was dissolved, solid precipitated. The solution was subjected to suction filtration, the filter cake was washed with 50 mL of water and subjected to infrared drying to obtain sodium 5-(5-amino-4-(1H-indole-2-carbonyl)-1H-pyrazol-1-yl)-1H-benzo[d]imidazole-2-carboxylate 2 (51.83 mg, off-white solid), yield: 49%.

MS m/z (ESI): 386.9 [M-Na+]

$^1$H NMR (400 MHz, DMSO) δ 13.03 (s, 1H), 11.72 (s, 1H), 8.34 (s, 1H), 8.16 (s, 1H), 7.70 (d, J=8.1 Hz, 1H), 7.60 (s, 1H), 7.54-7.32 (m, 3H), 7.32-7.17 (m, 2H), 7.17-6.99 (m, 2H).

Example 3

(5-Amino-1-(2-amino-1H-benzo[d]imidazol-5-yl)-1H-pyrazol-4-yl)(1H-indol-2-yl) methanone

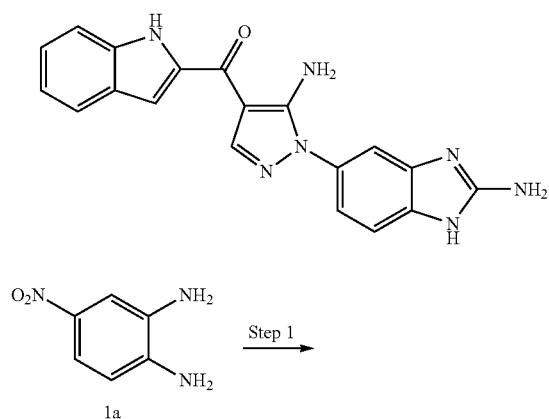

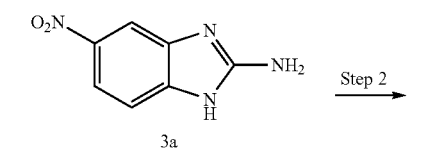

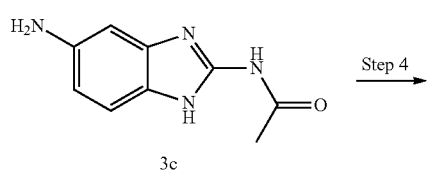

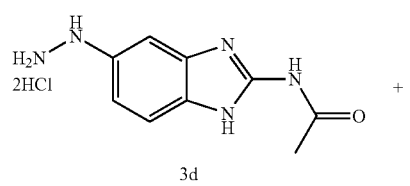

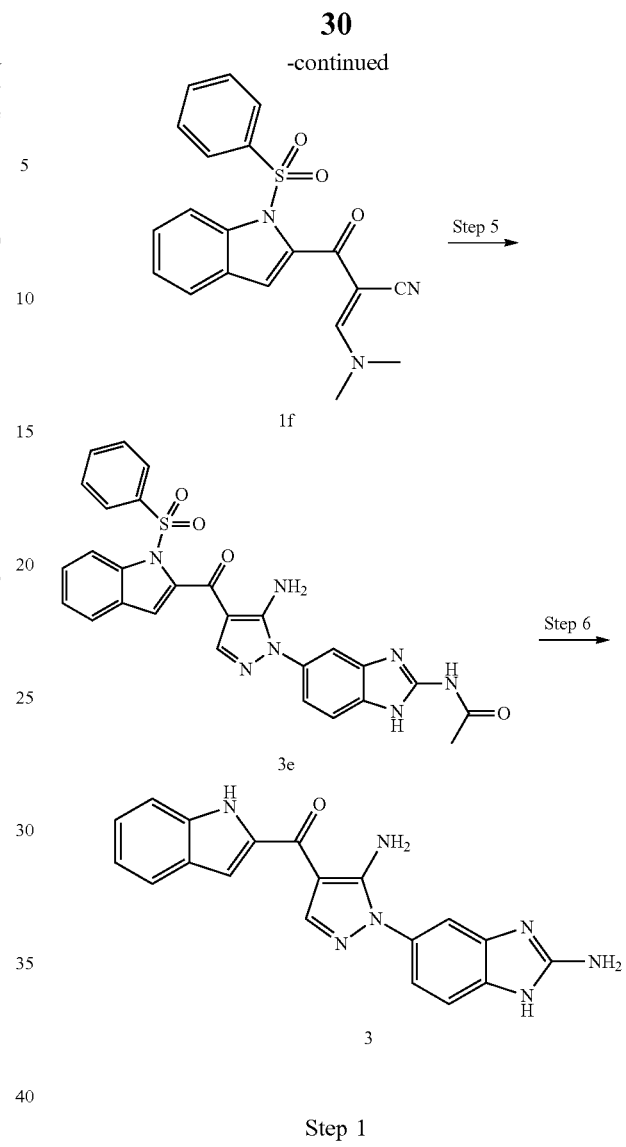

Step 1

5-Nitro-1H-benzo[d]imidazol-2-amine

4-Nitrobenzene-1,2-diamine 1a (5.06 g, 33 mmol) was suspended in 90 mL of a mixed solvent of acetonitrile and water (V/V=1:8), and bromoacetonitrile (3.55 g, 33.5 mmol) was added under stirring, the reaction solution was heated to reflux for 4 hours. The reaction solution was cooled down to room temperature, the pH was adjusted to alkaline with aqueous ammonia, yellow solid precipitated. The solution was subjected to suction filtration, the filter cake was washed with water (20 mL×5) and subjected to infrared drying to obtain 5-nitro-1H-benzo[d]imidazol-2-amine 3a (5.65 g, orange solid), yield: 96%.

MS m/z (ESI): 178.9 [M+1]

Step 2

N-(5-Nitro-1H-benzo[d]imidazol-2-yl)acetamide

5-Nitro-1H-benzo[d]imidazol-2-amine 3a (5.1 g, 28.63 mmol) was suspended in 50 mL of pyridine, acetic anhydride (6.21 g, 60.88 mmol) was added dropwise, the reaction solution was heated to 60° C., 6 g of acetic anhydride was added, the mixture was stirred for 72 hours. The reaction solution was poured into crushed ice, solid precipitated, the solution was subjected to suction filtration, the filter cake was washed with water (20 mL×5) then was subjected to infrared drying to obtain N-(5-nitro-1H-benzo[d]imidazol-2-yl)acetamide 3b (4.2 g, yellow solid), yield: 67%.

MS m/z (ESI): 220.9 [M+1]

Step 3

N-(5-Amino-1H-benzo[d]imidazol-2-yl)acetamide

N-(5-Nitro-1H-benzo[d]imidazol-2-yl)acetamide 3b (1.5 g, 6.81 mmol) was suspended in 50 mL of methanol, 10% palladium/carbon (150 mg) was added, the mixture was stirred overnight at room temperature under hydrogen atmosphere and filtered with diatomite. The filter cake was washed with a mixed solvent of dichloromethane and methanol (10 mL×3), the filtrate was concentrated under reduced pressure. 50 mL of methanol was added into the residue, the mixture was pulped and subjected to suction filtration, the filter cake was washed with 5 mL of methanol then subjected to infrared drying accordingly to obtain N-(5-amino-1H-benzo[d]imidazol-2-yl)acetamide 3c (1.1 g, brown solid), yield: 85%.

MS m/z (ESI): 191.0 [M+1]

Step 4

N-(5-Hydrazinyl-1H-benzo[d]imidazol-2-yl)acetamide dihydrochloride

N-(5-Amino-1H-benzo[d]imidazol-2-yl)acetamide 3c (1 g, 5.26 mmol) was dissolved in 10 mL of concentrated hydrochloric acid, cooled down to 0° C. in an ice bath, 1 mL of sodium nitrite (363 mg, 5.26 mmol) solution was added dropwise. The reaction solution was cooled down to 0° C., after 20 minutes of reaction, 1 mL of solution of stannous chloride dihydrate (2.37 g, 10.52 mmol) in concentrated hydrochloric acid was added dropwise, the reaction solution continued to react at 0° C. for 0.5 hour. The reaction solution was concentrated under reduced pressure, the residue was subjected to infrared drying to obtain N-(5-hydrazinyl-1H-benzo[d]imidazol-2-yl)acetamide dihydrochloride 3d (1.49 g, brown solid), yield: 98%.

MS m/z (ESI): 206.9 [M+1]

Step 5

N-(5-(5-Amino-4-(1-(phenylsulfonyl)-1H-indole-2-carbonyl)-1H-pyrazol-1-yl)-1H-benzo[d]imidazol-2-yl)acetamide N-(5-Hydrazinyl-1H-benzo[d]imidazol-2-yl)acetamide dihydrochloride 3d (500 mg, 1.8 mmol) and 3-(dimethylamino)-2-(1-(phenylsulfonyl)-1H-indole-2-carbonyl)acrylonitrile 1f (477 mg, 1.26 mmol) were suspended in 20 mL of absolute ethanol, the reaction solution was refluxed for 4 hours. The solution was subjected to suction filtration, the filter cake was washed with 5 mL of ethanol then the filtrate was concentrated under reduced pressure. The residue was further separated and purified by silica gel column chromatography (developing agent: system B) to obtain N-(5-(5-amino-4-(1-(phenylsulfonyl)-1H-indole-2-carbonyl)-1H-pyrazol-1-yl)-1H-benzo[d]imidazol-2-yl) acetamide 3e (134 mg, brown solid), yield: 13.8%.

MS m/z (ESI): 539.8 [M+1]

Step 6

(5-Amino-1-(2-amino-1H-benzo[d]imidazol-5-yl)-1H-pyrazol-4-yl)(1H-indol-2-yl) methanone N-(5-(5-Amino-4-(1-(phenylsulfonyl)-1H-indole-2-carbonyl)-1H-pyrazol-1-yl)-1H-benzo[d]imidazol-2-yl) acetamide 3e (526 mg, 0.98 mmol) was dissolved in 10 mL of absolute ethanol, and 3 mL of sodium hydroxide solution (4M, 12 mmol) was added dropwise, the reaction solution was stirred overnight at room temperature. The reaction solution was concentrated under reduced pressure to remove ethanol, the residue was diluted with ice, stirred until the ice was dissolved, solid precipitated. The mixture was subjected to suction filtration, the filter cake was washed with 50 mL of water and subjected to infrared drying to obtain (5-amino-1-(2-amino-1H-benzo[d]imidazol-5-yl)-1H-pyrazol-4-yl) (1H-indol-2-yl)methanone 3 (186 mg, brown solid), yield: 53%.

MS m/z (ESI): 357.9 [M+1]

$^1$H NMR (400 MHz, DMSO) δ 11.69 (s, 1H), 10.92 (s, 1H), 8.27 (s, 1H), 7.69 (s, 1H), 7.44 (d, J=8.1 Hz, 1H), 7.42 (s, 1H), 7.40-7.13 (m, 3H), 7.07 (s, 2H), 6.89 (s, 2H), 6.36 (s, 2H).

Example 4

N-(5-(5-Amino-4-(1H-indole-2-carbonyl)-1H-pyrazol-1-yl)-1H-benzo[d]imidazol-2-yl) acetamide

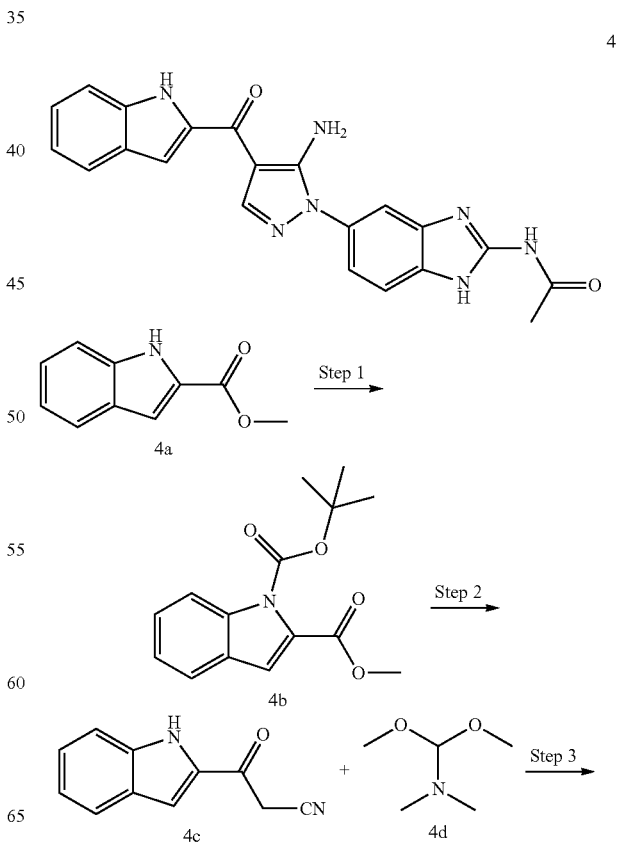

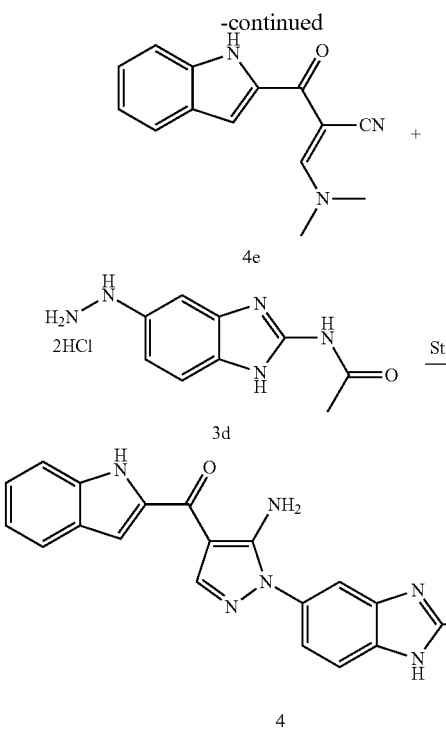

tem B) to obtain 3-(1H-Indol-2-yl)-3-oxopropanenitrile 4c (482 mg, pink solid), yield: 76%.

MS m/z (ESI): 206.9 [M+Na]

Step 3

3-(Dimethylamino)-2-(1H-indole-2-carbonyl)acrylonitrile 3-(1H-Indol-2-yl)-3-oxopropanenitrile 4c (380 mg, 2.06 mmol) was dissolved in dry tetrahydrofuran, the solution of 1,1-dimethoxy-N,N-dimethylmethanamine 4d (246 mg, 2.06 mmol) in tetrahydrofuran was added, after the completion of the addition, yellow solid precipitated. The solvent was concentrated under reduced pressure to obtain 3-(dimethylamino)-2-(1H-indole-2-carbonyl)acrylonitrile 4e (490 mg, yellow solid), yield: 99%. The product was directly used in the next step of reaction without purification.

MS m/z (ESI): 239.9 [M+1]

Step 4

N-(5-(5-Amino-4-(1H-indole-2-carbonyl)-1H-pyrazol-1-yl)-1H-benzo[d]imidazol-2-yl) acetamide 3-(Dimethylamino)-2-(1H-indole-2-carbonyl)acrylonitrile 4e (617 mg, 2.22 mmol) and N-(5-hydrazinyl-1H-benzo[d]imidazol-2-yl)acetamide dihydrochloride 3d (372 mg, 1.55 mmol) were suspended in 20 mL of absolute ethanol, pyridine (351 mg, 4.44 mmol) was added, the reaction solution was heated to reflux for 8 hours. The reaction solution was subjected to suction filtration under reduced pressure, the filter cake was further separated and purified by silica gel column chromatography (developing agent: system A) to obtain N-(5-(5-amino-4-(1H-indole-2-carbonyl)-1H-pyrazol-1-yl)-1H-benzo[d]imidazol-2-yl)acetamide 4 (94 mg, yellow solid), yield: 11%.

MS m/z (ESI): 399.9 [M+1]

$^1$H NMR (400 MHz, DMSO) δ 11.70 (s, 1H), 8.93 (s, 1H), 8.58 (s, 1H), 8.34 (s, 1H), 8.06 (s, 1H), 7.73 (d, J=34.3 Hz, 3H), 7.61-7.39 (m, 2H), 7.24 (s, 1H), 7.07 (s, 1H), 2.30 (s, 3H).

Example 5

(5-Amino-1-(1H-benzo[d][1,2,3]triazol-5-yl)-1H-pyrazol-4-yl)(1H-indol-2-yl)methanone

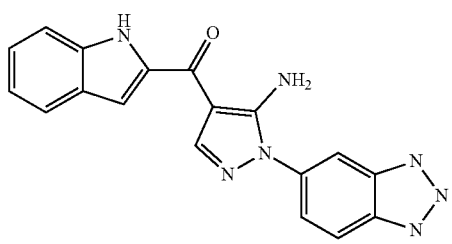

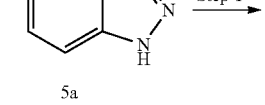

Step 1

1-Tert-butyl 2-methyl 1H-indole-1,2-dicarboxylate

Methyl 1H-indole-2-carboxylate 4a (5 g, 26.4 mmol) and 4-dimethylaminopyridine (3.55 g, 29 mmol) were dissolved in acetonitrile and di-tert-butyl dicarbonate (6.92 g, 31.71 mmol) was added dropwise at room temperature, the solution was stirred at room temperature for 1 hour. The reaction solution was concentrated under reduced pressure, the residue was further separated and purified by silica gel column chromatography (developing agent: system A) to obtain 1-tert-butyl 2-methyl-1H-indole-1,2-dicarboxylate 4b (7.6 g, colorless oily liquid), yield: 99.5%.

MS m/z (ESI): 312.0 [M+Na]

Step 2

3-(1H-Indol-2-yl)-3-oxopropanenitrile

1-Tert-butyl 2-methyl-1H-indole-1,2-dicarboxylate 4b (1 g, 3.46 mmol) and acetonitrile (784 mg, 19.1 mmol) were dissolved in dry tetrahydrofuran. The reaction solution was cooled down to −78° C. with liquid nitrogen, lithium hexamethyldisilazide solution (1M, 14.26 mL) was added dropwise, the reaction solution was kept at −78° C. and continued to react for 2 hours. The reaction solution was heated to room temperature and was stirred overnight. The reaction solution was quenched with saturated ammonium chloride solution, 50 mL of water was added, the resulting solution was extracted with ethyl acetate (30 mL×2). The combined organic phases were washed with saturated sodium chloride solution (30 mL×2), dried over anhydrous sodium sulfate, filtered, and the filtrate was concentrated under reduced pressure. The residue was further separated and purified by silica gel column chromatography (developing agent: sys-

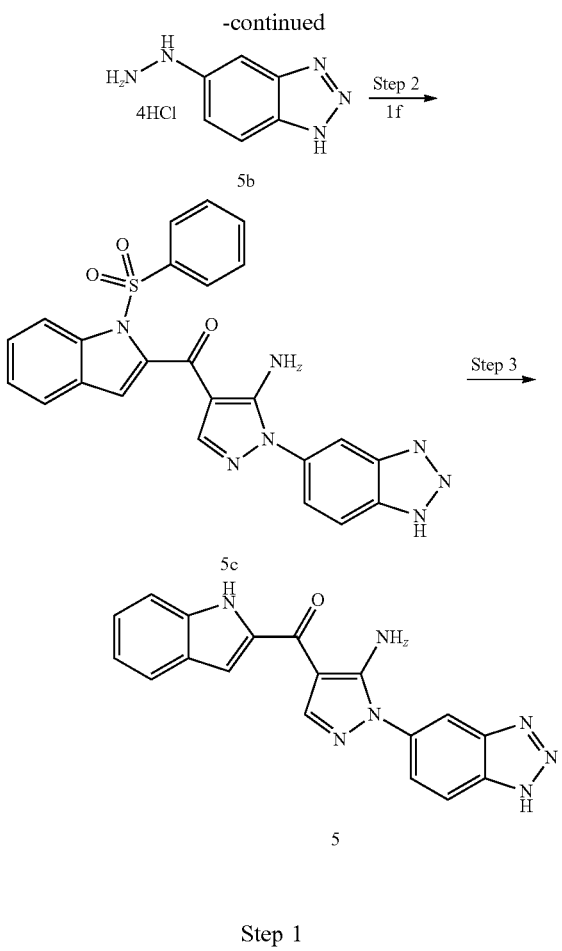

Step 1

5-Hydrazinyl-1H-benzo[d][1,2,3]triazole tetrachloride

1H-Benzo[d][1,2,3]triazol-5-amine 5a (800 mg, 5.96 mmol) was suspended in 10 mL of concentrated hydrochloric acid, the solution was cooled down to −5° C. to 0° C. in an ice bath, 1 mL of sodium nitrite (411 mg, 5.96 mmol) solution was added dropwise. The reaction solution was cooled down to −5° C. to 0° C. After 20 minutes of reaction, 1 mL of solution of stannous chloride dihydrate (2.69 g, 11.93 mmol) in concentrated hydrochloric acid was added dropwise, the reaction solution continued to react at 0° C. continuously for 0.5 hour. The solution was subjected to suction filtration, the filter cake was subjected for infrared drying to obtain 5-hydrazinyl-1H-benzo[d][1,2,3]triazole tetrachloride 5b (1.7 g, brick red solid), yield: 99%.

MS m/z (ESI): 150.0 [M+1]

Step 2

(5-Amino-1-(1H-benzo[d][1,2,3]triazol-5-yl)-1H-pyrazol-4-yl)(1-(phenylsulfonyl)-1H-indol-2-yl)methanone 5-Hydrazinyl-1H-benzo[d][1,2,3]triazole tetrachloride 5b (583 mg, 1.98 mmol) and 3-(dimethylamino)-2-(1-(phenylsulfonyl)-1H-indole-2-carbonyl)acrylonitrile 1f (550 mg, 1.45 mmol) were suspended in 30 mL of absolute ethanol, the reaction solution was heated to reflux for 4 hours. The reaction solution was diluted with 100 mL of ethyl acetate, washed with saturated sodium bicarbonate solution (20 mL) and then saturated sodium chloride solution (20 mL), dried over anhydrous sodium sulfate, filtered and concentrated under reduced pressure to obtain (5-amino-1-(1H-benzo[d][1,2,3]triazol-5-yl)-1H-pyrazol-4-yl)(1-(phenylsulfonyl)-1H-indol-2-yl)methanone 5c (555 mg, brown solid), yield: 89%.

MS m/z (ESI): 483.8 [M+1]

Step 3

(5-Amino-1-(1H-benzo[d][1,2,3]triazol-5-yl)-1H-pyrazol-4-yl)(1H-indol-2-yl)methanone (5-Amino-1-(1H-benzo[d][1,2,3]triazol-5-yl)-1H-pyrazol-4-yl)(1-(phenylsulfonyl)-1H-indol-2-yl)methanone 5c (550 mg, 1.14 mmol) was dissolved in 15 mL of absolute ethanol, sodium hydroxide solution (4M, 3 mL) was added, the solution was stirred overnight at room temperature. The reaction solution was poured into crushed ice, stirred until the ice was dissolved, the pH was adjusted to acidic with concentrated hydrochloric acid, solid precipitated. The solution was subjected to suction filtration, the filter cake was subjected to infrared drying, and was further separated and purified with silica gel column chromatography (developing agent: system B) to obtain (5-amino-1-(1H-benzo[d][1,2,3]triazol-5-yl)-1H-pyrazol-4-yl)(1H-indol-2-yl)methanone 5 (238 mg, yellow solid), yield: 61%.

MS m/z (ESI): 343.9 [M+1]

$^1$H NMR (400 MHz, DMSO) δ 16.01 (s, 1H), 11.72 (s, 1H), 8.39 (s, 1H), 8.12 (s, 2H), 7.71 (d, J=7.9 Hz, 1H), 7.66 (d, J=8.0 Hz, 1H), 7.49 (d, J=8.5 Hz, 2H), 7.27 (d, J=8.1 Hz, 3H), 7.09 (t, J=7.5 Hz, 1H).

Example 6

(5-Amino-1-(2-(dimethylamino)-1H-benzo[d]imidazol-5-yl)-1H-pyrazol-4-yl)(1H-indol-2-yl)methanone

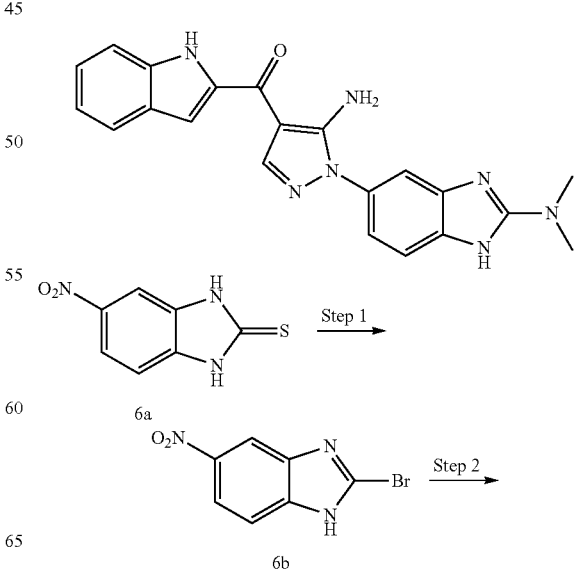

-continued

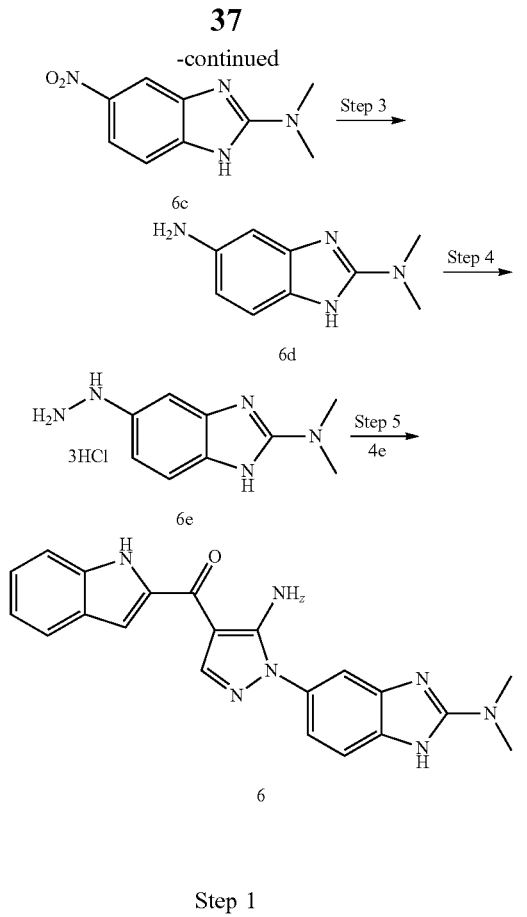

Step 1

2-Bromo-5-nitro-1H-benzo[d]imidazole

5-Nitro-1H-benzo[d]imidazol-2(3H)-thione 6a (9 g, 46 mmol, prepared according to E.J.M.C, 2013, 63:696) was suspended in 100 mL of glacial acetic acid, 1 mL of concentrated hydrobromic acid (48% wt. aqueous solution) was added, and bromine water (8.11 g, 51 mmol) was added dropwise, the reaction solution was reacted at room temperature for 6 hours. The reaction solution was poured into crushed ice and was stirred until the ice dissolved. The solution was subjected to suction filtration, the filter cake was washed with water (30 mL×2), then subjected to infrared drying. The obtained crude product was further separated and purified by silica gel column chromatography (developing agent: system B) to obtain 2-bromo-5-nitro-1H-benzo[d]imidazole 6b (1.65 g, brown solid), yield: 15%.

MS m/z (ESI): 241.7 [M+1]

Step 2

N, N-Dimethyl-5-nitro-1H-benzo[d]imidazol-2-amine

2-Bromo-5-nitro-1H-benzo[d]imidazole 6b (1.65 g, 6.82 mmol) was dissolved in 1M solution of dimethylamine (10 mL, 10 mmol) in tetrahydrofuran, the mixture was subjected to microwave reaction at 115° C. for 1 hour, then was concentrated under reduced pressure to obtain N, N-dimethyl-5-nitro-1H-benzo[d]imidazol-2-amine 6c (1.17 g, brown solid), yield: 83%.

MS m/z (ESI): 206.9 [M+1]

Step 3

N2, N2-Dimethyl-1H-benzo[d]imidazol-2,5-diamine 3 mL of N, N-Dimethyl-5-nitro-1H-benzo[d]imidazol-2-amine 6c (1.17 g, 4.8 mmol) was dissolved in 20 mL of anhydrous methanol, 10% palladium/carbon (110 mg) was added, under hydrogen atmosphere, the mixture was reacted at room temperature for 8 hours. The mixture was subjected to suction filtration, the filter cake was washed with methanol (10 mL×3), the filtrate was concentrated under reduced pressure to obtain N2, N2-dimethyl-1H-benzo[d]imidazol-2,5-diamine 6d (533 mg, black solid), yield: 44%.

MS m/z (ESI): 177.0 [M+1]

Step 4

5-Hydrazinyl-N, N-dimethyl-1H-benzo[d]imidazol-2-amine trihydrochloride

N2, N2-Dimethyl-1H-benzo[d]imidazol-2,5-diamine 6d (300 mg, 1.7 mmol) was dissolved in 10 mL of concentrated hydrochloric acid, cooled down to 0° C. in an ice bath, 1 mL sodium nitrate (117 mg, 1.7 mmol) solution was added dropwise. The reaction solution was cooled down to 0° C. After 20 minutes of reaction, 1 mL of solution of stannous chloride dihydrate (768 mg, 3.4 mmol) in concentrated hydrochloric acid was added dropwise, the reaction solution continued to react at 0° C. for 1 hour. The reaction solution was concentrated under reduced pressure, the residue was subjected to infrared drying to obtain 5-hydrazinyl-N, N-dimethyl-1H-benzo[d]imidazol-2-amine trihydrochloride 6e (188 mg, yellow green solid), yield: 37%.

MS m/z (ESI): 192.0 [M+1]

Step 5

(5-Amino-1-(2-(dimethylamino)-1H-benzo[d]imidazol-5-yl)-1H-pyrazol-4-yl)(1H-indol-2-yl)methanone 5-Hydrazinyl-N, N-dimethyl-1H-benzo[d]imidazol-2-amine trihydrochloride 6e (160 mg, 0.53 mmol) and 3-(dimethylamino)-2-(1H-indole-2-carbonyl)acrylonitrile 4e (102 mg, 0.43 mmol) were suspended in 20 mL of absolute ethanol, the reaction solution was heated to reflux for 4 hours. The reaction solution was concentrated under reduced pressure, and the residue was further separated and purified by silica gel column chromatography (developing agent: system A) to obtain (5-amino-1-(2-(dimethylamino)-1H-benzo[d]imidazol-5-yl)-1H-pyrazol-4-yl)(1H-indol-2-yl)methanone 6 (46 mg, yellow solid), yield: 28%.

MS m/z (ESI): 386.9 [M+1]

$^1$H NMR (400 MHz, DMSO) δ 13.57 (s, 2H), 11.71 (s, 1H), 8.35 (s, 1H), 7.70 (d, J=8.0 Hz, 1H), 7.55 (d, J=7.6 Hz, 2H), 7.49 (d, J=8.2 Hz, 1H), 7.44 (d, J=11.2 Hz, 2H), 7.26 (t, J=7.6 Hz, 1H), 7.12 (s, 1H), 7.11-7.05 (m, 1H), 3.28 (s, 6H).

Example 7

Methyl 5-(5-amino-4-(1H-indole-2-carbonyl)-1H-pyrazol-1-yl)-1H-benzo[d]imidazole-2-carboxylate

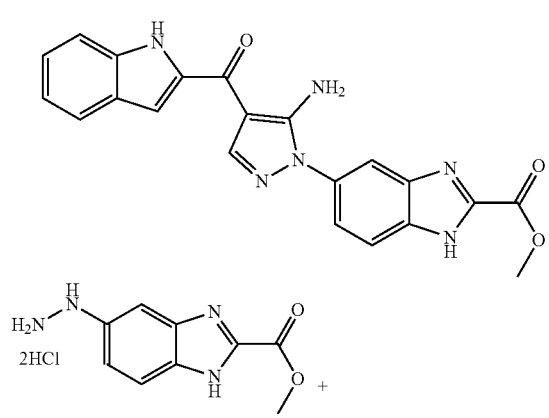

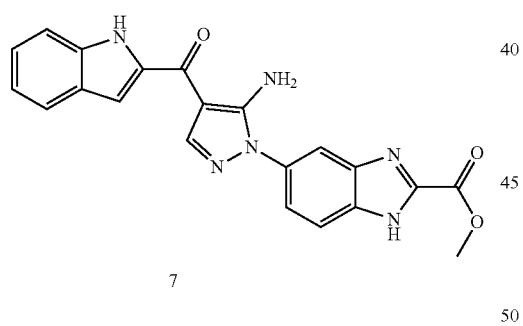

3-(Dimethylamino)-2-(1H-indole-2-carbonyl)acrylonitrile 4e (343 mg, 1.43 mmol), methyl 5-hydrazinyl-1H-benzo[d]imidazole-2-carboxylate dihydrochloride 2e (500 mg, 1.79 mmol) and pyridine (425 mg, 5.37 mmol) were suspended in 50 mL of methanol, the reaction solution was heated to reflux for 8 hours. The reaction solution was concentrated under reduced pressure, the residue was further separated and purified by silica gel column chromatography (developing agent: system B) to obtain methyl 5-(5-amino-4-(1H-indole-2-carbonyl)-1H-pyrazol-1-yl)-1H-benzo[d]imidazole-2-carboxylate 7 (54 mg, yellow solid), yield: 9%.

MS m/z (ESI): 400.9 [M+1]

$^1$H NMR (400 MHz, DMSO) δ 13.80 (s, 1H), 11.72 (s, 1H), 8.36 (s, 1H), 7.96 (s, 1H), 7.70 (d, J=8.1 Hz, 2H), 7.62-7.43 (m, 3H), 7.26 (t, J=7.3 Hz, 1H), 7.11 (dd, J=25.8, 18.0 Hz, 3H), 3.98 (s, 3H).

Example 8

5-(5-Amino-4-(1H-indole-2-carbonyl)-1H-pyrazol-1-yl)-N-methyl-1H-benzo[d]imidazole-2-carboxamide

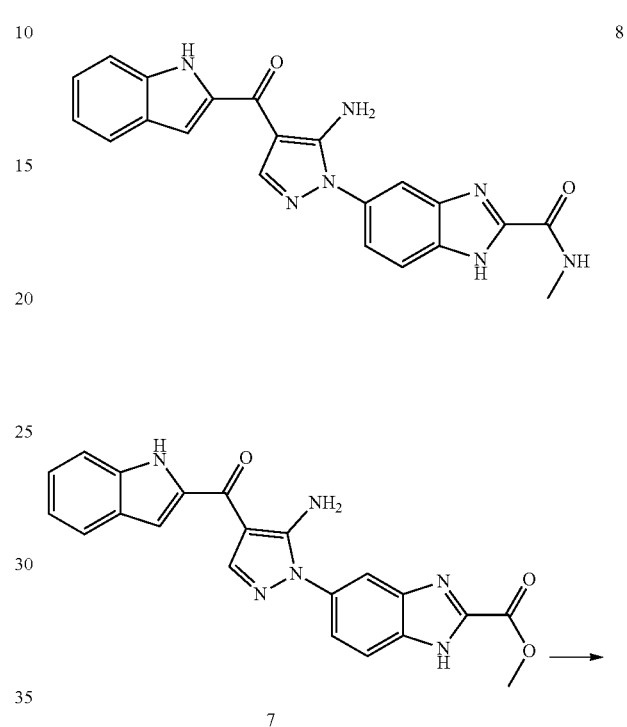

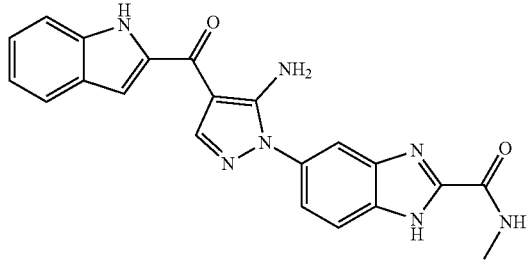

Methyl 5-(5-amino-4-(1H-indole-2-carbonyl)-1H-pyrazol-1-yl)-1H-benzo[d]imidazole-2-carboxylate 7 (58 mg, 0.144 mmol) was dissolved in 5 mL solution of methylamine in ethanol, the mixture was stirred at room temperature for 3 hours. The reaction solution was concentrated under reduced pressure to obtain 5-(5-amino-4-(1H-indole-2-carbonyl)-1H-pyrazol-1-yl)-N-methyl-1H-benzo[d]imidazole-2-carboxamide 8 (37 mg, yellow solid), yield: 64%.

MS m/z (ESI): 399.9 [M+1]

$^1$H NMR (400 MHz, DMSO) δ 11.71 (s, 1H), 9.04 (d, J=4.9 Hz, 1H), 8.35 (s, 1H), 7.79 (d, J=7.1 Hz, 2H), 7.70 (d, J=8.0 Hz, 1H), 7.54-7.44 (m, 3H), 7.26 (t, J=7.5 Hz, 1H), 7.16-7.05 (m, 3H), 2.86 (d, J=4.7 Hz, 3H).

Example 9

Ethyl 5-(5-Amino-4-(1H-indole-2-carbonyl)-1H-pyrazol-1-yl)-1H-benzo[d]imidazole-2-carboxylate

Example 10

(5-Amino-1-(2-(1-fluorocyclopropyl)-1H-benzo[d]imidazol-5-yl)-1H-pyrazol-4-yl)(1H-indol-2-yl)methanone

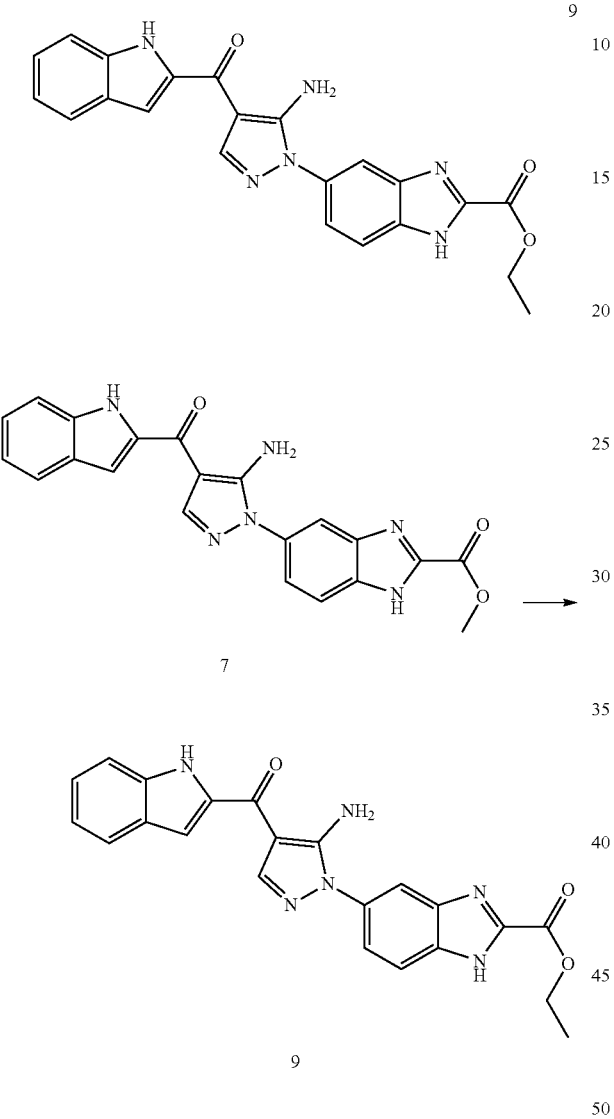

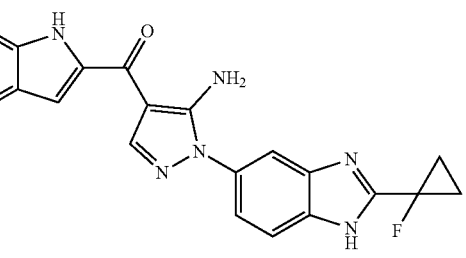

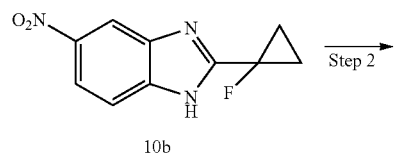

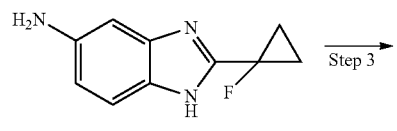

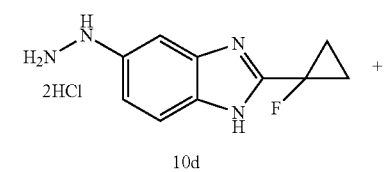

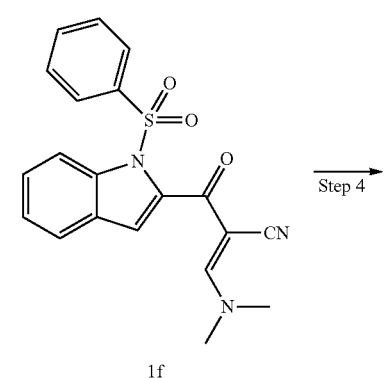

Methyl 5-(5-amino-4-(1H-indole-2-carbonyl)-1H-pyrazol-1-yl)-1H-benzo[d]imidazole-2-carboxylate 7 (210 mg, 0.524 mmol) was dissolved in 20 mL of absolute ethanol, sodium hydroxide (2.1 mg, 0.524 mmol) was added, and the mixture was stirred at room temperature for 5 minutes and then continued to be heated to reflux for 3 hours. The reaction solution was concentrated under reduced pressure, the crude product was purified by thin layer chromatography (developing agent: system B) to obtain ethyl 5-(5-amino-4-(1H-indole-2-carbonyl)-1H-pyrazol-1-yl)-1H-benzo[d]imidazole-2-carboxylate 9 (10 mg, white solid), yield: 4.7%.

MS m/z (ESI): 414.9 [M+1]

$^1$H NMR (400 MHz, MeOD) δ 8.33 (s, 1H), 7.98 (s, 1H), 7.83 (s, 1H), 7.74 (d, J=8.0 Hz, 1H), 7.62 (s, 1H), 7.50 (d, J=7.8 Hz, 1H), 7.40 (s, 1H), 7.29 (s, 1H), 7.11 (s, 1H), 4.54 (d, J=6.8 Hz, 2H), 1.49 (s, 3H).

-continued

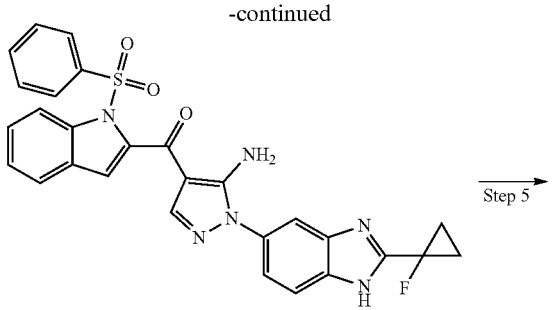

10e

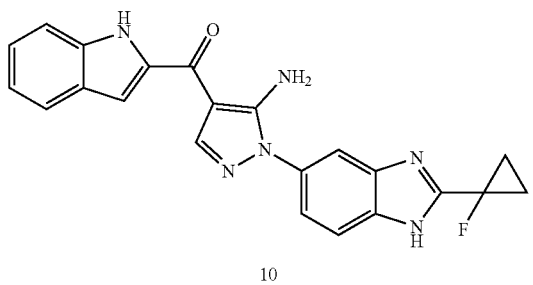 [SMILES: Nc1c(C(=O)c2cc3ccccc3[nH]2)cnn1-c1ccc2[nH]c(C3(F)CC3)nc2c1]

10

Step 1

2-(1-Fluorocyclopropyl)-5-nitro-1H-benzo[d]imidazole

4-Nitrobenzene-1,2-diamine 1a (750 mg, 7.90 mmol) and 1-fluorocyclopropane carboxylic acid 10a (510 mg, 4.90 mmol) was dissolved in polyphosphoric acid and the reaction solution was reacted at 110° C. for 4 hours. 50 mL of ice-water mixture was added to the reaction solution, the pH was adjusted to 7 to 8 with sodium hydroxide, white solid precipitated. The solution was subjected to suction filtration, the filter cake was subjected to infrared drying to obtain crude 2-(1-fluorocyclopropyl)-5-nitro-1H-benzo[d]imidazole 10b (553 mg, brown-red solid), yield: 51%.

Step 2

2-(1-Fluorocyclopropyl)-1H-benzo[d]imidazol-5-amine 2-(1-Fluorocyclopropyl)-5-nitro-1H-benzo[d]imidazole 10b (553 mg, 2.50 mmol) was dissolved in 200 mL of anhydrous methanol, 10% palladium/carbon was added under stirring (1.00 g), under hydrogen atmosphere, the mixture was reacted at room temperature for 4 hours. The mixture was filtered, the filtrate was concentrated under reduced pressure to obtain crude 2-(1-fluorocyclopropyl)-1H-benzo[d]imidazol-5-amine 10c (478 mg, dark green solid), the product was directly subjected to the next step of reaction without purification.

Step 3

2-(1-Fluorocyclopropyl)-5-hydrazinyl-1H-benzo[d]imidazole dihydrochloride 2-(1-Fluorocyclopropyl)-1H-benzo[d]imidazol-5-amine 10c (478 mg, 2.50 mmol) was suspended in 6 mL of hydrochloric acid, the reaction solution was cooled down to 0° C. in an ice bath, 0.5 mL of sodium nitrite (210 mg, 3.05 mmol) solution was added dropwise, the reaction solution was cooled down to 0° C. After 20 minutes of reaction, 0.6 mL of solution of stannous chloride dihydrate (1.55 g, 6.88 mmol) in concentrated hydrochloric acid was added dropwise, the reaction solution continued to react at 0° C. for 20 minutes. The reaction solution was filtered under reduced pressure, the filter cake was subjected to infrared drying to obtain crude 2-(1-fluorocyclopropyl)-5-hydrazinyl-1H-benzo[d]imidazole dihydrochloride 10d (706 mg, light purple solid), the product was directly subjected to the next step of reaction without purification.

MS m/z (ESI): 207.0 [M+1]

Step 4

(5-Amino-1-(2-(1-fluoropropyl)-1H-benzo[d]imidazol-5-yl)-1H-pyrazol-4-yl)(1-(phenylsulfonyl)-1H-indol-2-yl)methanone 2-(1-Fluorocyclopropyl)-5-hydrazinyl-1H-benzo[d]imidazole dihydrochloride 10d (706 mg, 2.53 mmol) and (E)-3-(dimethylamino)-2-(1-(phenylsulfonyl)-1H-indole-2-carbonyl)acrylonitrile 1f (959 mg, 2.53 mmol, prepared according to the published patent application CN102574836A) were suspended in 13 mL of absolute ethanol, the reaction solution was refluxed for 4 hours. The reaction solution was cooled down to room temperature, solid precipitated. The solution was subjected to suction filtration, the filter cake was washed with ethanol (15 mL×3) then was subjected to infrared drying to obtain (5-amino-1-(2-(1-fluoropropyl)-1H-benzo[d]imidazol-5-yl)-1H-pyrazol-4-yl)(1-(phenylsulfonyl)-1H-indol-2-yl)methanone 10e (493 mg, black solid), yield: 36%.

MS m/z (ESI): 540.8 [M+1]

Step 5

(5-Amino-1-(2-(1-fluorocyclopropyl)-1H-benzo[d]imidazol-5-yl)-1H-pyrazol-4-yl)(1H-indol-2-yl)methanone (5-Amino-1-(2-(1-fluorocyclopropyl)-1H-benzo[d]imidazol-5-yl)-1H-pyrazol-4-yl)(1-(phenylsulfonyl)-1H-indol-2-yl)methanone 10e (493 mg, 0.91 mmol) was dissolved in 30 mL of absolute ethanol, 8.7 mL of a sodium hydroxide solution (4M, 34.7 mmol) was added dropwise, the reaction solution was reacted at room temperature for 4 hours. The reaction solution was 50 concentrated under reduced pressure to remove ethanol, the residue was diluted with ice and stirred until the ice was dissolved, solid precipitated. The solution was subjected to suction filtration, the filter cake was washed with 50 mL of water, the obtained residue was purified with silica gel thin-layer chromatography (developing agent: system B) to obtain (5-amino-1-(2-(1-fluorocyclopropyl)-1H-benzo[d]imidazol-5-yl)-1H-pyrazol-4-yl)(1H-indol-2-yl)methanone 10 (92 mg, brown solid, HPLC purity: 94.58%), yield: 25%.

MS m/z (ESI): 400.9 [M+1]

$^1$H NMR (400 MHz, DMSO-d6) δ 13.15 (d, J=6.1 Hz, 1H), 11.69 (s, 1H), 8.32 (d, J=7.3 Hz, 1H), 7.75-7.68 (m, 2H), 7.64 (d, J=7.9 Hz, 1H), 7.51-7.43 (m, 2H), 7.38 (t, J=8.7 Hz, 1H), 7.25 (t, J=7.6 Hz, 1H), 7.06 (dd, J=22.0, 14.3 Hz, 3H), 1.68 (d, J=19.1 Hz, 2H), 1.45 (d, J=7.3 Hz, 2H).

Example 11

(5-amino-1-(2-cyclopropyl-1H-benzo[d]imidazol-5-yl)-1H-pyrazol-4-yl)(5-fluoro-1H-indol-2-yl)methanone

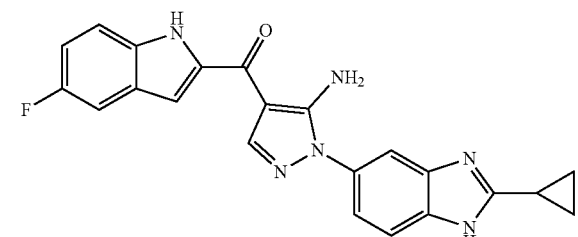

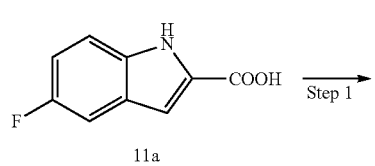
11a

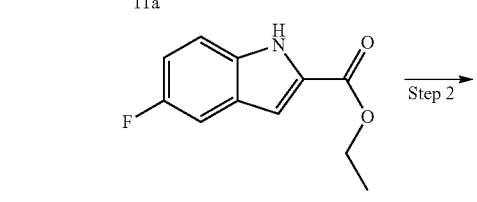
11b

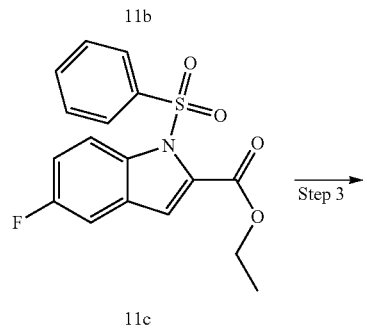
11c

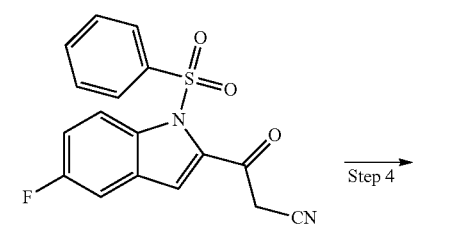
11d

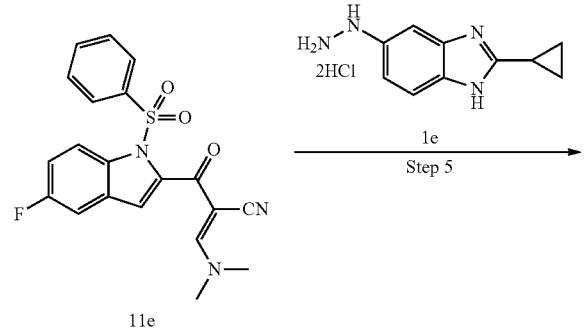
11e

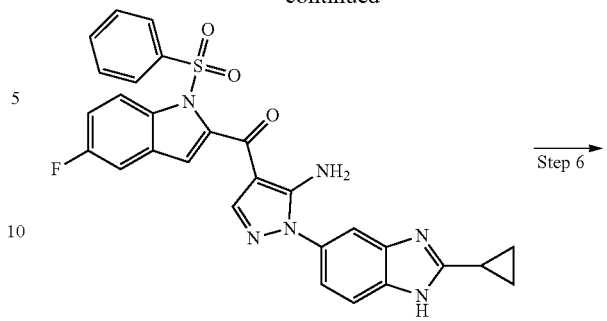
11f

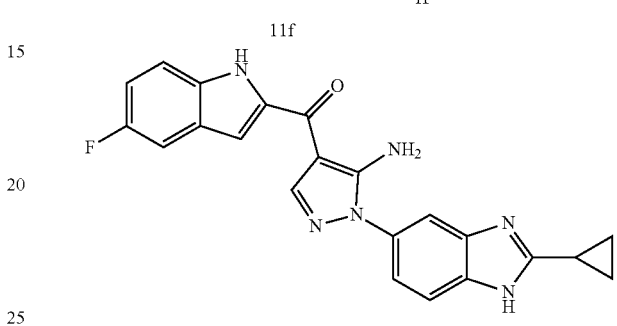
11

Step 1

Ethyl 5-fluoro-1H-indole-2-carboxylate

5-Fluoro-1H-indole-2-carboxylic acid 11a (853 mg, 4.76 mmol) was dissolved in 40 mL of absolute ethanol, 8 mL of 98% concentrated sulfuric acid was added, the reaction solution was heated to reflux for 2 hours. 250 mL of water was added to the reaction solution, the pH was adjusted to 7 to 8 with 1M NaOH, the solution was extracted with ethyl acetate (250 mL×3). The combined organic phases were dried over anhydrous sodium sulfate, filtered and concentrated under reduced pressure to obtain ethyl 5-fluoro-1H-indole-2-carboxylate 11b (857 mg, tan solid), yield: 86.8%.

MS m/z (ESI): 207.9 [M+1]

Step 2

Ethyl 5-fluoro-1-(phenylsulfonyl)-1H-indole-2-carboxylate

60% Sodium hydride (197 mg, 4.96 mmol) was dissolved in 17 mL of N, N-dimethylformamide, cooled down to 0° C., ethyl 5-fluoro-1H-indole-2-carboxylate 11b (857 mg, 4.14 mmol) was added, stirred until there's no bubbles generated, phenylsulfonyl chloride (0.59 mL, 4.59 mmol) was added dropwise to be dissolved in 3 mL of N, N-dimethylformamide solution, and the reaction was carried out in an ice bath for 1 hour after the completion of addition. 50 mL of water and 100 mL of ethyl acetate were added to the reaction solution, the pH was adjusted to neutral with saturated sodium bicarbonate solution. The organic phase was washed with water (50 mL×3), dried over anhydrous sodium sulfate, filtered and concentrated under reduced pressure. The obtained residue was purified by silica gel column chromatography (developing agent: system C) to obtain ethyl 5-fluoro-1-(phenylsulfonyl)-1H-indole-2-carboxylate 11c (1.40 g, pale yellow solid), yield: 97.5%.

MS m/z (ESI): 347.9 [M+1]

Step 3

3-(5-Fluoro-1-(phenylsulfonyl)-1H-indol-2-yl)-3-oxopropanenitrile

Ethyl 5-fluoro-1-(phenylsulfonyl)-1H-indole-2-carboxylate 11c (1.44 g, 4.36 mmol) and acetonitrile (358 mg, 8.73 mmol) were dissolved in 6 mL of tetrahydrofuran and cooled down to −78° C., lithium hexamethyldisilazide (9.16 mL, 9.16 mmol) was added dropwise, the reaction was carried out at −78° C. for 0.5 hour after the completing of the addition. The pH was adjusted to 5 to 6 with 1M hydrochloric acid, the mixture was extracted with ethyl acetate (50 mL×3). The combined organic phases were dried over anhydrous sodium sulfate, filtered and concentrated under reduced pressure to obtain 3-(5-fluoro-1-(phenylsulfonyl)-1H-indol-2-yl)-3-oxopropanenitrile 11d (588 mg, brown solid), yield: 41.5%.

MS m/z (ESI): 342.9 [M+1]

Step 4

3-(Dimethylamino)-2-(5-fluoro-1-(phenylsulfonyl)-1H-indole-2-carbonyl)acrylonitrile 3-(5-Fluoro-1-(phenylsulfonyl)-1H-indol-2-yl)-3-oxopropanenitrile 11d (588 mg, 1.72 mmol) was dissolved in 5 mL tetrahydrofuran, N, N-dimethylformamide dimethyl acetal (588 mg, 1.72 mmol) was added dropwise, the reaction was carried out at room temperature for 30 minutes. The reaction solution was concentrated under reduced pressure to obtain crude 3-(dimethylamino)-2-(5-fluoro-1-(phenylsulfonyl)-1H-indole-2-carbonyl)acrylonitrile 11e (683 mg, orange red solid), the product was directly subjected to the next step of reaction without purification.

Step 5

(5-Amino-1-(2-cyclopropyl-1H-benzo[d]imidazol-5-yl)-1H-pyrazol-4-yl)(5-fluoro-1-(phenylsulfonyl)-1H-indol-2-yl)methanone 3-(dimethylamino)-2-(5-fluoro-1-(phenylsulfonyl)-1H-indole-2-carbonyl)acrylonitrile 11e (683 mg, 1.72 mmol) was dissolved in 30 mL of absolute ethanol, 2-cyclopropyl-5-hydrazinyl-1H-benzo[d]imidazole hydrochloride 1e (641 mg, 2.45 mmol) was added, the reaction solution was refluxed for 4 hours. The reaction solution was cooled down to room temperature, solid precipitated. The solution was subjected to suction filtration, the filter cake was washed with ethanol (10 mL×3) then was subjected to infrared drying to obtain (5-amino-1-(2-cyclopropyl-1H-benzo[d]imidazol-5-yl)-1H-pyrid-4-yl)(5-fluoro-1-(phenylsulphonyl)-1H-indol-2-yl)methanone 1f (725 mg, light yellow solid), yield: 78.1%.

MS m/z (ESI): 540.8 [M+1]

Step 6

(5-Amino-1-(2-cyclopropyl-1H-benzo[d]imidazol-5-yl)-1H-pyrazol-4-yl)(5-fluoro-1H-indol-2-yl) methanone (5-Amino-1-(2-cyclopropyl-1H-benzo[d]imidazol-5-yl)-1H-pyrid-4-yl)(5-fluoro-1-(phenylsulphonyl)-1H-indol-2-yl)methanone 1f (725 mg, 1.34 mmol) was dissolved in 40 mL of absolute ethanol, 13 mL of sodium hydroxide solution (4M, 38 mmol) was added dropwise, the reaction solution was heated to 95° C. and reacted for 4 hours. The reaction solution was concentrated under reduced pressure to remove ethanol, the residue was diluted with ice, the mixture was stirred until the ice was dissolved, solid precipitated. The mixture was subjected to suction 50 filtration, the filter cake was washed with water (15 mL×3), toluene (water was contained) was concentrated under reduced pressure until it is dried to obtain (5-amino-1-(2-cyclopropyl-1H-benzo[d]imidazol-5-yl)-1H-pyrazol-4-yl)(5-fluoro-1H-indol-2-yl) methanone 11 (268 mg, light brown solid, HPLC purity: 96.19%), yield: 49.9%.

MS m/z (ESI): 400.9 [M+1]

$^1$H NMR (400 MHz, DMSO) δ 12.56 (s, 1H), 11.81 (s, 1H), 8.28 (s, 1H), 7.69-7.37 (m, 5H), 7.26 (s, 1H), 7.08 (d, J=35.1 Hz, 3H), 2.16 (s, 1H), 1.08 (s, 4H).

Example 12

(5-Amino-1-(2-cyclopropyl-1H-benzo[d]imidazol-5-yl)-1H-pyrazol-4-yl)(6-fluoro-1H-indol-2-yl)methanone

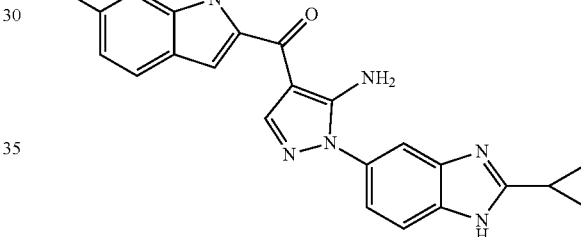

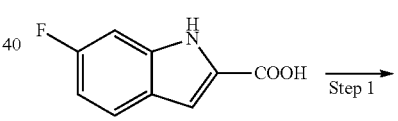

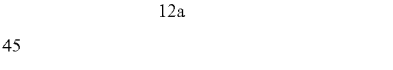

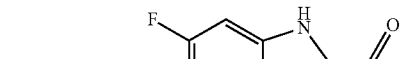

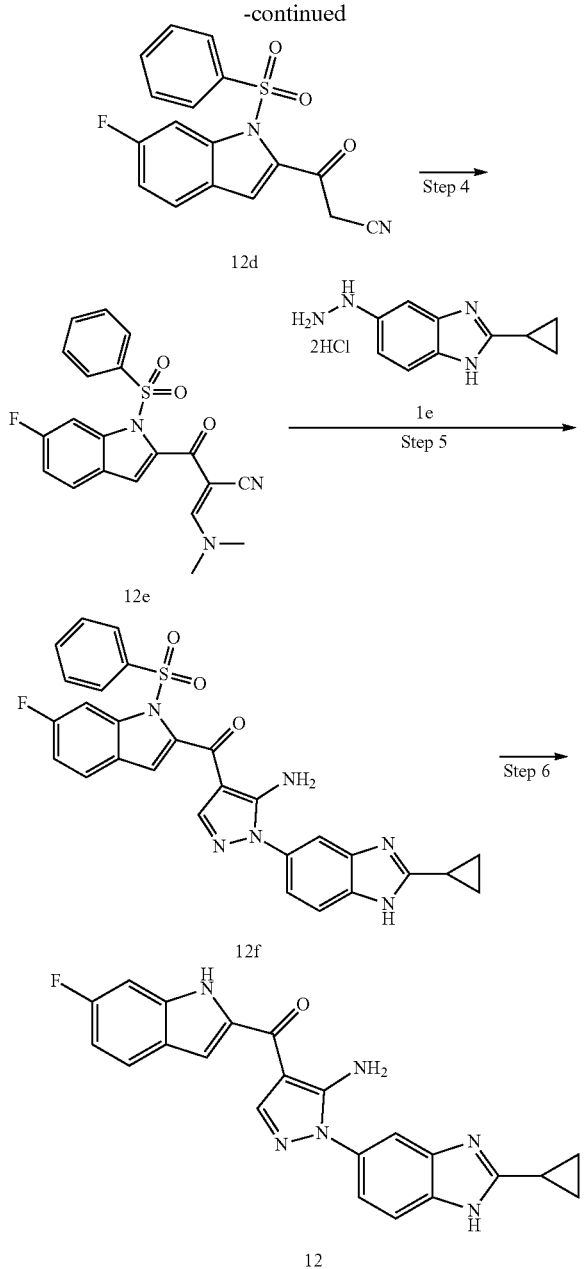

Step 2

Ethyl 6-fluoro-1-(phenylsulfonyl)-1H-indole-2-carboxylate

60% of Sodium hydride (305 mg, 12.72 mmol) was dissolved in 25 mL of N, N-dimethylformamide, cooled down to 0° C., ethyl 6-fluoro-1H-indole-2-carboxylate 12b (2.20 g, 10.6 mmol) was added and the mixture was stirred until no bubbles generated, phenylsulfonyl chloride (80 mg, 111.7 mmol) was added dropwise to be dissolved in 3 mL of N, N-dimethylformamide solution, and the reaction was carried out in an ice bath for 1 hour after the completion of addition. 50 mL of water and 100 mL of ethyl acetate were added to the reaction solution, the pH was adjusted to neutral with saturated ammonium chloride solution. The organic phase was washed with water (50 mL×3), dried over anhydrous sodium sulfate, filtered and concentrated under reduced pressure. The obtained residue was purified by silica gel column chromatography (developing solvent: system C) to obtain ethyl 6-fluoro-1-(phenylsulfonyl)-1H-indole-2-carboxylate 12c (1.93 g, white solid), yield: 54%.

MS m/z (ESI): 347.9 [M+1]

Step 3

3-(6-Fluoro-1-(phenylsulfonyl)-1H-indol-2-yl)3-oxopropanenitrile

Ethyl 6-fluoro-1-(phenylsulfonyl)-1H-indole-2-carboxylate 12c (2.75 g, 7.97 mmol) and acetonitrile (654.28 mg, 15.94 mmol) were dissolved in 12 mL of tetrahydrofuran, the solution was cooled down to −78° C., lithium hexamethyldisilazide (16.74 mL, 16.74 mmol) was added dropwise, the reaction was carried out for 1 hour at −78° C. after the completion of the addition. The pH was adjusted to neutral with saturated ammonium chloride solution, the mixture was extracted with ethyl acetate (50 mL×2). The combined organic phase was washed with saturated sodium chloride solution (60 mL×3) and saturated sodium chloride solution (60 mL×2), dried over anhydrous sodium sulfate, filtered and concentrated under reduced pressure to obtain 3-(6-fluoro-1-(phenylsulfonyl)-1H-indol-2-yl)-3-oxopropanenitrile 12d (2.43 g, yellow solid), yield: 89.2%.

MS m/z (ESI): 342.9 [M+1]

Step 1

Ethyl-6-fluoro-1H-indole-2-carboxylate

6-Fluoro-1H-indole-2-carboxylic acid 12a (2.00 g, 11.16 mmol) was dissolved in 60 mL of absolute ethanol, 10 mL of 98% concentrated sulfuric acid was added, the reaction liquid was heated to 105° C. and was reacted for 2 hours. The pH of the reaction solution was adjusted to 7 to 8 with 1M NaOH, the solution was extracted with ethyl acetate (150 mL×3). The combined organic phases were washed with saturated sodium chloride solution (2000 mL×3) then saturated ammonium chloride solution (200 mL), dried over anhydrous sodium sulfate, filtered and concentrated under reduced pressure to obtain ethyl 6-fluoro-1H-indole-2-carboxylate 12b (2.24 g, dark yellow solid), yield: 94.1%.

MS m/z (ESI): 207.9 [M+1]

Step 4

3-(Dimethylamino)-2-(6-fluoro-1-(phenylsulfonyl)-1H-indole-2-carbonyl)acrylonitrile 3-(6-Fluoro-1-(phenylsulfonyl)-1H-indol-2-yl)-3-oxopropanenitrile 12d (2.43 g, 7.10 mmol) was dissolved in 20 mL of tetrahydrofuran, N, N-dimethylformamide dimethyl acetal (845.84 mg, 7.10 mmol) was added dropwise and was reacted at room temperature for 30 minutes. The reaction solution was concentrated under reduced pressure, the resulting residue was purified by silica gel column chromatography (developing solvent: system C) to obtain 3-(dimethylamino)-2-(6-fluoro-1-(phenylsulfonyl)-1H-indole-2-carbonyl)acrylonitrile 12e (220 mg, yellow solid), yield: 78.1%.

MS m/z (ESI): 397.9 [M+1]

Step 5

(5-Amino-1-(2-cyclopropyl-1H-benzo[d]imidazol-5-yl)-1H-pyrazol-4-yl)(6-fluoro-1-(phenylsulfonyl)-1H-indol-2-yl)methanone 3-(Dimethylamino)-2-(6-fluoro-1-(phenylsulfonyl)-1H-indole-2-carbonyl)acrylonitrile 12e (2.02 g, 5.08 mmol) was dissolved in 30 mL absolute ethanol, 2-cyclopropyl-5-hydrazinyl-1H-benzo[d]imidazole hydrochloride 1e (1.89 g, 7.26 mmol) was added, the reaction solution was refluxed for 4 hours. The reaction solution was cooled down to room temperature, solid precipitated. The solution was subjected to suction filtration, the filter cake was washed with ethanol (20 mL×3) then was subjected to infrared drying to obtain crude (5-amino-1-(2-cyclopropyl-1H-benzo[d]imidazol-5-yl)-1H-pyrazol-4-yl)(6-fluoro-1-(phenylsulfonyl)-1H-indol-2yl)methanone 12f (2.78 g, light yellow solid), the product was subjected to the next step of reaction without purification.

MS m/z (ESI): 540.8 [M+1]

Step 6

(5-Amino-1-(2-cyclopropyl-1H-benzo[d]imidazol-5-yl)-1H-pyrazol-4-yl)(6-fluoro-1H-indol-2-yl)methanone (5-Amino-1-(2-cyclopropyl-1H-benzo[d]imidazol-5-yl)-1H-pyrazol-4-yl)(6-fluoro-1-(phenylsulfonyl)-1H-indol-2yl)methanone 12f (2.00 g, 3.70 mmol) was dissolved in 120 mL of absolute ethanol, sodium hydroxide solution (562.3 mg, 14.06 mmol) was added, the reaction solution was heated to 103° C. and was reacted for 3 hours. The reaction solution was concentrated under reduced pressure to remove ethanol, and the residue was diluted with ice, the mixture was stirred until the ice was dissolved, solid precipitated. The mixture was subjected to suction filtration, the filter cake was washed with water (150 mL) and the filter cake was concentrated under reduced pressure until the cake was dry, the obtained residue was purified by silica gel column chromatography (developing agent: system B) to obtain (5-amino-1-(2-cyclopropyl-1H-benzo[d]imidazol-5-yl)-1H-pyrazol-4-yl)(6-fluoro-1H-indol-2-yl) methanone 12 (774 mg, light brown solid, HPLC purity: 94.22%), yield: 52.4%.

MS m/z (ESI): 400.9 [M+1]

$^1$H NMR (400 MHz, DMSO) δ 12.72-12.38 (s, 1H), 11.79 (s, 1H), 8.30 (s, 1H), 7.8-7.65 (m, 1H), 7.65-7.52 (m, 2H), 7.52-7.40 (m, 1H), 7.19 (s, 2H), 7.1-6.85 (m, 3H), 2.25-2.09 (m, 1H), 1.32-1.20 (m, 1H), 1.18-1.02 (m, 3H).

Example 13

(5-Amino-1-(2-cyclopropyl-1H-benzo[d]imidazol-5-yl)-1H-pyrazol-4-yl)(6-bromo-1H-indol-2-yl)methanone

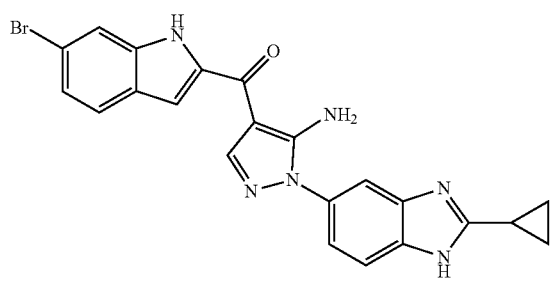

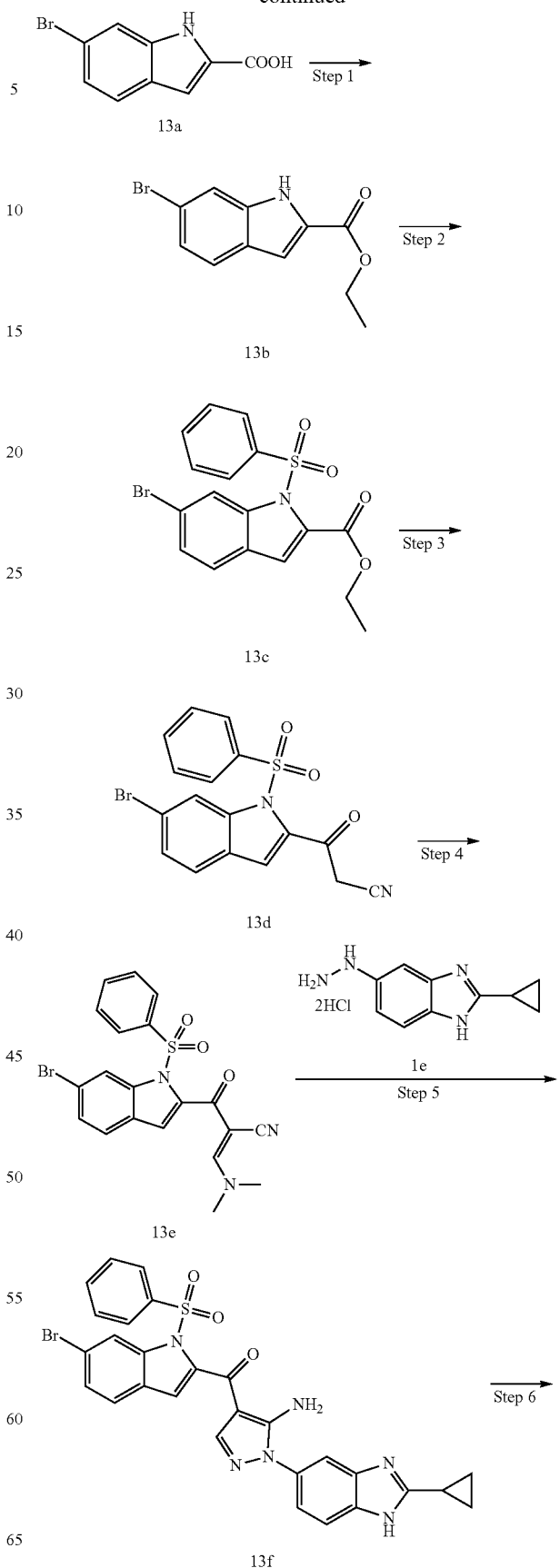

-continued

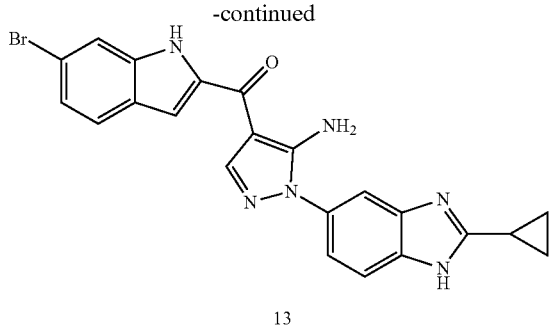

13

Step 1

Ethyl 6-bromo-1H-indole-2-carboxylate

6-Bromo-1H-indole-2-carboxylic acid 13a (5.00 g, 20.8 mmol) was dissolved in 75 mL of absolute ethanol and cooled down to 0° C., 12.5 mL 98% of concentrated sulfuric acid was slowly added, the reaction solution was heated to 100° C. and was reacted for 2 hours. The reaction solution was slowly poured into an ice-water mixture (200 mL), the newly obtained mixture was extracted with ethyl acetate (50 mL×3). The combined organic phases were washed with saturated brine (250 mL) then saturated sodium carbonate solution (250 mL), dried over anhydrous sodium sulfate, filtered and concentrated under reduced pressure to obtain crude ethyl 6-bromo-1H-indole-2-carboxylate 13b (5.58 g, light red solid), the product was subjected to the next step of reaction without purification.

MS m/z (ESI): 269.9 [M+1]

Step 2

Ethyl 6-bromo-1-(phenylsulfonyl)-1H-indole-2-carboxylate

Ethyl 6-bromo-1H-indole-2-carboxylate 13b (5.58 g, 20.8 mmol) was dissolved in 50 mL of N, N-dimethylformamide, the solution was cooled down to 0° C., stirred for 5 minutes, 60% of sodium hydride (1.10 g, 27.0 mmol) was added, the mixture was reacted at 0° C. for 0.5 h, then phenylsulfonyl chloride (80 mg, 11.7 mmol) was added and the temperature of the mixture was increased to room temperature and reacted for 2 hours. 200 mL of a saturated ammonium chloride solution was added to the reaction solution, the mixture was extracted with ethyl acetate (50 mL×3). The combined organic phases were washed with water (200 mL×3), dried over anhydrous sodium sulfate, filtered and concentrated under reduced pressure. The obtained residue was purified by silica gel column chromatography (developing agent: system C) to obtain ethyl 6-bromo-1-(phenylsulfonyl)-1H-indole-2-carboxylate 13c (6.90 g, brown solid), yield: 81.3%.

MS m/z (ESI): 407.8 [M+1]

Step 3

3-(6-Bromo-1-(phenylsulfonyl)-1H-indol-2-yl)-3-oxopropanenitrile

Ethyl 6-bromo-1-(phenylsulfonyl)-1H-indole-2-carboxylate 13c (6.90 g, 16.9 mmol) and acetonitrile (1.80 mL, 33.8 mmol) were dissolved in 45 mL of tetrahydrofuran, the mixture was cooled down to −78° C., stirred for 5 minutes, lithium hexamethyldisilazide (35.5 mL, 35.5 mmol) was added dropwise, the temperature of the mixture was increased naturally after the completion of addition and the mixture was reacted for 1 hour. 60 mL of saturated ammonium chloride solution was added to the reaction solution, stirred for 10 minutes, 60 mL of water was added, the mixture was extracted with ethyl acetate (50 mL×3). The combined organic phases were dried over anhydrous sodium sulfate, filtered and concentrated under reduced pressure. The obtained residue was purified by silica gel column chromatography (developing agent: system C) to obtain 3-(6-bromo-1-(phenylsulfonyl)-1H-indol-2-yl)-3-oxopropanenitrile 13d (4.22 g, yellow solid), yield: 62.1%.

MS m/z (ESI): 402.7 [M+1]

Step 4

3-(Dimethylamino)-2-(6-bromo-1-(phenylsulfonyl)-1H-indole-2-carbonyl)acrylonitrile 3-(6-Bromo-1-(phenylsulfonyl)-1H-indol-2-yl)-3-oxopropanenitrile 13d (3.50 g, 8.68 mmol) was dissolved in 25 mL of tetrahydrofuran, N,N-dimethylformamide dimethyl acetal was added dropwise (1.76 mL, 13.2 mmol), the mixture was reacted at room temperature for 30 minutes. The reaction solution was concentrated under reduced pressure to obtain crude 3-(dimethylamino)-2-(6-bromo-1-(phenylsulfonyl)-1H-indole-2-carbonyl)acrylonitrile 13e (4.00 g, yellow solid), the product was directly subjected to the next step of reaction without purification.

MS m/z (ESI): 457.8 [M+1]

Step 5

(5-Amino-1-(2-cyclopropyl-1H-benzo[d]imidazol-5-yl)-1H-pyrazol-4-yl)(6-bromo-1-(phenylsulfonyl)-1H-indol-2-yl)methanone 3-(Dimethylamino)-2-(6-bromo-1-(phenylsulfonyl)-1H-indole-2-carbonyl)acrylonitrile 13e (3.00 g, 6.54 mmol) was dissolved in 30 mL of absolute ethanol, 2-cyclopropyl-5-hydrazinyl-1H-benzo[d]imidazole hydrochloride 1e (2.22 g, 8.51 mmol) was added, the reaction solution was refluxed for 4 hours. The reaction solution was cooled down to room temperature, solid precipitated. The solution was subjected to suction filtration, the filter cake was washed with ethanol (10 mL×4) then ether (10 mL×3) and vacuum dried to obtain (5-amino-1-(2-cyclopropyl-1H-benzo[d]imidazol-5-yl)-1H-pyrazol-4-yl)(6-bromo-1-(phenylsulfonyl)-1H-indol-2-yl)methanone 13f (3.00 g, yellow solid), yield: 76.3.

MS m/z (ESI): 600.7 [M+1]

Step 6

(5-Amino-1-(2-cyclopropyl-1H-benzo[d]imidazol-5-yl)-1H-pyrazol-4-yl)(6-bromo-1H-indol-2-yl)methanone (5-Amino-1-(2-cyclopropyl-1H-benzo[d]imidazol-5-yl)-1H-pyrazol-4-yl)(6-bromo-1-(phenyl sulfonyl)-1H-indol-2-yl)methanone 13f (180 mg, 0.30 mmol) was dissolved in 20 mL of absolute ethanol, 3.34 mL of sodium hydroxide solution (4M, 1.34 mmol) was added, the reaction solution was heated to 90° C. and was reacted for 3 hours. The reaction solution was concentrated under reduced pressure to remove ethanol, 10 mL of water was added, the mixture was extracted with a mixed solvent of dichloromethane and methanol (V/V=15/1) (15 mL×2). The organic phases were combined and were concentrated under reduced pressure to obtain 50 (5-amino-1-(2-cyclopropyl-1H-benzo[d]imidazol-5-yl)-1H-pyrazol-4-yl)(6-bromo-1H-indol-2-yl) methanone 13 (76 mg, light brown solid, HPLC purity: 94.18%), yield: 55.1%.

MS m/z (ESI): 460.8 [M+1]

$^1$H NMR (400 MHz, DMSO) δ 12.51 (s, 1H), 11.84 (s, 1H), 8.31 (s, 1H), 7.66 (d, J=8.6 Hz, 2H), 7.57 (s, 2H), 7.49 (s, 1H), 7.32-7.18 (m, 2H), 7.01 (s, 2H), 2.16 (ddd, J=13.3, 8.1, 5.1 Hz, 1H), 1.17-1.00 (m, 4H).

Example 14

(5-Amino-1-(2-cyclopropyl-1H-benzo[d]imidazol-5-yl)-1H-pyrazol-4-yl)(6-(1-methyl-1,2,3, 6-tetrahydropyrid-4-yl)-1H-indol-2-yl)methanone

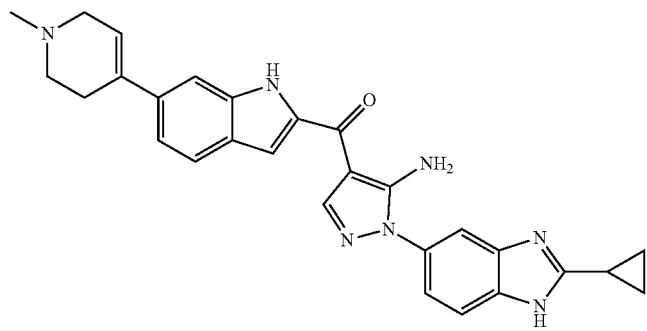

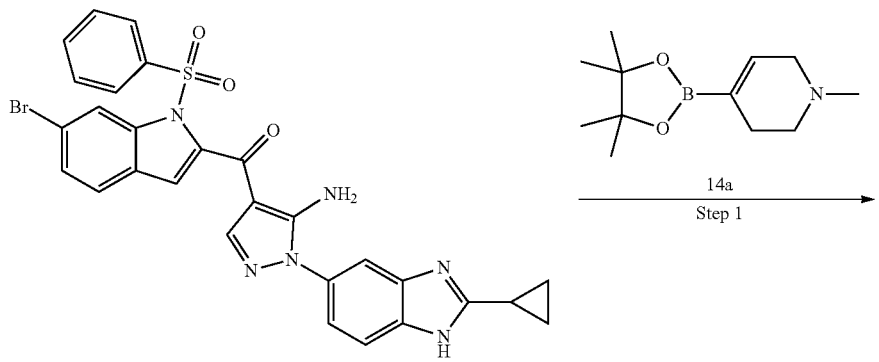

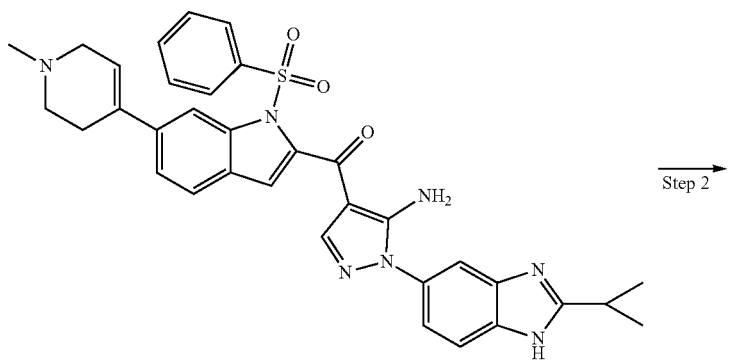

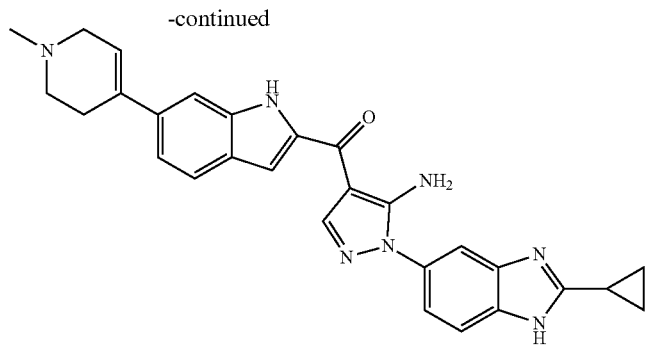

14

Step 1

5-Amino-1-(2-cyclopropyl-1H-benzo[d]imidazol-5-yl)-1H-pyrazol-4-yl)(6-(1-methyl-1, 2, 3, 6-tetrahydropyridin-4-yl)-1-(phenylsulfonyl)-1H-indol-2-yl)methanone (5-Amino-1-(2-cyclopropyl-1H-benzo[d]imidazol-5-yl)-1H-pyrazol-4-yl)(6-bromo-1-(phenyl sulfonyl)-1H-indol-2-yl)methanone 13f (421 mg, 0.70 mmol), 1-methyl-4-(4,4,5,5-tetramethyl-1,3,2-dioxaborolan-2-yl)-1,2,3,6-tetrahydropyridine 14a (187 mg, 1.05 mmol), bis(triphenylphosphine)palladium chloride (49 mg, 0.07 mmol) and sodium carbonate (148 mg, 1.40 mmol) were dissolved in 14.4 mL of the mixed solution of 1.4 dioxane and water (V/V=5/1), a microwave reaction was carried out under argon at 140° C. for 10 minutes. The reaction solution was concentrated under reduced pressure, the obtained residue was purified by silica gel column chromatography (developing agent: system B) to obtain (5-amino-1-(2-cyclopropyl-1H-benzo[d]imidazol-5-yl)-1H-pyrazol-4-yl)(6-(1-methyl-1,2,3,6-tetrahydropyridin-4-yl)-1-(phenylsufonyl)-1H-indol-2-yl)methanone 14b (145 mg, yellow solid), yield: 33.6%.

MS m/z (ESI): 617.9 [M+1]

Step 2

5-Amino-1-(2-cyclopropyl-1H-benzo[d]imidazol-5-yl)-1H-pyrazol-4-yl)(6-(1-methyl-1, 2, 3, 6-tetrahydropyridin-4-yl)-1H-indol-2-yl)methanone (5-Amino-1-(2-cyclopropyl-1H-benzo[d]imidazol-5-yl)-1H-pyrazol-4-yl)(6-(1-methyl-1,2,3, 6-tetrahydropyridin-4-yl)-1-(phenylsufonyl)-1H-indol-2-yl)methanone 14b (145 mg, 0.235 mmol) was dissolved in 15 mL of absolute ethanol, 2.70 mL of sodium hydroxide solution (4M, 10.8 mmol) was added and the reaction solution was heated to 90° C. and was reacted for 3 hours. The reaction solution was concentrated under reduced pressure to remove ethanol, 15 mL of water was added, the mixture was extracted with a mixed solvent of dichloromethane and methanol (V/V=10/1) (8 mL×3). The organic phases were combined and concentrated under reduced pressure. The obtained residue was purified by silica gel column chromatography (developing agent: system B) to obtain 5-amino-1-(2-cyclopropyl-1H-benzo[d]imidazol-5-yl)-1H-pyrazol-4-yl)(6-(1-methyl-1, 2, 3, 6-tetrahydropyridin-4-yl)-1H-indol-2-yl)methanone 14 (63 mg, brown solid, HPLC purity: 97.31%), yield: 56.3%.

MS m/z (ESI): 478.0 [M+1]

$^1$H NMR (400 MHz, DMSO) δ 12.57 (s, 1H), 11.68 (s, 1H), 8.31 (s, 1H), 7.63 (d, J=8.4 Hz, 1H), 7.57 (s, 2H), 7.44 (d, J=10.9 Hz, 2H), 7.27 (d, J=8.3 Hz, 2H), 7.00 (s, 2H), 6.19 (s, 1H), 3.04 (s, 2H), 2.59 (d, J=5.0 Hz, 2H), 2.54 (s, 2H), 2.29 (s, 3H), 2.16 (td, J=7.9, 4.1 Hz, 1H), 1.10-1.02 (m, 4H).

Example 15

(5-Amino-1-(2-cyclopropyl-1H-benzo[d]imidazol-5-yl)-1H-pyrazol-4-yl)(6-(1-methyl-1H-pyrazol-4-yl)-1H-indol-2-yl)methanone

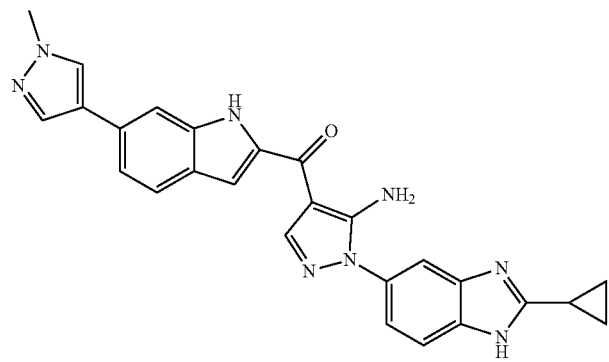

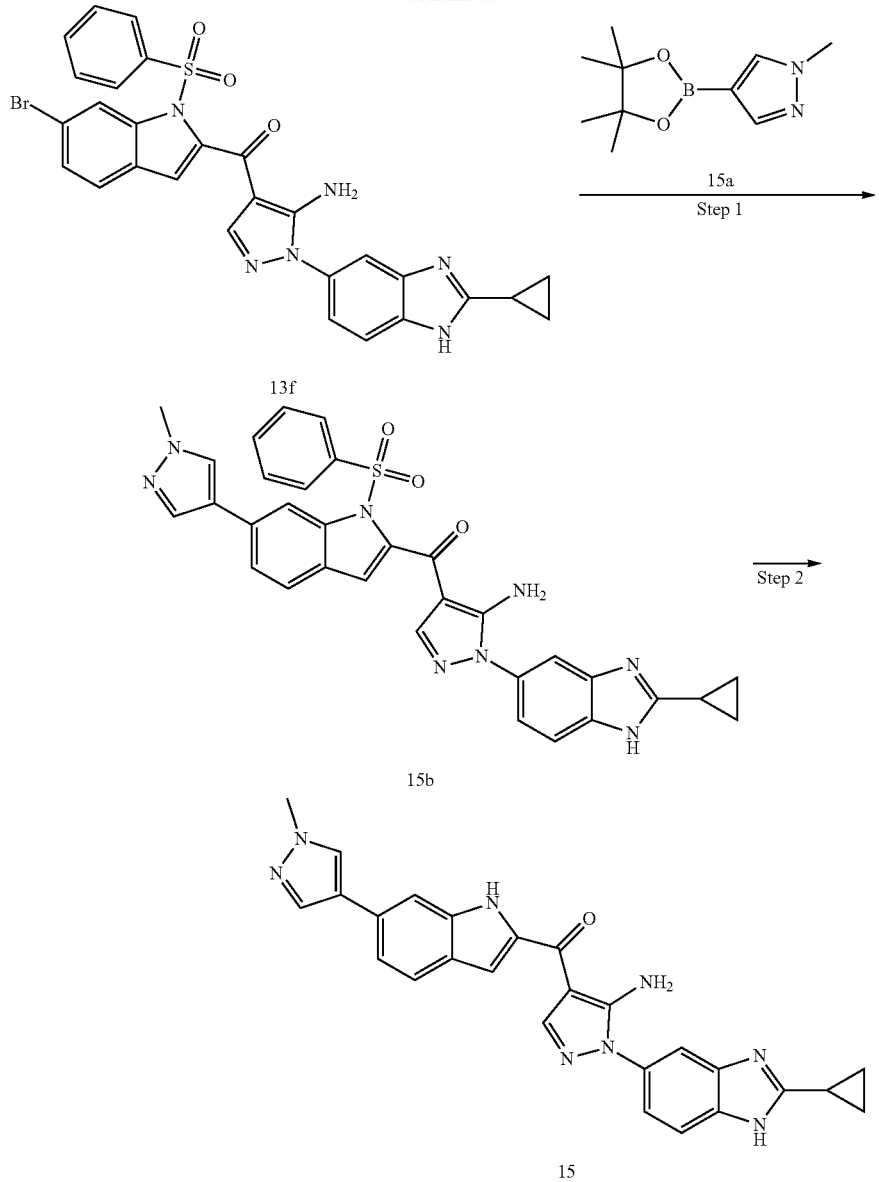

Step 1

(5-Amino-1-(2-cyclopropyl-1H-benzo[d]imidazol-5-yl)-1H-pyrazol-4-yl)(6-(1-methyl-1H-pyrazol-4-yl)-1-(phenylsulfonyl)-1H-indol-2-yl)methanone

(5-Amino-1-(2-cyclopropyl-1H-benzo[d]imidazol-5-yl)-1H-pyrazol-4-yl)(6-bromo-1-(phenyl sulfonyl)-1H-indol-2-yl)methanone 13f (421 mg, 0.70 mmol), 1-methyl-4-(4,4,5,5-tetramethyl-1,3,2-dioxaborolan-2-yl)-1H-pyrazole 15a (175 mg, 0.84 mmol), bis(triphenylphosphine)palladium chloride (49 mg, 0.07 mmol) and sodium carbonate (148 mg, 1.40 mmol) were dissolved in 14.4 mL of the mixed solution of 1.4 dioxane and water (V/V=5/1), a microwave reaction was carried out under argon at 140° C. for 10 minutes. The reaction solution was concentrated under reduced pressure, and the obtained residue was purified by silica gel column chromatography (developing agent: system B) to obtain (5-amino-1-(2-cyclopropyl-1H-benzo[d]imidazol-5-yl)-1H-pyrazol-4-yl)(6-(1-methyl-1H-pyrazol-4-yl)-1-(phenylsufonyl)-1H-indol-2-yl)methanone 15b (115 mg, yellow solid), yield: 27.3%.

MS m/z (ESI): 602.8 [M+1]

Step 2

(5-Amino-1-(2-cyclopropyl-1H-benzo[d]imidazol-5-yl)-1H-pyrazol-4-yl)(6-(1-methyl-1H-pyrazol-4-yl)-1H-indol-2-yl)methanone

(5-Amino-1-(2-cyclopropyl-1H-benzo[d]imidazol-5-yl)-1H-pyrazol-4-yl)(6-(1-methyl-1H-pyrazol-4-yl)-1-(phenylsulfonyl)-1H-indol-2-yl)methanone 15b (115 mg, 0.19 mmol) was dissolved in 12 mL of absolute ethanol, 2.20 mL of sodium hydroxide solution (4M, 8.75 mmol) was added, the reaction solution was heated to 90° C. and reacted for 3 hours. The reaction solution was concentrated under reduced pressure to remove ethanol, 15 mL of water was added, the mixture was extracted with a mixed solvent of dichloromethane and methanol (V/V=10/1) (8 mL×3). The organic phases were combined and concentrated under reduced pressure. The obtained residue was purified by silica gel column chromatography (developing agent: system B) to obtain (5-amino-1-(2-cyclopropyl-1H-benzo[d]imidazol-5-yl)-1H-pyrazol-4-yl)(6-(1-methyl-1H-pyrazol-4-yl)-1H-indol-2-yl)methanone 15 (20 mg, yellow solid, HPLC purity: 95.51%), yield: 22.7%.

MS m/z (ESI): 462.9 [M+1]

¹H NMR (400 MHz, DMSO) δ 12.52 (s, 1H), 11.68 (s, 1H), 8.30 (s, 1H), 8.14 (s, 1H), 7.84 (s, 1H), 7.67 (d, J=8.4 Hz, 1H), 7.57 (s, 3H), 7.43 (s, 1H), 7.32 (d, J=8.4 Hz, 1H), 7.27 (d, J=8.4 Hz, 1H), 6.99 (s, 2H), 3.89 (s, 3H), 2.20-2.12 (m, 1H), 1.08 (dd, J=5.5, 3.2 Hz, 3H).

Example 16

(5-Amino-1-(2-cyclopropyl-1H-benzo[d]imidazol-5-yl)-1H-pyrazol-4-yl)(6-(1-ethyl-1H-pyrazol-4-yl)-1H-indol-2-yl)methanone

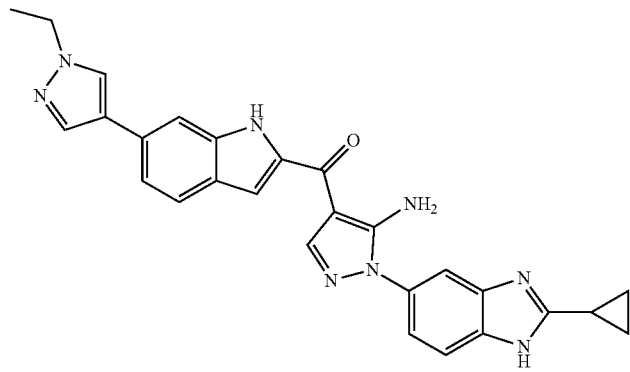

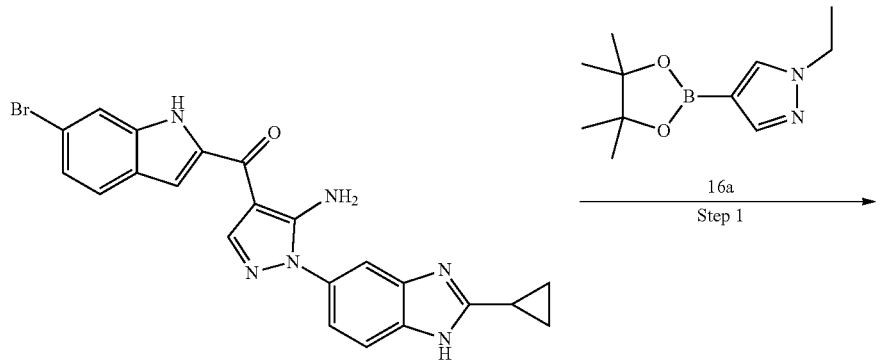

13

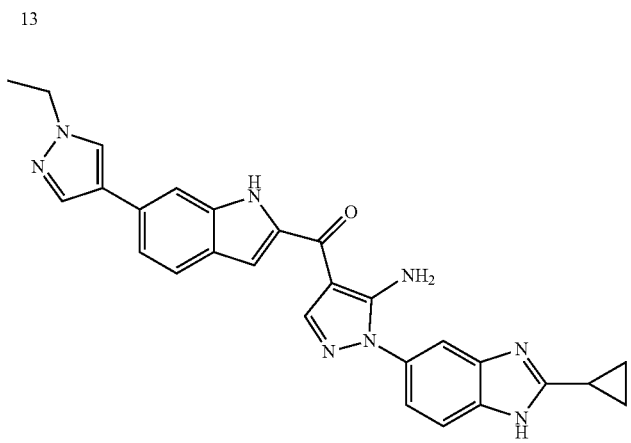

16

(5-Amino-1-(2-cyclopropyl-1H-benzo[d]imidazol-5-yl)-1H-pyrazol-4-yl)(6-(1-ethyl-1H-pyrazol-4-yl)-1H-indol-2-yl)methanone (5-Amino-1-(2-cyclopropyl-1H-benzo[d]imidazol-5-yl)-1H-pyrazol-4-yl)(6-bromo-1H-indol-2-yl)methanone 16a (636 mg, 1.38 mmol), 1-ethyl-4-(4,4,5,5-tetramethyl-1,3,2-dioxaborolan-2-yl)-1H-pyrazole 13 (376 mg, 1.65 mmol), tetrakis (triphenylphosphine) palladium (80 mg, 0.07 mmol) and sodium carbonate (365 mg, 3.45 mmol) were dissolved in 10.2 mL of the mixed solvent of 1.4 dimethyl ether and water (V/V=45/4), a microwave reaction was carried out under argon protection at 140° C. for 4 hours. The reaction solution was concentrated under reduced pressure, the obtained residue was purified by silica gel column chromatography (developing agent: system B) to obtain (5-amino-1-(2-cyclopropyl-1H-benzo[d]imidazol-5-yl)-1H-pyrazol-4-yl)(6-(1-ethyl-1H-pyrazol-4-yl)-1H-indol-2-yl)methanone 16 (481 mg, yellow solid, HPLC purity: 96.43%), yield: 68.4%.

MS m/z (ESI): 477.0 [M+1]

$^1$H NMR (400 MHz, DMSO) δ 12.51 (s, 1H), 11.67 (s, 1H), 8.30 (s, 1H), 8.19 (s, 1H), 7.85 (s, 1H), 7.67 (d, J=8.3 Hz, 1H), 7.58 (t, J=12.8 Hz, 3H), 7.43 (s, 1H), 7.34 (d, J=8.4 Hz, 1H), 7.27 (d, J=8.5 Hz, 1H), 6.99 (d, J=19.7 Hz, 2H), 4.18 (q, J=7.2 Hz, 2H), 2.16 (s, 1H), 1.43 (t, J=7.3 Hz, 3H), 1.14-1.03 (m, 4H).

Example 17

2-(5-Amino-1-(2-cyclopropyl-1H-benzo[d]imidazol-5-yl)-1H-pyrazole-4-carbonyl)-1H-indole-6-carbonitrile

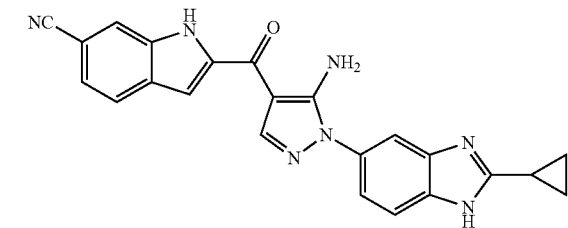

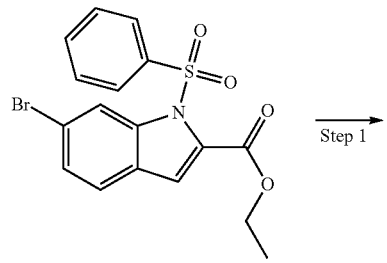

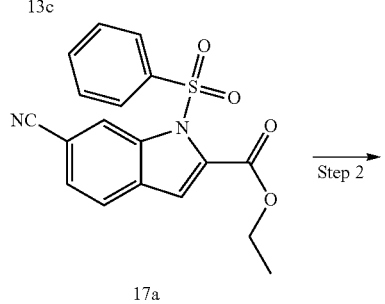

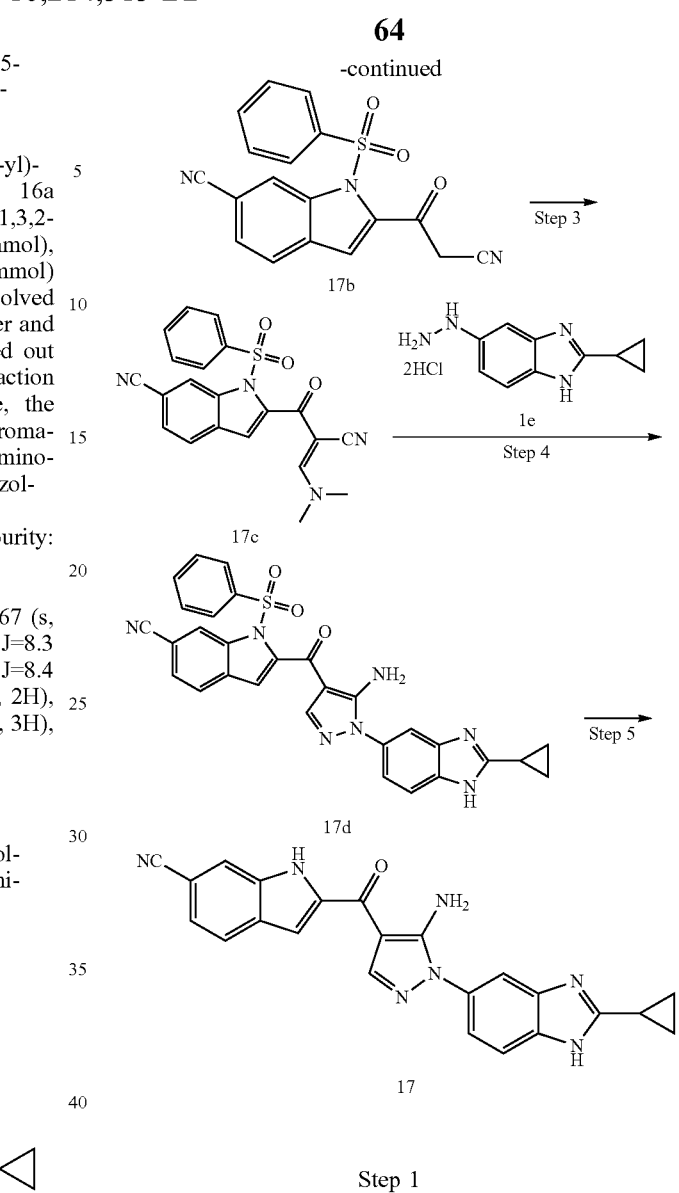

Step 1

Ethyl 6-cyano-1-(phenylsulfonyl)-1H-indole-2-carboxylate

Ethyl 6-bromo-1-(phenylsulfonyl)-1H-indole-2-carboxylate 13c (2.83 g, 6.94 mmol), copper cyanide (932 mg, 10.40 mmol) were dissolved in 50 mL of N-methyl pyrrolidone, the solution was heated at 150° C. and reacted for 5 hours. 100 mL of ethyl acetate was added to the reaction solution, the mixture was washed with water (50 mL×3), dried over anhydrous sodium sulfate, filtered and concentrated under reduced pressure. The obtained residue was purified by silica gel column chromatography (developing agent: system C) to obtain ethyl 6-cyano-1-(phenylsulfonyl)-1H-indole-2-carboxylate 17a (900 mg, white powder), yield: 36.6%.

MS m/z (ESI): 354.9 [M+1]

Step 2

2-(2-Cyanoacetyl)-1-(phenylsulfonyl)-1H-indole-6-carbonitrile

Ethyl 6-cyano-1-(phenylsulfonyl)-1H-indole-2-carboxylate 17a (800 mg, 2.26 mmol) and acetonitrile (0.24 mL, 4.51 mmol) were dissolved in 20 mL of tetrahydrofuran, the solution was cooled down to −78° C., lithium hexamethyldisilazide (4.97 mL, 4.97 mmol) was added dropwise, after the completion of addition, the temperature of the mixture was increased naturally to room temperature and the mixture was reacted for 1 hour. 50 mL of water and 5 mL of a saturated ammonium chloride solution were added to the reaction solution, the mixture was extracted with ethyl acetate (50 mL×3). The combined organic phases were dried over anhydrous sodium sulfate, filtered and concentrated under reduced pressure. The obtained residue was purified by silica gel column chromatography (developing agent: system C) to obtain 2-(2-cyanoacetyl)-1-(phenylsulfonyl)-1H-indole-6-carbonitrile 17b (111 mg, light yellow solid), yield: 14.1%.

MS m/z (ESI): 349.9 [M+1]

Step 3

2-(1-Cyano-2-(dimethylamino)acryloyl)-1-(phenylsulfonyl)-1H-indole-6-carbonitrile 2-(2-cyanoacetyl)-1-(phenylsulfonyl)-1H-indole-6-carbonitrile 17b (111 mg, 0.318 mmol) was dissolved in 5 mL of tetrahydrofuran, N,N-dimethylformamide dimethyl acetal (38 mg, 0.318 mmol) was added dropwise, the mixture was reacted at room temperature for 30 minutes. The reaction solution was concentrated under reduced pressure to obtain 2-(1-cyano-2-(dimethylamino)acryloyl)-1-(phenylsulfonyl)-1H-indole-6-carbonitrile 17c (114 mg, light yellow solid), yield: 88.7%.

MS m/z (ESI): 404.9 [M+1]

Step 4

2-(5-Amino-1-(2-cyclopropyl-1H-benzo[d]imidazol-5-yl)-1H-pyrazole-4-carbonyl)-1-(phen ylsulfonyl)-1H-indole-6-carbonitrile 2-(1-cyano-2-(dimethylamino)acryloyl)-1-(phenylsulfonyl)-1H-indole-6-carbonitrile 17c (114 mg, 0.28 mmol) and 2-cyclopropyl-5-hydrazinyl-1H-benzo[d]imidazole hydrochloride 1e (105 mg, 0.40 mmol) were dissolved in 3 mL of absolute ethanol, the reaction solution was refluxed for 4 hours. The reaction solution was cooled down to room temperature, solid precipitated. The solution was subjected to suction filtration, the filter cake was washed with ethanol (3 mL×3) and then vacuum dried to obtain 2-(5-amino-1-(2-cyclopropyl-1H-benzo[d]imidazol-5-yl)-1H-pyrazole-4-carbonyl)-1-(phenylsulfonyl)-1H-indole-6-carbonitrile 17d (109 mg, yellow solid), yield: 70.6%.

MS m/z (ESI): 547.8 [M+1]

Step 5

2-(5-Amino-1-(2-cyclopropyl-1H-benzo[d]imidazol-5-yl)-1H-pyrazole-4-carbonyl)-1H-indole-6-carbonitrile 2-(5-Amino-1-(2-cyclopropyl-1H-benzo[d]imidazol-5-yl)-1H-pyrazole-4-carbonyl)-1-(phenylsulfonyl)-1H-indole-6-carbonitrile 17d (109 mg, 0.20 mmol) was dissolved in 6 mL of absolute ethanol, 1.89 mL of sodium hydroxide solution (4M, 7.56 mmol) was added, the reaction solution was heated to 90° C. and was reacted for 4 hours. The reaction solution was poured into ice water (30 mL) to allow solid to precipitate, the solution was filtered, the filter cake was dried under reduced pressure then was purified by thin layer chromatography (developing agent: system B) to obtain 2-(5-amino-1-(2-cyclopropyl-1H-benzo[d]imidazol-5-yl)-1H-pyrazole-4-carbonyl)-1H-indole-6-carbonitrile 17 (5 mg, light yellow solid, HPLC purity: 98.54%), yield: 6.2%.

MS m/z (ESI): 407.9 [M+1]

$^1$H NMR (400 MHz, DMSO) δ 12.51 (s, 1H), 12.23 (s, 1H), 8.32 (s, 1H), 7.94-7.86 (m, 2H), 7.58 (s, 2H), 7.56-7.50 (m, 1H), 7.42 (d, J=8.3 Hz, 1H), 7.26 (d, J=8.6 Hz, 1H), 7.07 (s, 2H), 2.16 (s, 1H), 1.14-1.02 (m, 4H).

Biological Evaluation

Test Example 1. Determination of the Effects of the Compounds of the Present Invention on FGFR Kinase Activity The following assay was used to determine the inhibition rate of the preferred compounds of the present invention to the kinase activity of the recombinant human FGFR protein in vitro conditions. This assay used Cisbio's HTRF®KinEASE-TK tyrosine kinase kit (Cat. No. 62TK0PEB), through determining the degree of phosphorylation of the biotinylated polypeptide substrate, the determination was carried out by time-resolved fluorescence energy resonance transfer method (TF-FRET). Human FGFR protein was purchased from Carna bioscience (Japan, Cat. No. FGFR1#08-133, FGFR2#08-134, FGFR3#08-135, FGFR4#08-136).

For detailed assay, please refer to the kit instructions, the experimental procedure was summarized as follows: the compound of the present invention was first dissolved in DMSO, the solution was subjected to gradient dilution with the buffer solution provided in the kit so that the range of the final concentration of the compound to be tested in the reaction system was 10 μM to 0.1 nM, the final concentration of DMSO was 0.1%. The concentration of the tested adenosine triphosphate (ATP) was the pre-determined Km value corresponding to the ATP of each FGFR subtype. The compound was first incubated with a certain amount of FGFR protein at room temperature for 5 to 30 minutes, followed by the addition of ATP and the biotinylated polypeptide substrate to the reaction solution to initiate the phosphorylation reaction, and the mixture was incubated at room temperature for 50 minutes. Subsequently, an antiphosphorylated tyrosine antibody coupled with a compound containing europium-based element and streptavidin coupled with a modified allophycocyanin XL665 were added to the reaction and the mixture was incubated continuously for 1 hour at room temperature. After incubation, the fluorescence intensity of each well at emission wavelengths of 620 nM and 665 nM were read at the excitation wavelength of 304 nm in the TF-FRET mode of the microplate reader. The inhibition rate of the compound at each concentration was calculated by comparing the fluorescence intensity ratio 50 with the control group, and the $IC_{50}$ value of the compound was calculated by curve fitting with the logarithmic concentration-inhibition rate by GraphPad Prism 5, see table 1 below.

TABLE 1

IC$_{50}$ data of preferred compounds of the present invention for inhibition of FGFR kinase activity

| Example No. | IC$_{50}$(nM) | | | |
|---|---|---|---|---|
| | FGFR1 | FGFR2 | FGFR3 | FGFR4 |
| 1 | 15.1 | 6.2 | 22 | 1000 |
| 7 | 75.3 | 30 | >100 | >10000 |
| 9 | >10000 | 44 | >10000 | >10000 |
| 11 | 21 | 10 | 26 | 1000 |
| 12 | 19 | 5 | 18 | 308 |
| 13 | 5 | 2.6 | 46 | 1738 |
| 15 | 14 | 2.7 | 45 | 1000 |
| 16 | 4.9 | 0.7 | 6.8 | 280 |
| 17 | 8.6 | 5 | 9.1 | 135 |

As can be seen from table 1, the preferred compounds of the present invention have better activity for inhibiting FGFR1, FGFR2 and FGFR3 than FGFR4, wherein the compounds of Examples 1, 11-13, 15-17 have good activity for inhibiting FGFR1, FGFR2 and FGFR3, the compounds of Examples 7 and 9 have good activity for inhibiting FGFR2.

TABLE 2

Selective activity data for FGFR kinase of the preferred compounds of the present invention.

| Example No. | IC$_{50}$(FGFR4)/ IC$_{50}$(FGFR1) | IC$_{50}$(FGFR4)/ IC$_{50}$(FGFR2) | IC$_{50}$(FGFR4)/ IC$_{50}$(FGFR3) |
|---|---|---|---|
| 1 | 66.2 | 161.2 | 22 |
| 7 | >132.8 | >333.3 | >100 |
| 9 | >1 | 227.3 | >1 |
| 11 | 47.6 | 100 | 38.5 |
| 12 | 16.2 | 61.6 | 17 |
| 13 | 347.6 | 668.46 | 38 |
| 15 | 71.4 | 370 | 22.2 |
| 16 | 57.1 | 400 | 41.2 |
| 17 | 15.7 | 27 | 14.8 |

As can be seen from table 2, the preferred compounds of the present invention have better activity for inhibiting FGFR1, FGFR2 and FGFR3 than FGFR4, and they have better activity for inhibiting FGFR2 than FGFR4; the compounds of Example 1, Example 7, Example 9, Example 13, Example 15 and Example 16 have preferred selective inhibition activity.

Test Example 2. Determination of the Effects of the Compounds of the Present Invention on the Activity of Small Cell Lung Cancer Cells The following assay was used to determine the effect of the preferred compounds of the present invention on tumor cell proliferation by using the CCK-8 kit (Dojindo Chemical Technology). For FGFR1 subtype, small cell lung cancer cells DMS114 and NCI-H1581 (purchased from the Chinese Academy of Sciences, Shanghai Institute of Life Sciences, Cell Resource Center) were used, and cultivated according to the corresponding conditions.

The assay can be briefly described as follows: the tested compound was first dissolved in DMSO to prepare a stock solution, then it was subjected to gradient dilution with corresponding cell culture medium to prepare a tested sample. The final concentration of the compound is in the range of 30 µM to 0.01 nM. The tumor cells in logarithmic growth phase were inoculated into 96-well cell culture plates at appropriate densities. After the cells were incubated overnight under the corresponding conditions, the tested compound samples were added and the cells were cultured for 72 hours. After completion of the culture, a suitable volume of CCK-8 test solution was added to each well and the cells were incubated at 37° C. for 1 to 4 hours. The absorbance values of the wells at 450 nM were then read on a microplate reader. The percentage inhibition rate of the compound at each concentration point was calculated by comparing with the absorbance values of the control group, and then non-linear regression analysis was carried out using logarithmic concentration of the compounds-inhibition rates in the GraphPad Prism 5 software, to obtain the IC$_{50}$ values for inhibiting cell proliferation of the compounds. See table 3 below.

TABLE 3

IC$_{50}$ data of preferred compounds of the invention for inhibition activity of small cell lung cancer cells

| Example No. | IC$_{50}$(nM)/ DMS114 | IC$_{50}$(nM)/ NCI-H1581 |
|---|---|---|
| 1 | 89 | 45 |
| 11 | ND | 119 |
| 12 | 150 | 78 |
| 14 | 43 | 20 |
| 16 | 56 | 40 |
| 17 | 129 | 61 |

As can be seen from table 3, the preferred compounds of the present invention have a significant activity for inhibiting the proliferation of the small cell lung cancer cells with abnormal FGFR1.

ND represents not determined.

Test Example 3. Determination of Effects of the Compounds of the Present Invention on the Activity of Human Gastric Cancer Cells The following assay was used to determine the effect of the preferred compounds of the present invention on tumor cell proliferation by using the CCK-8 kit (Dojindo Chemical Technology). For the FGFR2 subtype, the human gastric cancer cells KATOIII and SNU-16 (purchased from the Chinese Academy of Sciences, Shanghai Institute of Life Sciences, Cell Resource Center) were used, and cultivated according to the corresponding conditions.

The experimental assay can be briefly described as follows: the tested compound was first dissolved in DMSO to prepare a stock solution, then it was subjected to gradient dilution with corresponding cell culture medium to prepare a tested sample. The final concentration of the compound is in the range of 30 µM to 0.01 nM. The tumor cells in logarithmic growth phase were inoculated into 96-well cell culture plates at appropriate densities. After the cells were incubated overnight under the corresponding conditions, the tested compound samples were added and the cells were cultured for 72 hours. After completion of the culture, a suitable volume of CCK-8 test solution was added to each well and the cells were incubated at 37° C. for 1 to 4 hours. The absorbance values of the wells at 450 nM were then read on a microplate reader. The percentage inhibition rate of the compound at each concentration point was calculated by comparing with the absorbance values of the control group, and then non-linear regression analysis was carried out using logarithmic concentration of the compounds-inhibition rates in the GraphPad Prism 5 software, to obtain the $IC_{50}$ values for inhibiting cell proliferation of the compounds. See table 4 below.

TABLE 4

IC$_{50}$ data of preferred compounds of the invention for inhibition activity of human gastric cancer cells

| Experiment No. | IC$_{50}$(nM)/ KATOIII | IC$_{50}$(nM)/ SNU-16 |
|---|---|---|
| 1 | 9 | 4 |
| 11 | 15 | ND |
| 12 | 1.1 | 5 |
| 14 | 4.5 | 5.6 |
| 16 | 11 | ND |
| 17 | 9.8 | ND |

As can be seen from table 4, the preferred compounds of the present invention have a significant activity for inhibiting the proliferation of the human gastric cancer cells with abnormal FGFR2.

ND represents not determined.

Test Example 4. Determination of the Compounds of the Present Invention on the Activity of Bladder Cancer Cells The following assay was used to determine the effect of the preferred compounds of the present invention on tumor cell proliferation by using the CCK-8 kit (Dojindo Chemical Technology). For the FGFR3 subtype, the human bladder transplanted cell carcinoma cell SW780 (purchased from the Chinese Academy of Sciences, Shanghai Institute of Life Sciences, Cell Resource Center) was used, and cultivated according to the corresponding conditions.

The experimental assay can be briefly described as follows: the tested compound was first dissolved in DMSO to prepare a stock solution, then it was subjected to gradient dilution with corresponding cell culture medium to prepare a test sample. The final concentration of the compound is in the range of 30 μM to 0.01 nM. The tumor cells in logarithmic growth phase were inoculated into 96-well cell culture plates at appropriate densities, after the cells were incubated overnight under the corresponding conditions, the tested compound samples were added and the cells were cultured for 72 hours. After completion of the culture, a suitable volume of CCK-8 test solution was added to each well and the cells were incubated at 37° C. for 1 to 4 hours. The absorbance values of the wells at 450 nM were then read on a microplate reader. The percentage inhibition rate of the compound at each concentration point was calculated by comparing with the absorbance values of the control group, and then non-linear regression analysis was carried out using logarithmic concentration of the compounds-inhibition rates in the GraphPad Prism 5 software, to obtain the IC$_{50}$ values for inhibiting cell proliferation of the compounds. See Table 5 below.

TABLE 5

IC$_{50}$ data of preferred compounds of the invention for inhibition activity of bladder cancer cells

| Experiment No. | IC$_{50}$(nM)/ SW780 |
|---|---|
| 1 | 11 |
| 16 | 56 |
| 17 | 106 |

As can be seen from table 5, the preferred compounds of the present invention have a significant activity for inhibiting the proliferation of the bladder cancer cells with abnormal FGFR2.

Test Example 5. Pharmacokinetic Tests on Rats of the Compounds of Examples 12 and 17 of the Present Invention 1. Purpose of the Experiment SD rats were used as the test animals, and the compounds of Examples 12 and 17 were administrated intragastrically to the rats to determine the drug concentration in plasma at different points by LC/MS/MS method. The pharmacokinetic properties of the compounds of the present invention in rats were studied.

2. Scheme of the Experiment 2.1 Drugs and Animals of the Experiment

The compounds of Examples 12 and 17;

6 Healthy adult SD male rats, weight 180-235 g, purchased from Vital River Laboratory Animal Technology Co., Ltd., production license number: 11400700109943.

2.2 Preparation and Administration of Drugs

The compound of Example 12 (3.5 mg) was weighed, dissolved in 2.2 mL of ethanol, vortexed for 1 minute and sonicated for 1 minute, after that, dissolved in 3.3 mL of PEG400, vortexed for 1 minute and sonicated for 1 minute, and then added with 5.5 mL of deionized water, vortexed for 1 minute. The final concentration of the solution was 0.3 mg/mL, and it was a colorless clear liquid (the pH of the final solution was about 7).

The compound of Example 17 (7.12 mg) was weighed and 7.12 mL of 0.5% sodium carboxymethylcellulose (CMC-Na) (0.5% Tween-20, 0.9% BeOH) was added, vortexed for 3 minutes until a homogeneous suspension was formed;

6 healthy adult SD male rats, after an overnight fast, were administrated intragastrically at the dosage of 3 mg/kg and 5 mg/kg, respectively.

2.3 Sample Collection

Blood samples were taken from laryngeal vein (0.15 mL), at pre administration and at 15 minutes, 30 minutes, 1 hour, 2 hours, 4 hours, 8 hours, 12 hours, 24 hours, 36 hours and 48 hours post administration, and the samples were stored in heparinized test tubes, and centrifuged for 10 minutes at 5500 r/min. The plasma was stored at −30° C., and the rats were fed 4 hours after administration.

2.4 Sample Processing

For plasma samples:

20 μL of sample was taken, 400 μl of acetonitrile solution of IS (5 ng·mL$^{-1}$ verapamil and 50 ng·mL$^{-1}$ glibenclamide were contained) was added, The mixture was vortexed for 1 minute, and then centrifuged for 8 minutes at 13,000r/min. After that, 70 μL of supernatant was added with 70 μL of water and vortexed for 10 minutes, and an aliquot of 10 μL of the supernatant of the mixture was analyzed in a LC-MS/MS system.

For dose samples:

The dose samples were diluted with a mixture solvent of methanol and water (4:1, v/v) to reach the concentration of 10 μg·mL$^{-1}$, then 2.5 μL of the diluted sample and 47.5 μL of blank plasma were taken, and then the samples were processed as plasma samples procedure. The supernatant of 10 μL of the mixture was analyzed in a LC-MS/MS system.

The tested compounds were administered intragastrically to determine the content of the tested compounds in plasma of rats at different time points by LC-MS/MS method.

3. Results of the Pharmacokinetic Parameters

The pharmacokinetic parameters of the preferred compounds of the present invention are shown in Table 6.

TABLE 6

Pharmacokinetic data for the compounds of Examples 12 and 17

| Example No. | Dosage of administration (mg/kg) | Plasma concentration Cmax (ng/mL) | Curve area AUC$_{0-\infty}$ (ng · h/mL) | Half-life period T½ (h) | Residence time MRT (h) |
|---|---|---|---|---|---|
| 12 | 3 | 5230 ± 1510 | 80405 ± 24566 | 5.38 ± 0.05 | 8.18 ± 0.19 |
| 17 | 5 | 1041 ± 271 | 10288 ± 3488 | 6.6 ± 3.2 | 9.4 ± 5.2 |

As can be seen from Table 6, the compounds of Examples 12 and 17 of the present invention have good pharmacokinetic properties.

Test Example 6. Pharmacokinetic Tests on Mice of the Compounds of Example 1 of the Present Invention 1. Purpose of the Experiment ICR mice were used as the test animals, and the compound of Example 1 was administered intragastrically to mice to determine the drug concentration in plasma at different points by LC/MS/MS method. The pharmacokinetic properties of the compound of the present invention were studied in mice.

2. Scheme of the Experiment 2.1 Drugs and Animals of the Experiment

The compound of example 1;

9 Healthy adult ICR mice, weight 22.9-26.7 g, purchased from Vital River Laboratory Experimental Animal Technology Co., Ltd., production license number: 11400700162303.

2.2 Preparation and Administration of Drugs

The compound of Example 1 (50.12 mg) was weighed, added with 5.012 mL of 0.5% sodium carboxymethylcellulose (CMC-Na) (0.5% Tween-20, 0.9% BeOH), vortexed for 3 minutes until a homogeneous suspension was formed;

9 healthy adult ICR mice, after an overnight fast, were administrated intragastrically at a dosage of 100 mg/kg, at a volume of 10 mg/mL.

2.3 Sample Collection

Blood samples were taken from orbital vein (0.08 mL) at pre administration and at 15 minutes, 30 minutes, 1 hour, 2 hours, 4 hours, 8 hours, 12 hours, 24 hours post administration. The samples were stored in heparinized test tubes and centrifuged for 10 minutes at 5500r/min, The plasma were stored at −30° C., and the mice were fed after 4 hours of administration.

2.4 Sample Processing

For plasma samples:

10 μL of sample was taken, 100 μl of acetonitrile solution of IS (5 ng·mL$^{-1}$ verapamil and 50 ng·mL$^{-1}$ glibenclamide were contained) was added, the mixture was vortexed for 10 minutes and centrifuged for 18 minutes at 3,700r/min, After that, 40 μL of supernatant was added with 120 μL of water and vortexed for 10 minutes, and an aliquot of 10 μL of the supernatant of the mixture was analyzed in a LC-MS/MS system.

For dose samples:

The dose samples were diluted with DMSO to reach the concentration of 200 μg·mL$^{-1}$ and 1000 μg·mL$^{-1}$, then the samples were diluted with a mixture solvent of methanol and water (4:1, v/v) to a concentration of 20 μg·mL$^{-1}$ and 100 μg·mL$^{-1}$, 2.5 μL of the diluted sample was taken and added with 47.5 μL of blank plasma, then the samples were processed as plasma samples procedure. The supernatant of 10 μL of the mixture was analyzed in a LC-MS/MS system.

The tested compounds were administered intragastrically to determine the content of the tested compounds in plasma of mice at different time points by LC-MS/MS method.

3. Results of the Pharmacokinetic Parameters

The pharmacokinetic parameters of the preferred compound of the present invention are shown in table 7.

TABLE 7

Pharmacokinetic data for the compound of Example 1

| | Pharmacokinetics Assay(100 mg/kg) | | |
|---|---|---|---|
| Experiment No. | Plasma concentration Cmax (ng/mL) | Curve area AUC$_{0-t}$ (ng · h/mL) | F % (oral availability) |
| 1 | 17431 | 150098 | 63% |

As can be seen from table 7, the compound of Example 1 of the present invention has good pharmacokinetic properties.

All documents mentioned in the present invention are incorporated herein by reference, as if each document were individually recited for reference. It is to be understood that those skilled in the art will be able to make various changes or modifications to the present invention after reading the above contents of the present invention, which also fall within the scope of the claims appended hereto.

The invention claimed is:
1. A compound represented by formula (I):

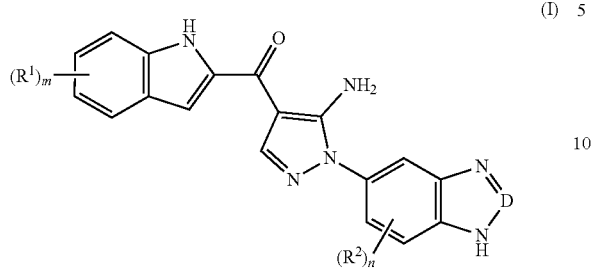

or a pharmaceutically acceptable salt, tautomer or stereoisomer thereof,
wherein:
D is selected from N or $CR^3$;
each $R^1$ is independently selected from the group consisting of hydrogen, alkyl, alkoxy, hydroxy, halogen, nitro, cyano, cycloalkyl, heterocyclyl, aryl, heteroaryl, $-NR^4R^5$, $-C(O)NR^4R^5$, $-C(O)R^6$, $-OC(O)R^6$, $-C(O)OR^6$ and $-NR^4C(O)R^5$, wherein the alkyl, alkoxy, cycloalkyl, heterocyclyl, aryl or heteroaryl is optionally further substituted by one or more substituents selected from the group consisting of halogen, hydroxy, cyano, nitro, alkyl, alkoxy, cycloalkyl, heterocyclyl, aryl, heteroaryl, $-NR^4R^5$, $-C(O)NR^4R^5$, $-C(O)R^6$, $-OC(O)R^6$, $-C(O)OR^6$ and $-NR^4C(O)R^5$;
each $R^2$ is independently selected from the group consisting of hydrogen, alkyl, alkoxy, hydroxy, halogen, nitro, cyano, cycloalkyl, heterocyclyl, $-NR^4R^5$, $-C(O)NR^4R^5$, $-C(O)R^6$, $-OC(O)R^6$, $-C(O)OR^6$ and $-NR^4C(O)R^5$, wherein the alkyl, alkoxy, cycloalkyl or heterocyclyl is optionally further substituted by one or more substituents selected from the group consisting of alkyl, halogen, hydroxy, cyano, nitro, cycloalkyl, heterocyclyl, aryl, heteroaryl, $-NR^4R^5$, $-C(O)NR^4R^5$, $-C(O)R^6$, $-OC(O)R^6$, $-C(O)OR^6$ and $-NR^4C(O)R^5$;
$R^3$ is selected from the group consisting of cycloalkyl, cyano, $-NR^4R^5$, $-C(O)OR^6$, $-OC(O)R^6$, $-NR^4C(O)R^5$ and $-C(O)NR^4R^5$, wherein the cycloalkyl is optionally further substituted with one or more halogens;
$R^4$, $R^5$ and $R^6$ are each independently selected from the group consisting of hydrogen, alkyl, cycloalkyl, heterocyclyl, sodium, aryl and heteroaryl, wherein the alkyl, cycloalkyl, heterocyclyl, aryl or heteroaryl is optionally further substituted by one or more substituents selected from the group consisting of hydroxy, halogen, nitro, cyano, alkyl, alkoxy, cycloalkyl, heterocyclyl, aryl, heteroaryl, $-NR^7R^8$, $-C(O)NR^7R^8$, $-C(O)R^9$, $-C(O)OR^9$ and $-NR^7C(O)R^8$; or
$R^4$ and $R^5$, together with the attached nitrogen atom, form a 4- to 8-membered heterocyclyl, wherein the 4- to 8-membered heterocyclyl contains one or more atoms selected from the group consisting of N, O and $S(O)_p$, and the 4- to 8-membered heterocyclyl is further substituted by one or more substituents selected from the group consisting of hydroxy, halogen, nitro, cyano, alkyl, alkoxy, cycloalkyl, heterocyclyl, aryl, heteroaryl, oxo, $-NR^7R^8$, $-C(O)NR^7R^8$, $-C(O)R^9$, $-C(O)OR^9$ and $-NR^7C(O)R^8$;
$R^7$, $R^8$ and $R^9$ are each independently selected from the group consisting of hydrogen, alkyl, cycloalkyl, heterocyclyl, aryl and heteroaryl, wherein the alkyl, cycloalkyl, heterocyclyl, aryl or heteroaryl is optionally substituted by one or more substituents selected from the group consisting of hydroxy, halogen, nitro, cyano, alkyl, alkoxy, cycloalkyl, heterocyclyl, aryl, heteroaryl, carboxy and carboxylate;
m is 0, 1, 2, 3 or 4;
n is 0, 1, 2 or 3; and
p is 0, 1 or 2.
2. The compound according to claim 1, wherein each $R^1$ is independently selected from the group consisting of hydrogen and alkyl.
3. The compound according to claim 1, wherein each $R^1$ is independently halogen.
4. The compound according to claim 3, wherein each $R^1$ is independently selected from F, Cl or Br.
5. The compound according to claim 1, wherein each $R^1$ is independently heteroaryl, wherein the heteroaryl is optionally further substituted by one or more alkyl substituents.
6. The compound according to claim 5, wherein each $R^1$ is independently pyrazolyl.
7. The compound according to claim 5, wherein the heteroaryl is optionally further substituted with one or more ethyl substituents.
8. The compound according to claim 1, wherein each $R^2$ is independently selected from the group consisting of hydrogen and alkyl.
9. The compound according to claim 1, wherein D is $CR^3$.
10. The compound according to claim 9, wherein:
each $R^1$ is independently hydrogen;
each $R^2$ is independently hydrogen; and
$R^3$ is cycloalkyl, wherein the cycloalkyl is optionally further substituted with one or more halogens.
11. The compound according to claim 10, wherein $R^3$ is selected from the group consisting of cyclopropyl, cyclobutyl and cyclopentyl.
12. The compound according to claim 10, wherein $R^3$ is cyclopropyl.
13. The compound according to claim 9, wherein:
each $R^1$ is independently selected from the group consisting of halogen, cyano, cycloalkyl, heterocyclyl and heteroaryl, wherein the cycloalkyl, heterocyclyl or heteroaryl is optionally further substituted by one or more substituents selected from the group consisting of halogen, alkyl and alkoxy;
each $R^2$ is independently hydrogen; and
$R^3$ is cycloalkyl, wherein the cycloalkyl is optionally further substituted with one or more halogens.
14. The compound according to claim 13, wherein $R^3$ is selected from the group consisting of cyclopropyl, cyclobutyl and cyclopentyl.
15. The compound according to claim 9, wherein:
each $R^1$ is independently hydrogen;
each $R^2$ is independently hydrogen;
$R^3$ is $-C(O)OR^6$; and
$R^6$ is selected from the group consisting of hydrogen, methyl, ethyl, propyl and butyl.
16. The compound according to claim 15, wherein $R^6$ is methyl or ethyl.
17. The compound according to claim 9, wherein:
each $R^1$ is independently hydrogen;
each $R^2$ is independently hydrogen; and $R^3$ is selected from the group consisting of —NR⁴R⁵, —C(O)OR⁶, —NR⁴C(O)R⁵ and —C(O)NR⁴R⁵.
18. The compound according to claim 1, wherein:
m is 0, 1 or 2; and
n is 0, 1 or 2.
19. The compound according to claim 1, wherein the compound is selected from the group consisting of:
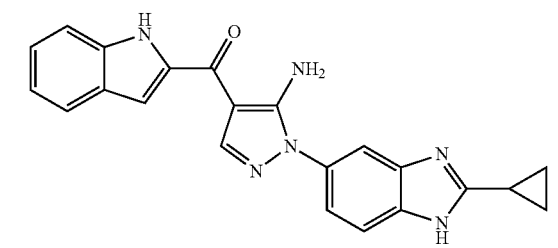
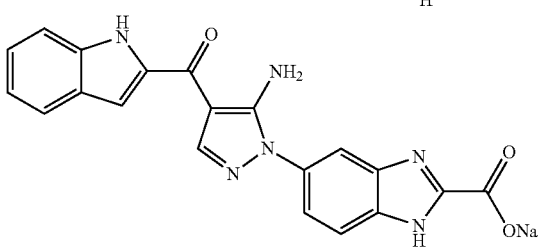
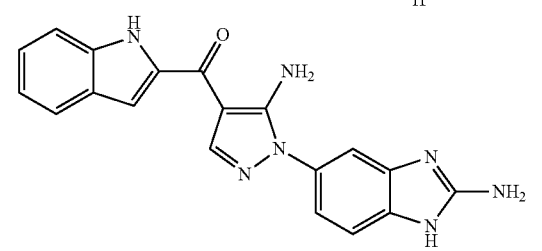
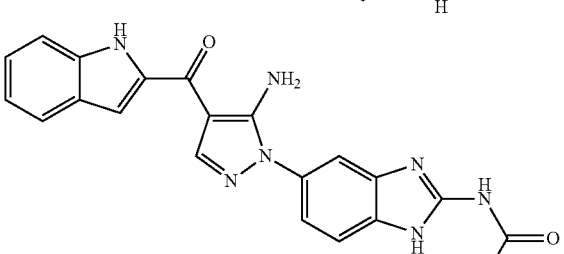
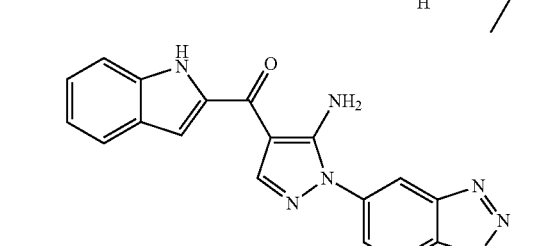
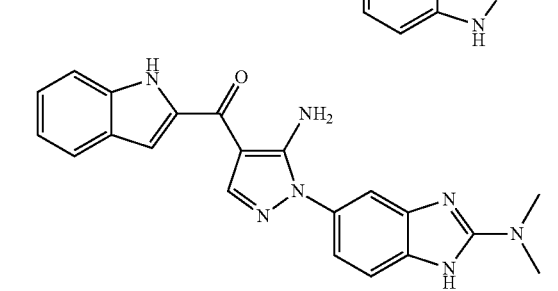
-continued
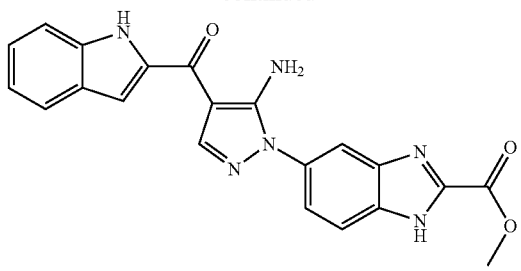
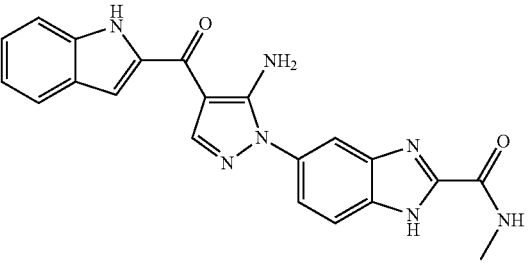
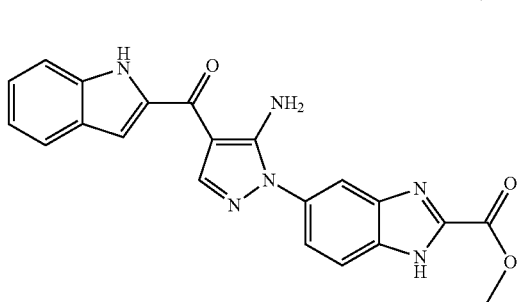
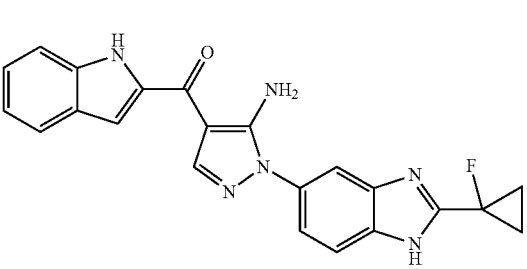
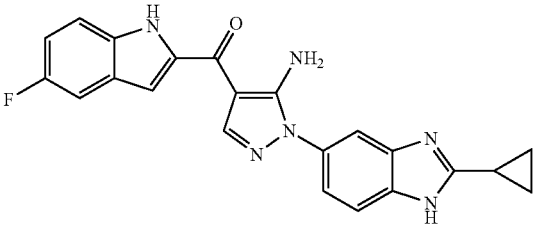
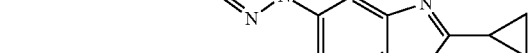

-continued

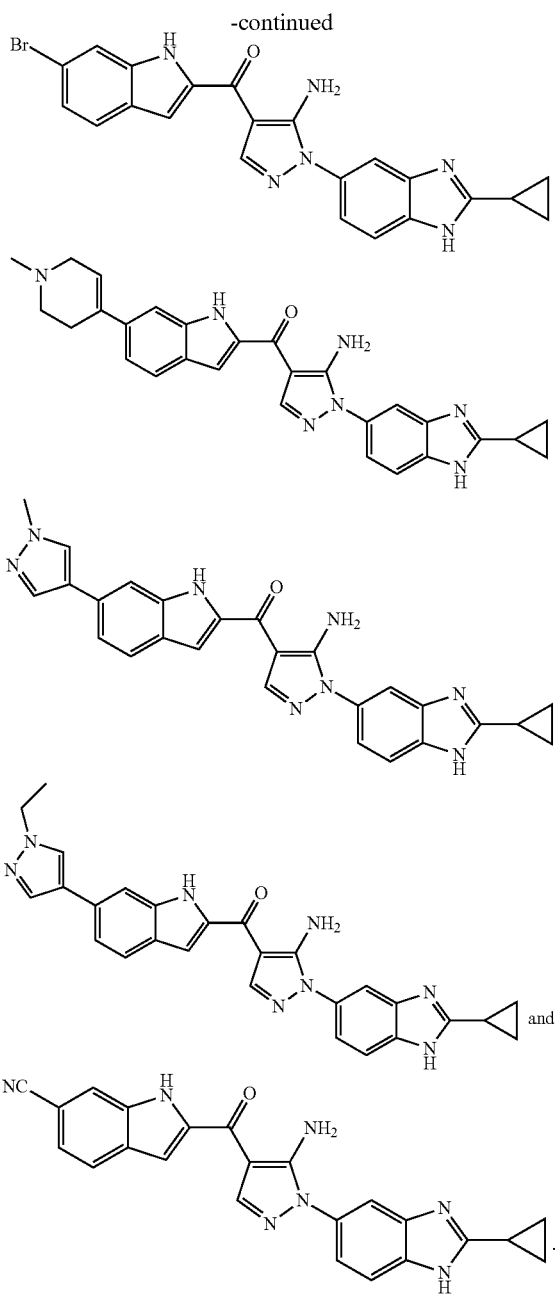

20. A pharmaceutical composition comprising an effective amount of the compound according to claim 1, or a pharmaceutically acceptable salt, tautomer or stereoisomer thereof, and a pharmaceutically acceptable carrier or excipient, or a combination thereof.

21. A method for inhibiting fibroblast growth factor receptor in vitro, comprising contacting the receptor with the compound according to claim 1, or a pharmaceutically acceptable salt, tautomer or stereoisomer thereof.

22. The method according to claim 21, wherein the fibroblast growth factor receptor is selected from the group consisting of FGFR1, FGFR2 and FGFR3.

23. A method for inhibiting fibroblast growth factor receptor in vitro, comprising contacting the receptor with the pharmaceutical composition according to claim 20.

24. A method for inhibiting fibroblast growth factor receptor activity in a patient, comprising administering to the patient an effective amount of the compound according to claim 1, or a pharmaceutically acceptable salt, tautomer or stereoisomer.

25. The method according to claim 24, wherein the patient has cancer.

26. The method according to claim 25, wherein the cancer is selected from the group consisting of lung cancer, gastric cancer, multiple myeloma, bladder cancer and liver cancer.

27. A method for inhibiting fibroblast growth factor receptor activity in a patient, comprising administering to the patient an effective amount of the pharmaceutical composition according to claim 20.

28. A method for the preparation of the compound represented by formula (I) according to claim 1:

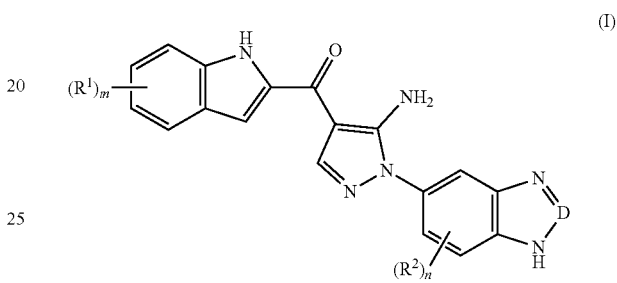

(I)

wherein the method comprises the following step(s):
  (i) reacting a compound represented by formula (IA):

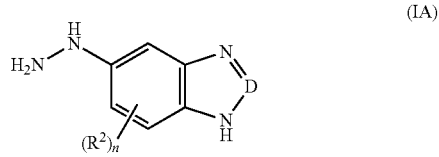

(IA)

wherein:
  D is selected from N or CR³;
  each R² is independently selected from the group consisting of hydrogen, alkyl, alkoxy, hydroxy, halogen, nitro, cyano, cycloalkyl, heterocyclyl, —NR⁴R⁵, —C(O)NR⁴R⁵, —C(O)R⁶, —OC(O)R⁶, —C(O)OR⁶ and —NR⁴C(O)R⁵, wherein the alkyl, alkoxy, cycloalkyl or heterocyclyl is optionally further substituted by one or more substituents selected from the group consisting of alkyl, halogen, hydroxy, cyano, nitro, cycloalkyl, heterocyclyl, aryl, heteroaryl, —NR⁴R⁵, —C(O)NR⁴R⁵, —C(O)R⁶, —OC(O)R⁶, —C(O)OR⁶ and —NR⁴C(O)R⁵;
  R³ is selected from the group consisting of cycloalkyl, cyano, —NR⁴R⁵, —C(O)OR⁶, —OC(O)R⁶, —NR⁴C(O)R⁵ and —C(O)NR⁴R⁵, wherein the cycloalkyl is optionally further substituted with one or more halogens;
  R⁴, R⁵ and R⁶ are each independently selected from the group consisting of hydrogen, alkyl, cycloalkyl, heterocyclyl, sodium, aryl and heteroaryl, wherein the alkyl, cycloalkyl, heterocyclyl, aryl or heteroaryl is optionally further substituted by one or more substituents selected from the group consisting of hydroxy, halogen, nitro, cyano, alkyl, alkoxy, cycloalkyl, heterocyclyl, aryl, heteroaryl, —NR⁷R⁸, —C(O)NR⁷R⁸, —C(O)R⁹, —C(O)OR⁹ and —NR⁷C(O)R⁸; or R⁴ and R⁵, together with the attached nitrogen atom, form a 4- to 8-membered heterocyclyl, wherein the 4- to 8-membered heterocyclyl contains one or more atoms selected from the group consisting of N, O and S(O)$_p$, and the 4- to 8-membered heterocyclyl is further substituted by one or more substituents selected from the group consisting of hydroxy, halogen, nitro, cyano, alkyl, alkoxy, cycloalkyl, heterocyclyl, aryl, heteroaryl, oxo, —NR⁷R⁸, —C(O)NR⁷R⁸, —C(O)R⁹, —C(O)OR⁹ and —NR⁷C(O)R⁸;

R⁷, R⁸ and R⁹ are each independently selected from the group consisting of hydrogen, alkyl, cycloalkyl, heterocyclyl, aryl and heteroaryl, wherein the alkyl, cycloalkyl, heterocyclyl, aryl or heteroaryl is optionally substituted by one or more substituents selected from the group consisting of hydroxy, halogen, nitro, cyano, alkyl, alkoxy, cycloalkyl, heterocyclyl, aryl, heteroaryl, carboxy and carboxylate;

n is 0, 1, 2 or 3; and p is 0, 1 or 2;

with a compound represented by formula (IB):

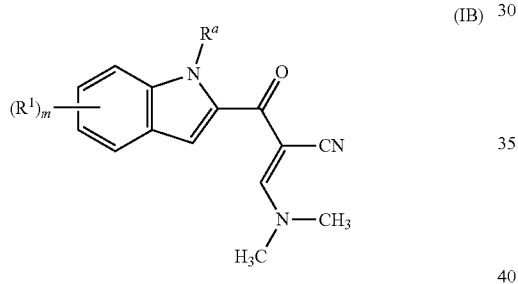

(IB)

wherein:

R$^a$ is phenylsulfonyl;

each R¹ is independently selected from the group consisting of hydrogen, alkyl, alkoxy, hydroxy, halogen, nitro, cyano, cycloalkyl, heterocyclyl, aryl, heteroaryl, —NR⁴R⁵, —C(O)NR⁴R⁵, —C(O)R⁶, —OC(O)R⁶, —C(O)OR⁶ and —NR⁴C(O)R⁵, wherein the alkyl, alkoxy, cycloalkyl, heterocyclyl, aryl or heteroaryl is optionally further substituted by one or more substituents selected from the group consisting of halogen, hydroxy, cyano, nitro, alkyl, alkoxy, cycloalkyl, heterocyclyl, aryl, heteroaryl, —NR⁴R⁵, —C(O)NR⁴R⁵, —C(O)R⁶, —OC(O)R⁶, —C(O)OR⁶ and —NR⁴C(O)R⁵;

R⁴, R⁵ and R⁶ are each independently selected from the group consisting of hydrogen, alkyl, cycloalkyl, heterocyclyl, sodium, aryl and heteroaryl, wherein the alkyl, cycloalkyl, heterocyclyl, aryl or heteroaryl is optionally further substituted by one or more substituents selected from the group consisting of hydroxy, halogen, nitro, cyano, alkyl, alkoxy, cycloalkyl, heterocyclyl, aryl, heteroaryl, —NR⁷R⁸, —C(O)NR⁷R⁸, —C(O)R⁹, —C(O)OR⁹ and —NR⁷C(O)R⁸; or R⁴ and R⁵, together with the attached nitrogen atom, form a 4- to 8-membered heterocyclyl, wherein the 4- to 8-membered heterocyclyl contains one or more atoms selected from the group consisting of N, O and S(O)$_p$, and the 4- to 8-membered heterocyclyl is further substituted by one or more substituents selected from the group consisting of hydroxy, halogen, nitro, cyano, alkyl, alkoxy, cycloalkyl, heterocyclyl, aryl, heteroaryl, oxo, —NR⁷R⁸, —C(O)NR⁷R⁸, —C(O)R⁹, —C(O)OR⁹ and —NR⁷C(O)R⁸;

R⁷, R⁸ and R⁹ are each independently selected from the group consisting of hydrogen, alkyl, cycloalkyl, heterocyclyl, aryl and heteroaryl, wherein the alkyl, cycloalkyl, heterocyclyl, aryl or heteroaryl is optionally substituted by one or more substituents selected from the group consisting of hydroxy, halogen, nitro, cyano, alkyl, alkoxy, cycloalkyl, heterocyclyl, aryl, heteroaryl, carboxy and carboxylate;

m is 0, 1, 2, 3 or 4; and p is 0, 1 or 2;

in the presence of ethanol, to provide a compound represented by the following formula:

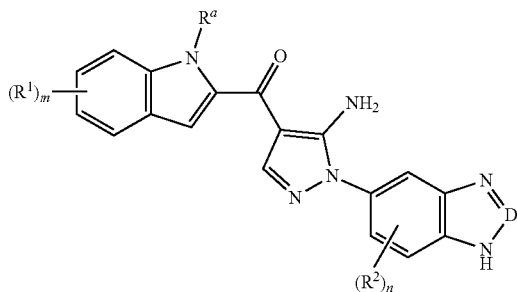

wherein:

D is selected from N or CR³;

R$^a$ is phenylsulfonyl;

each R¹ is independently selected from the group consisting of hydrogen, alkyl, alkoxy, hydroxy, halogen, nitro, cyano, cycloalkyl, heterocyclyl, aryl, heteroaryl, —NR⁴R⁵, —C(O)NR⁴R⁵, —C(O)R⁶, —OC(O)R⁶, —C(O)OR⁶ and —NR⁴C(O)R⁵, wherein the alkyl, alkoxy, cycloalkyl, heterocyclyl, aryl or heteroaryl is optionally further substituted by one or more substituents selected from the group consisting of halogen, hydroxy, cyano, nitro, alkyl, alkoxy, cycloalkyl, heterocyclyl, aryl, heteroaryl, —NR⁴R⁵, —C(O)NR⁴R⁵, —C(O)R⁶, —OC(O)R⁶, —C(O)OR⁶ and —NR⁴C(O)R⁵;

each R² is independently selected from the group consisting of hydrogen, alkyl, alkoxy, hydroxy, halogen, nitro, cyano, cycloalkyl, heterocyclyl, —NR⁴R⁵, —C(O)NR⁴R⁵, —C(O)R⁶, —OC(O)R⁶, —C(O)OR⁶ and —NR⁴C(O)R⁵, wherein the alkyl, alkoxy, cycloalkyl or heterocyclyl is optionally further substituted by one or more substituents selected from the group consisting of alkyl, halogen, hydroxy, cyano, nitro, cycloalkyl, heterocyclyl, aryl, heteroaryl, —NR⁴R⁵, —C(O)NR⁴R⁵, —C(O)R⁶, —OC(O)R⁶, —C(O)OR⁶ and —NR⁴C(O)R⁵;

R³ is selected from the group consisting of cycloalkyl, cyano, —NR⁴R⁵, —C(O)OR⁶, —OC(O)R⁶, —NR⁴C(O)R⁵ and —C(O)NR⁴R⁵, wherein the cycloalkyl is optionally further substituted with one or more halogens;

R⁴, R⁵ and R⁶ are each independently selected from the group consisting of hydrogen, alkyl, cycloalkyl, heterocyclyl, sodium, aryl and heteroaryl, wherein the alkyl, cycloalkyl, heterocyclyl, aryl or heteroaryl is optionally further substituted by one or more substituents selected from the group consisting of hydroxy, halogen, nitro, cyano, alkyl, alkoxy, cycloalkyl, heterocyclyl, aryl, heteroaryl, —NR⁷R⁸, —C(O)NR⁷R⁸, —C(O)R⁹, —C(O)OR⁹ and —NR⁷C(O)R⁸; or R⁴ and R⁵, together with the attached nitrogen atom, form a 4- to 8-membered heterocyclyl, wherein the 4- to 8-membered heterocyclyl contains one or more atoms selected from the group consisting of N, O and S(O)$_p$, and the 4- to 8-membered heterocyclyl is further substituted by one or more substituents selected from the group consisting of hydroxy, halogen, nitro, cyano, alkyl, alkoxy, cycloalkyl, heterocyclyl, aryl, heteroaryl, oxo, —NR⁷R⁸, —C(O)NR⁷R⁸, —C(O)R⁹, —C(O)OR⁹ and —NR⁷C(O)R⁸;

R⁷, R⁸ and R⁹ are each independently selected from the group consisting of hydrogen, alkyl, cycloalkyl, heterocyclyl, aryl and heteroaryl, wherein the alkyl, cycloalkyl, heterocyclyl, aryl or heteroaryl is optionally substituted by one or more substituents selected from the group consisting of hydroxy, halogen, nitro, cyano, alkyl, alkoxy, cycloalkyl, heterocyclyl, aryl, heteroaryl, carboxy and carboxylate;

m is 0, 1, 2, 3 or 4;
n is 0, 1, 2 or 3; and
p is 0, 1 or 2; and (ii) reacting the compound prepared in step (i) above with sodium hydroxide in the presence of ethanol, to provide the compound of formula (I) above according to claim 1; or reacting a compound represented by formula (IA):

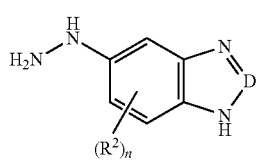

(IA)

wherein:
D is selected from N or CR³;
each R² is independently selected from the group consisting of hydrogen, alkyl, alkoxy, hydroxy, halogen, nitro, cyano, cycloalkyl, heterocyclyl, —NR⁴R⁵, —C(O)NR⁴R⁵, —C(O)R⁶, —OC(O)R⁶, —C(O)OR⁶ and —NR⁴C(O)R⁵, wherein the alkyl, alkoxy, cycloalkyl or heterocyclyl is optionally further substituted by one or more substituents selected from the group consisting of alkyl, halogen, hydroxy, cyano, nitro, cycloalkyl, heterocyclyl, aryl, heteroaryl, —NR⁴R⁵, —C(O)NR⁴R⁵, —C(O)R⁶, —OC(O)R⁶, —C(O)OR⁶ and —NR⁴C(O)R⁵;

R³ is selected from the group consisting of cycloalkyl, cyano, —NR⁴R⁵, —C(O)OR⁶, —OC(O)R⁶, —NR⁴C(O)R⁵ and —C(O)NR⁴R⁵, wherein the cycloalkyl is optionally further substituted with one or more halogens;

R⁴, R⁵ and R⁶ are each independently selected from the group consisting of hydrogen, alkyl, cycloalkyl, heterocyclyl, sodium, aryl and heteroaryl, wherein the alkyl, cycloalkyl, heterocyclyl, aryl or heteroaryl is optionally further substituted by one or more substituents selected from the group consisting of hydroxy, halogen, nitro, cyano, alkyl, alkoxy, cycloalkyl, heterocyclyl, aryl, heteroaryl, —NR⁷R⁸, —C(O)NR⁷R⁸, —C(O)R⁹, —C(O)OR⁹ and —NR⁷C(O)R⁸; or R⁴ and R⁵, together with the attached nitrogen atom, form a 4- to 8-membered heterocyclyl, wherein the 4- to 8-membered heterocyclyl contains one or more atoms selected from the group consisting of N, O and S(O)$_p$, and the 4- to 8-membered heterocyclyl is further substituted by one or more substituents selected from the group consisting of hydroxy, halogen, nitro, cyano, alkyl, alkoxy, cycloalkyl, heterocyclyl, aryl, heteroaryl, oxo, —NR⁷R⁸, —C(O)NR⁷R⁸, —C(O)R⁹, —C(O)OR⁹ and —NR⁷C(O)R⁸;

R⁷, R⁸ and R⁹ are each independently selected from the group consisting of hydrogen, alkyl, cycloalkyl, heterocyclyl, aryl and heteroaryl, wherein the alkyl, cycloalkyl, heterocyclyl, aryl or heteroaryl is optionally substituted by one or more substituents selected from the group consisting of hydroxy, halogen, nitro, cyano, alkyl, alkoxy, cycloalkyl, heterocyclyl, aryl, heteroaryl, carboxy and carboxylate;

n is 0, 1, 2 or 3; and
p is 0, 1 or 2;

with a compound represented by formula (IB):

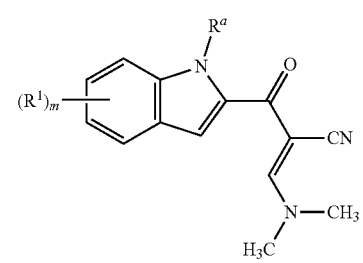

(IB)

wherein:
Rᵃ is hydrogen;
each R¹ is independently selected from the group consisting of hydrogen, alkyl, alkoxy, hydroxy, halogen, nitro, cyano, cycloalkyl, heterocyclyl, aryl, heteroaryl, —NR⁴R⁵, —C(O)NR⁴R⁵, —C(O)R⁶, —OC(O)R⁶, —C(O)OR⁶ and —NR⁴C(O)R⁵, wherein the alkyl, alkoxy, cycloalkyl, heterocyclyl, aryl or heteroaryl is optionally further substituted by one or more substituents selected from the group consisting of halogen, hydroxy, cyano, nitro, alkyl, alkoxy, cycloalkyl, heterocyclyl, aryl, heteroaryl, —NR$^4$R$^5$, —C(O)NR$^4$R$^5$, —C(O)R$^6$, —OC(O)R$^6$, —C(O)OR$^6$ and —NR$^4$C(O)R$^5$;

R$^4$, R$^5$ and R$^6$ are each independently selected from the group consisting of hydrogen, alkyl, cycloalkyl, heterocyclyl, sodium, aryl and heteroaryl, wherein the alkyl, cycloalkyl, heterocyclyl, aryl or heteroaryl is optionally further substituted by one or more substituents selected from the group consisting of hydroxy, halogen, nitro, cyano, alkyl, alkoxy, cycloalkyl, heterocyclyl, aryl, heteroaryl, —NR$^7$R$^8$, —C(O)NR$^7$R$^8$, —C(O)R$^9$, —C(O)OR$^9$ and —NR$^7$C(O)R$^8$; or R$^4$ and R$^5$, together with the attached nitrogen atom, form a 4- to 8-membered heterocyclyl, wherein the 4- to 8-membered heterocyclyl contains one or more atoms selected from the group consisting of N, O and S(O)$_p$, and the 4- to 8-membered heterocyclyl is further substituted by one or more substituents selected from the group consisting of hydroxy, halogen, nitro, cyano, alkyl, alkoxy, cycloalkyl, heterocyclyl, aryl, heteroaryl, oxo, —NR$^7$R$^8$, —C(O)NR$^7$R$^8$, —C(O)R$^9$, —C(O)OR$^9$ and —NR$^7$C(O)R$^8$;

R$^7$, R$^8$ and R$^9$ are each independently selected from the group consisting of hydrogen, alkyl, cycloalkyl, heterocyclyl, aryl and heteroaryl, wherein the alkyl, cycloalkyl, heterocyclyl, aryl or heteroaryl is optionally substituted by one or more substituents selected from the group consisting of hydroxy, halogen, nitro, cyano, alkyl, alkoxy, cycloalkyl, heterocyclyl, aryl, heteroaryl, carboxy and carboxylate;

m is 0, 1, 2, 3 or 4; and p is 0, 1 or 2;

in the presence of ethanol, to provide the compound represented by formula (I) above according to claim 1.

* * * * *